US012630859B2

(12) United States Patent
Gerard et al.

(10) Patent No.: US 12,630,859 B2
(45) Date of Patent: May 19, 2026

(54) METHOD FOR TRANSCRIPTOME ANALYSIS OF SINGLE CELLS

(71) Applicant: HIFIBIO SAS, Paris (FR)

(72) Inventors: Annabelle Patricia Véronique Gerard, Paris (FR); Kévin Armand Grosselin, Paris (FR); Adeline Frédérique Joëlle Poitou, Malakoff (FR); Sami Ellouze, Chatenay Malabry (FR); Yannick Michel Louis Pousse, Villejuif (FR); Marcel Reichen, Bonaduz (CH); Allan Jensen, Frederiksberg (DK); Colin Brenan, Marblehead, MA (US)

(73) Assignee: HIFIBIO SAS, Paris (FR)

( * ) Notice: Subject to any disclaimer, the term of this patent is extended or adjusted under 35 U.S.C. 154(b) by 364 days.

(21) Appl. No.: 16/060,723

(22) PCT Filed: Dec. 8, 2016

(86) PCT No.: PCT/EP2016/080341
§ 371 (c)(1),
(2) Date: Nov. 13, 2018

(87) PCT Pub. No.: WO2017/097939
PCT Pub. Date: Jun. 15, 2017

(65) Prior Publication Data
US 2019/0345537 A1 Nov. 14, 2019

Related U.S. Application Data

(60) Provisional application No. 62/264,414, filed on Dec. 8, 2015.

(30) Foreign Application Priority Data

Jun. 28, 2016 (EP) .................................... 16305783

(51) Int. Cl.
C12Q 1/6806 (2018.01)

(52) U.S. Cl.
CPC ................................. C12Q 1/6806 (2013.01)

(58) Field of Classification Search
CPC ................................................... C12Q 1/6806
See application file for complete search history.

(56) References Cited

U.S. PATENT DOCUMENTS

| | | | |
|---|---|---|---|
| 5,641,870 A | 6/1997 | Rinderknecht et al. | |
| 2007/0003442 A1 | 1/2007 | Link et al. | |
| 2007/0195127 A1 | 8/2007 | Ahn et al. | |
| 2011/0059556 A1 † | 3/2011 | Strey | |
| 2015/0298091 A1 | 10/2015 | Weitz | |
| 2015/0299784 A1 * | 10/2015 | Fan ...................... | C12Q 1/6876 506/4 |
| 2016/0032282 A1 | 2/2016 | Vigneault et al. | |

FOREIGN PATENT DOCUMENTS

| | | | | |
|---|---|---|---|---|
| CA | 2953374 A1 | 12/2015 | | |
| EP | 3263715 A1 | 1/2018 | | |
| WO | WO-2004002627 A2 | 1/2004 | | |
| WO | WO-2004091763 A2 | 10/2004 | | |
| WO | WO-2008109176 A2 | 9/2008 | | |
| WO | 2012048340 A2 † | 4/2012 | | |
| WO | WO-2012083225 A2 * | 6/2012 | ........... | C12Q 1/6883 |
| WO | WO-2014210353 A2 | 12/2014 | | |
| WO | WO-2015164212 A1 | 10/2015 | | |
| WO | WO-2015176162 A1 * | 11/2015 | ......... | C07K 14/7051 |
| WO | WO-2015200893 A2 | 12/2015 | | |
| WO | WO 2016/207441 A1 | 12/2016 | | |
| WO | WO 2017/097939 A1 | 6/2017 | | |

OTHER PUBLICATIONS

Fan, Combinatorial labeling of single cells for gene expression cytometry, Science, 347(6222), Article Summary (1 p.) and Article, pp. 1-8, Feb. 2015. (Year: 2015).*
Georgiou, The promise and challenge of high-throughput sequencing of the antibody repertoire, Nat. Biotechnol., 32(2): 158-68, 2014. (Year: 2014).*
Invitrogen, SuperScript III First-Strand Synthesis System for RT-PCR, 2003. (Year: 2003).*
Macosko, Evan Z. et al.: "Highly Parallel Genome-wide Expression Profiling of Individual Cells Using Nanoliter Droplets". Cell, 161(5): 1202-1214. (2015).
International Search Report and Written Opinion were mailed on Feb. 22, 2017 by the International Searching Authority for Application No. PCT/EP2016/080341, filed Dec. 8, 2016, and published as WO 2017/097939 on Jun. 15, 2017 (Applicant—Hifibio) (10 pages).
European Search Report was mailed on Jan. 31, 2017 by the European Patent Office for U.S. Appl. No. 16/305,783, filed Jun. 28, 2016, and published as EP 3263715 A1 on Jan. 3, 2018 (Applicant—Hifibio) (6 pages).
Dekosky et al., "In-depth determination and analysis of the human paired heavy- and light-chain antibody repertoire", Nature Medicine, 21(1): 86-91 (2015).
Eastburn et al., "Ultrahigh-Throughput Mammalian Single-Cell Reverse-Transcriptase Polymerase Chain Reaction in Microfluidic Drops" Anal Chem (2013) vol. 85, No. 16 pp. 8016-8021.
Rohatgi, et al., "Systematic design and testing of nested (RT-)PCR primers for specific amplification of mouse rearranged/expressed immunoglobulin variable region genes from small number of B cells", Journal of Immunological Methods, 339(2): 205-219 (2008).
Rotem, A., et al., "High-Throughput Single-Cell Labeling (Hi-SCL) for RNA-Seq Using Drop-Based Microfluidics", Plos One, 10(5):9 pages (2015).

(Continued)

*Primary Examiner* — Gary Benzion
*Assistant Examiner* — Carolyn L Greene
(74) *Attorney, Agent, or Firm* — McCarter & English, LLP; Yu Lu; James M. Alburger

(57) ABSTRACT

The present invention concerns a method for capturing and barcoding nucleic acid from single cells, a plurality of microfluidic droplets and a method for preparing said plurality of microfluidic droplets.

18 Claims, 19 Drawing Sheets

Specification includes a Sequence Listing.

(56) References Cited

OTHER PUBLICATIONS

White, A. et al., "High-throughput microfluidic single-cell RT-qPCR", PNAS 108(34): 13999-14004 (2011).

Klein,et al.,"Droplet Barcoding for Single-Cell Transcriptomics Applied to Embryonic Stem Cells", Cell, 161: 1187-1201, 2015.

Clontech Laboratories Inc. SMARTScribe Reverse Transcriptase Protocol-At-A-Glance. 2 pages. 2015.

Invitrogen by Life Technologies. SuperScript III First-Strand Synthesis System for RT-PCR. Catalog No. 18080-051. 4 pages. Jan. 14, 2013.

Invitrogen by Life Technologies. SuperScript IV Reverse Transcriptase. 2 pages. Feb. 3, 2015.

Mary et al., Analysis of gene expression at the single-cell level using microdroplet-based microfluidic technology. Biomicrofluidics. Jun. 2011;5(2):24109, 10 pages.

Zhang et al., Massively parallel single-molecule and single-cell emulsion reverse transcription polymerase chain reaction using agarose droplet microfluidics. Anal Chem. Apr. 17, 2012;84(8):3599-606.

Kapabiosystems, KAPA HiFi HotStart ReadyMax PCR Kit. KR0370—v.5.13. Technical Data Sheet. 3 pages, Oct. 1, 2013.

Clausell-Tormos et al., Droplet-Based Microfluidic Platformsfor the Encapsulation and Screening of Mammalian Cells and Multicellular Organisms, (2008) Chem. Biol. 15:427.†

* cited by examiner
† cited by third party

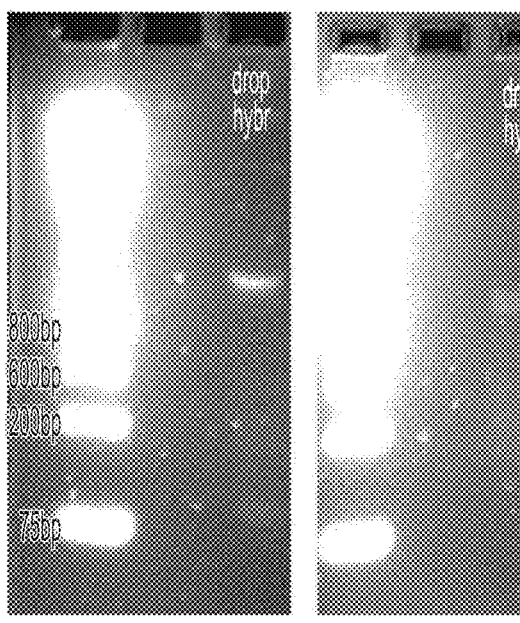
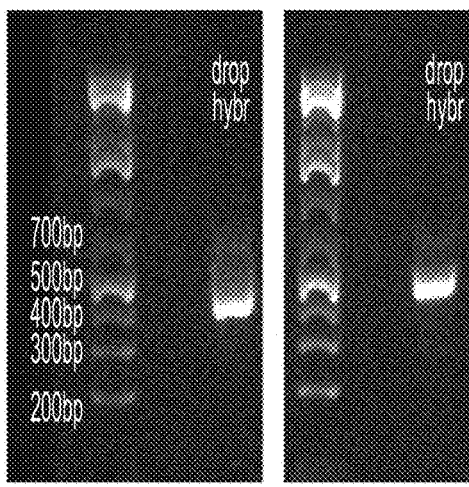
FIG.4A
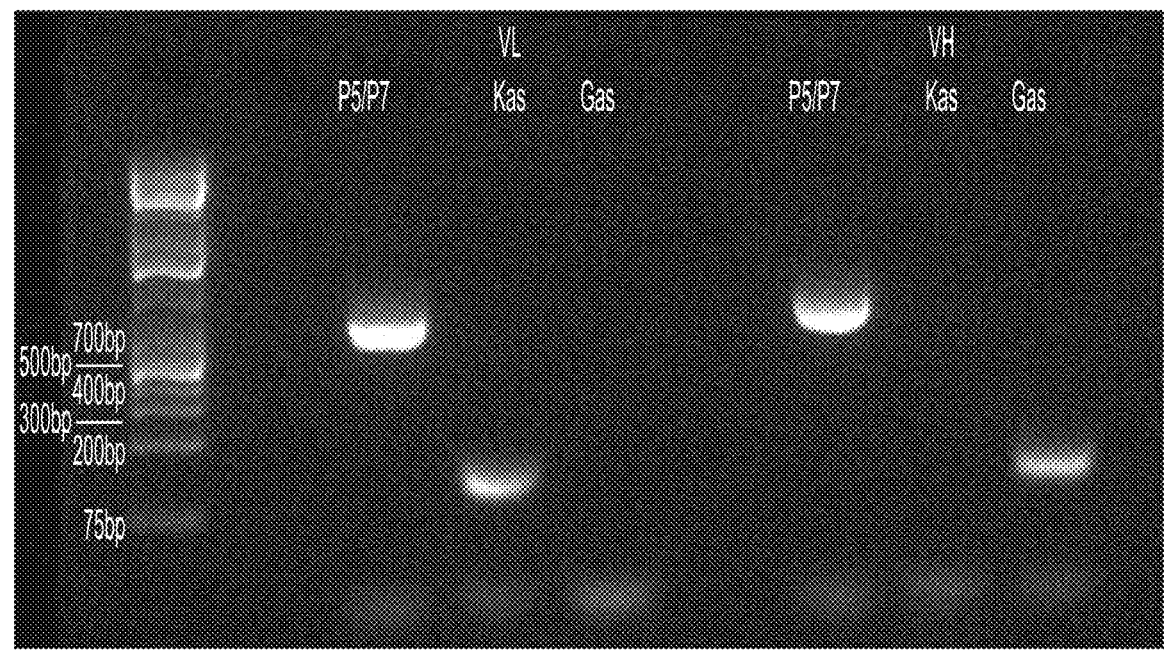

| | Read threshold for VH and VL | | | | | |
|---|---|---|---|---|---|---|
| | 1 | 5 | 10 | 20 | 50 | 100 |
| No. of pairs | 1380 | 726 | 639 | 603 | 552 | 508 |

SEQUENCE LISTING

<160> NUMBER OF SEQ ID NOS: 139

<210> SEQ ID NO 1
<211> LENGTH: 58
<212> TYPE: DNA
<213> ORGANISM: Artificial Sequence
<220> FEATURE:
<223> OTHER INFORMATION: antisense primer Top_SBS12-ATP5G3

-continued

<400> SEQUENCE: 1
caacgtgact ggagttcaga cgtgtgctct tccgatctct gcttcagcga agggtttc          58

<210> SEQ ID NO 2
<211> LENGTH: 57
<212> TYPE: DNA
<213> ORGANISM: Artificial Sequence
<220> FEATURE:
<223> OTHER INFORMATION: antisense primer Top_SBS12- RPS29

<400> SEQUENCE: 2
caacgtgact ggagttcaga cgtgtgctct tccgatctac agacacgaca agagcga          57

<210> SEQ ID NO 3
<211> LENGTH: 59
<212> TYPE: DNA
<213> ORGANISM: Artificial Sequence
<220> FEATURE:
<223> OTHER INFORMATION: antisense primer Top_SBS12- ZNF780A

<400> SEQUENCE: 3
caacgtgact ggagttcaga cgtgtgctct tccgatcttg atccatggac catgttgct          59

<210> SEQ ID NO 4
<211> LENGTH: 53
<212> TYPE: DNA
<213> ORGANISM: Artificial Sequence
<220> FEATURE:
<223> OTHER INFORMATION: sense primer SBS3-ATP5G3

<400> SEQUENCE: 4
acactctttc cctacacgac gctcttccga tctcaggtgc tgcaacagta gga          53

<210> SEQ ID NO 5
<211> LENGTH: 53
<212> TYPE: DNA
<213> ORGANISM: Artificial Sequence
<220> FEATURE:
<223> OTHER INFORMATION: sense primer SBS3-RPS29

<400> SEQUENCE: 5
acactctttc cctacacgac gctcttccga tctttacctc gttgcactgc tga          53

<210> SEQ ID NO 6
<211> LENGTH: 52
<212> TYPE: DNA
<213> ORGANISM: Artificial Sequence
<220> FEATURE:
<223> OTHER INFORMATION: sense primer SBS3-ZNF780A

<400> SEQUENCE: 6
acactctttc cctacacgac gctcttccga tctagagcgt tactgctgca ca          52

<210> SEQ ID NO 7
<211> LENGTH: 24
<212> TYPE: DNA
<213> ORGANISM: Artificial Sequence
<220> FEATURE:
<223> OTHER INFORMATION: antisense primer for mouse ATP5G3

<400> SEQUENCE: 7
caactgcaac tctggatcca gctc          24

<210> SEQ ID NO 8

-continued

```
<211> LENGTH: 53
<212> TYPE: DNA
<213> ORGANISM: Artificial Sequence
<220> FEATURE:
<223> OTHER INFORMATION: sense primer for mouse ATP5G3

<400> SEQUENCE: 8
acactctttc cctacacgac gctcttccga tcttcgcctg tcacctagat cca          53

<210> SEQ ID NO 9
<211> LENGTH: 24
<212> TYPE: DNA
<213> ORGANISM: Artificial Sequence
<220> FEATURE:
<223> OTHER INFORMATION: RT primer VH_1 for VH

<400> SEQUENCE: 9
ggccagtgga tagacagatg gggg                                           24

<210> SEQ ID NO 10
<211> LENGTH: 24
<212> TYPE: DNA
<213> ORGANISM: Artificial Sequence
<220> FEATURE:
<223> OTHER INFORMATION: RT primer VH_2 for VH

<400> SEQUENCE: 10
ggccagtgga tagaccgatg gggc                                           24

<210> SEQ ID NO 11
<211> LENGTH: 24
<212> TYPE: DNA
<213> ORGANISM: Artificial Sequence
<220> FEATURE:
<223> OTHER INFORMATION: RT primer VH_3 for VH

<400> SEQUENCE: 11
ggccagtgga tagactgatg gggg                                           24

<210> SEQ ID NO 12
<211> LENGTH: 24
<212> TYPE: DNA
<213> ORGANISM: Artificial Sequence
<220> FEATURE:
<223> OTHER INFORMATION: RT primer VH_4 for VH

<400> SEQUENCE: 12
gtcaccgcag ccagggacca aggg                                           24

<210> SEQ ID NO 13
<211> LENGTH: 20
<212> TYPE: DNA
<213> ORGANISM: Artificial Sequence
<220> FEATURE:
<223> OTHER INFORMATION: RT primer VLk_1 for VH

<400> SEQUENCE: 13
gcgtttcatt tccagcttgg                                                20

<210> SEQ ID NO 14
<211> LENGTH: 20
<212> TYPE: DNA
<213> ORGANISM: Artificial Sequence
<220> FEATURE:
<223> OTHER INFORMATION: RT primer VLk_2 for VH

<400> SEQUENCE: 14
```

-continued gcgtttgatt tccagcttgg                                             20

<210> SEQ ID NO 15
<211> LENGTH: 20
<212> TYPE: DNA
<213> ORGANISM: Artificial Sequence
<220> FEATURE:
<223> OTHER INFORMATION: RT primer VLk_3 for VH

<400> SEQUENCE: 15
gcgttttatt tccaattttg                                            20

<210> SEQ ID NO 16
<211> LENGTH: 28
<212> TYPE: DNA
<213> ORGANISM: Artificial Sequence
<220> FEATURE:
<223> OTHER INFORMATION: T7 antisense PCR1 primer

<400> SEQUENCE: 16
gaatttaata cgactcacta tagggaga                                   28

<210> SEQ ID NO 17
<211> LENGTH: 20
<212> TYPE: DNA
<213> ORGANISM: Artificial Sequence
<220> FEATURE:
<223> OTHER INFORMATION: sense primer MmLH_AG1

<400> SEQUENCE: 17
taactgcagg tgtccactcc                                            20

<210> SEQ ID NO 18
<211> LENGTH: 20
<212> TYPE: DNA
<213> ORGANISM: Artificial Sequence
<220> FEATURE:
<223> OTHER INFORMATION: sense primer MmLH_AG2

<400> SEQUENCE: 18
cagctacagg tgtccactcc                                            20

<210> SEQ ID NO 19
<211> LENGTH: 20
<212> TYPE: DNA
<213> ORGANISM: Artificial Sequence
<220> FEATURE:
<223> OTHER INFORMATION: primer MmLH_AG3

<400> SEQUENCE: 19
tttatcaagg tgtgcattgt                                            20

<210> SEQ ID NO 20
<211> LENGTH: 20
<212> TYPE: DNA
<213> ORGANISM: Artificial Sequence
<220> FEATURE:
<223> OTHER INFORMATION: primer MmLH_AG4

<400> SEQUENCE: 20
gaactgcagg cgtccactct                                            20

<210> SEQ ID NO 21
<211> LENGTH: 20
<212> TYPE: DNA

-continued

```
<213> ORGANISM: Artificial Sequence
<220> FEATURE:
<223> OTHER INFORMATION: sense primer MmLH_AG5

<400> SEQUENCE: 21
taactgcagg tgttcactcc                                                  20

<210> SEQ ID NO 22
<211> LENGTH: 20
<212> TYPE: DNA
<213> ORGANISM: Artificial Sequence
<220> FEATURE:
<223> OTHER INFORMATION: sense primer MmLH_AG6

<400> SEQUENCE: 22
tcccaagctg tgtcctatcc                                                  20

<210> SEQ ID NO 23
<211> LENGTH: 20
<212> TYPE: DNA
<213> ORGANISM: Artificial Sequence
<220> FEATURE:
<223> OTHER INFORMATION: sense primer MmLH_AG7

<400> SEQUENCE: 23
ttccaagctg tgtcctgtcc                                                  20

<210> SEQ ID NO 24
<211> LENGTH: 20
<212> TYPE: DNA
<213> ORGANISM: Artificial Sequence
<220> FEATURE:
<223> OTHER INFORMATION: sense primer MmLH_AG8

<400> SEQUENCE: 24
cttttaaagg tattcactgt                                                  20

<210> SEQ ID NO 25
<211> LENGTH: 20
<212> TYPE: DNA
<213> ORGANISM: Artificial Sequence
<220> FEATURE:
<223> OTHER INFORMATION: sense primer MmLH_AG9

<400> SEQUENCE: 25
ttttaaaagg ggtccagtgt                                                  20

<210> SEQ ID NO 26
<211> LENGTH: 20
<212> TYPE: DNA
<213> ORGANISM: Artificial Sequence
<220> FEATURE:
<223> OTHER INFORMATION: sense primer MmLH_AG10

<400> SEQUENCE: 26
ttttaaaagg tgtccagtgt                                                  20

<210> SEQ ID NO 27
<211> LENGTH: 20
<212> TYPE: DNA
<213> ORGANISM: Artificial Sequence
<220> FEATURE:
<223> OTHER INFORMATION: sense primer MmLH_AG11

<400> SEQUENCE: 27
ttttaaatgg tatccagtgt                                                  20
```

```
<210> SEQ ID NO 28
<211> LENGTH: 20
<212> TYPE: DNA
<213> ORGANISM: Artificial Sequence
<220> FEATURE:
<223> OTHER INFORMATION: sense primer MmLH_AG12

<400> SEQUENCE: 28
ctgcccaaag tgcccaagca                                                    20

<210> SEQ ID NO 29
<211> LENGTH: 20
<212> TYPE: DNA
<213> ORGANISM: Artificial Sequence
<220> FEATURE:
<223> OTHER INFORMATION: sense primer MmLH_AG13

<400> SEQUENCE: 29
ctgcccaaag tatccaagca                                                    20

<210> SEQ ID NO 30
<211> LENGTH: 25
<212> TYPE: DNA
<213> ORGANISM: Artificial Sequence
<220> FEATURE:
<223> OTHER INFORMATION: sense primer MmLHa

<400> SEQUENCE: 30
atgrasttsk ggytmarctk grttt                                              25

<210> SEQ ID NO 31
<211> LENGTH: 26
<212> TYPE: DNA
<213> ORGANISM: Artificial Sequence
<220> FEATURE:
<223> OTHER INFORMATION: sense primer MmLHb

<400> SEQUENCE: 31
atgraatgsa sctgggtywt yctctt                                             26

<210> SEQ ID NO 32
<211> LENGTH: 29
<212> TYPE: DNA
<213> ORGANISM: Artificial Sequence
<220> FEATURE:
<223> OTHER INFORMATION: sense primer MmLHc1

<400> SEQUENCE: 32
atggactcca ggctcaattt agttttcct                                          29

<210> SEQ ID NO 33
<211> LENGTH: 26
<212> TYPE: DNA
<213> ORGANISM: Artificial Sequence
<220> FEATURE:
<223> OTHER INFORMATION: sense primer MmLHc2

<400> SEQUENCE: 33
atggctgtcy trgbgctgyt cytctg                                             26

<210> SEQ ID NO 34
<211> LENGTH: 29
<212> TYPE: DNA
<213> ORGANISM: Artificial Sequence
<220> FEATURE:
```

<223> OTHER INFORMATION: sense primer MmLHc3

<400> SEQUENCE: 34
atggvttggs tgtggamctt gcyattcct                                        29

<210> SEQ ID NO 35
<211> LENGTH: 26
<212> TYPE: DNA
<213> ORGANISM: Artificial Sequence
<220> FEATURE:
<223> OTHER INFORMATION: sense primer MmLHd1

<400> SEQUENCE: 35
atgaaatgca gctggrtyat sttctt                                           26

<210> SEQ ID NO 36
<211> LENGTH: 26
<212> TYPE: DNA
<213> ORGANISM: Artificial Sequence
<220> FEATURE:
<223> OTHER INFORMATION: sense primer MmLHd2

<400> SEQUENCE: 36
atggrcagrc ttacwtyytc attcct                                           26

<210> SEQ ID NO 37
<211> LENGTH: 26
<212> TYPE: DNA
<213> ORGANISM: Artificial Sequence
<220> FEATURE:
<223> OTHER INFORMATION: sense primer MmLHd3

<400> SEQUENCE: 37
atgatggtgt taagtcttct gtacct                                           26

<210> SEQ ID NO 38
<211> LENGTH: 26
<212> TYPE: DNA
<213> ORGANISM: Artificial Sequence
<220> FEATURE:
<223> OTHER INFORMATION: sense primer MmLHe1

<400> SEQUENCE: 38
atgggatgga gctrtatcat sytctt                                           26

<210> SEQ ID NO 39
<211> LENGTH: 23
<212> TYPE: DNA
<213> ORGANISM: Artificial Sequence
<220> FEATURE:
<223> OTHER INFORMATION: sense primer mmlhe2

<400> SEQUENCE: 39
atgaagwtgt ggbtraactg grt                                              23

<210> SEQ ID NO 40
<211> LENGTH: 25
<212> TYPE: DNA
<213> ORGANISM: Artificial Sequence
<220> FEATURE:
<223> OTHER INFORMATION: sense primer MmLHe3
<220> FEATURE:
<221> NAME/KEY: misc_feature
<222> LOCATION: (15)..(15)
<223> OTHER INFORMATION: n= I

<400> SEQUENCE: 40

-continued

```
atggratgga sckknrtctt tmtct                                      25

<210> SEQ ID NO 41
<211> LENGTH: 25
<212> TYPE: DNA
<213> ORGANISM: Artificial Sequence
<220> FEATURE:
<223> OTHER INFORMATION: sense primer MmLHf1

<400> SEQUENCE: 41
atgaacttyg ggytsagmtt grttt                                      25

<210> SEQ ID NO 42
<211> LENGTH: 25
<212> TYPE: DNA
<213> ORGANISM: Artificial Sequence
<220> FEATURE:
<223> OTHER INFORMATION: sense primer MmLHf2

<400> SEQUENCE: 42
atgtacttgg gactgagctg tgtat                                      25

<210> SEQ ID NO 43
<211> LENGTH: 23
<212> TYPE: DNA
<213> ORGANISM: Artificial Sequence
<220> FEATURE:
<223> OTHER INFORMATION: sense primer MmLHf3

<400> SEQUENCE: 43
atgagagtgc tgattctttt gtg                                        23

<210> SEQ ID NO 44
<211> LENGTH: 28
<212> TYPE: DNA
<213> ORGANISM: Artificial Sequence
<220> FEATURE:
<223> OTHER INFORMATION: sense primer MmLHf4

<400> SEQUENCE: 44
atggattttg ggctgatttt ttttattg                                   28

<210> SEQ ID NO 45
<211> LENGTH: 24
<212> TYPE: DNA
<213> ORGANISM: Artificial Sequence
<220> FEATURE:
<223> OTHER INFORMATION: VL sense primer MmLKa

<400> SEQUENCE: 45
atgragwcac akwcycaggt cttt                                       24

<210> SEQ ID NO 46
<211> LENGTH: 25
<212> TYPE: DNA
<213> ORGANISM: Artificial Sequence
<220> FEATURE:
<223> OTHER INFORMATION: VL sense primer MmLKb

<400> SEQUENCE: 46
atggagacag acacactcct gctat                                      25

<210> SEQ ID NO 47
<211> LENGTH: 29
<212> TYPE: DNA
```

-continued

```
<213> ORGANISM: Artificial Sequence
<220> FEATURE:
<223> OTHER INFORMATION: VL sense primer MmLKc

<400> SEQUENCE: 47
atggagwcag acacactsct gytatgggt                                            29

<210> SEQ ID NO 48
<211> LENGTH: 32
<212> TYPE: DNA
<213> ORGANISM: Artificial Sequence
<220> FEATURE:
<223> OTHER INFORMATION: VL sense primer MmLKd1
<220> FEATURE:
<221> NAME/KEY: misc_feature
<222> LOCATION: (27)..(27)
<223> OTHER INFORMATION: n=I

<400> SEQUENCE: 48
atgaggrccc ctgctcagwt tyttggnwtc tt                                        32

<210> SEQ ID NO 49
<211> LENGTH: 31
<212> TYPE: DNA
<213> ORGANISM: Artificial Sequence
<220> FEATURE:
<223> OTHER INFORMATION: VL sense primer MmLKd2

<400> SEQUENCE: 49
atgggcwtca agatgragtc acakwyycwg g                                         31

<210> SEQ ID NO 50
<211> LENGTH: 29
<212> TYPE: DNA
<213> ORGANISM: Artificial Sequence
<220> FEATURE:
<223> OTHER INFORMATION: VL sense primer MmLKe1

<400> SEQUENCE: 50
atgagtgtgc ycactcaggt cctggsgtt                                            29

<210> SEQ ID NO 51
<211> LENGTH: 31
<212> TYPE: DNA
<213> ORGANISM: Artificial Sequence
<220> FEATURE:
<223> OTHER INFORMATION: VL sense primer MmLKe2

<400> SEQUENCE: 51
atgttgggay cgktttyamm cttttcaatt g                                         31

<210> SEQ ID NO 52
<211> LENGTH: 28
<212> TYPE: DNA
<213> ORGANISM: Artificial Sequence
<220> FEATURE:
<223> OTHER INFORMATION: VL sense primer MmLKe3

<400> SEQUENCE: 52
atggaagccc cagctcagct tctcttcc                                             28

<210> SEQ ID NO 53
<211> LENGTH: 26
<212> TYPE: DNA
<213> ORGANISM: Artificial Sequence
<220> FEATURE:
<223> OTHER INFORMATION: VL sense primer MmLKf1
```

```
<220> FEATURE:
<221> NAME/KEY: misc_feature
<222> LOCATION: (6)..(6)
<223> OTHER INFORMATION: n= I
<220> FEATURE:
<221> NAME/KEY: misc_feature
<222> LOCATION: (12)..(12)
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n=I

<400> SEQUENCE: 53
atgagnmmkt cnmttcantt cytggg                                      26

<210> SEQ ID NO 54
<211> LENGTH: 26
<212> TYPE: DNA
<213> ORGANISM: Artificial Sequence
<220> FEATURE:
<223> OTHER INFORMATION: VL sense primer MmLKf2
<220> FEATURE:
<221> NAME/KEY: misc_feature
<222> LOCATION: (12)..(12)
<223> OTHER INFORMATION: n=I
<220> FEATURE:
<221> NAME/KEY: misc_feature
<222> LOCATION: (24)..(24)
<223> OTHER INFORMATION: n=I

<400> SEQUENCE: 54
atgakgthcy cngctcagyt yctnrg                                      26

<210> SEQ ID NO 55
<211> LENGTH: 25
<212> TYPE: DNA
<213> ORGANISM: Artificial Sequence
<220> FEATURE:
<223> OTHER INFORMATION: VL sense primer MmLKf3

<400> SEQUENCE: 55
atggtrtccw casctcagtt ccttg                                       25

<210> SEQ ID NO 56
<211> LENGTH: 27
<212> TYPE: DNA
<213> ORGANISM: Artificial Sequence
<220> FEATURE:
<223> OTHER INFORMATION: VL sense primer MmLKf4

<400> SEQUENCE: 56
atgtatatat gtttgttgtc tatttct                                     27

<210> SEQ ID NO 57
<211> LENGTH: 29
<212> TYPE: DNA
<213> ORGANISM: Artificial Sequence
<220> FEATURE:
<223> OTHER INFORMATION: VL sense primer MmLKg1

<400> SEQUENCE: 57
atgaagttgc ctgttaggct gttggtgct                                   29

<210> SEQ ID NO 58
<211> LENGTH: 29
```

```
<212> TYPE: DNA
<213> ORGANISM: Artificial Sequence
<220> FEATURE:
<223> OTHER INFORMATION: VL sense primer MmLKg2

<400> SEQUENCE: 58
atggatttwc argtgcagat twtcagctt                                    29

<210> SEQ ID NO 59
<211> LENGTH: 27
<212> TYPE: DNA
<213> ORGANISM: Artificial Sequence
<220> FEATURE:
<223> OTHER INFORMATION: VL sense primer MmLKg3

<400> SEQUENCE: 59
atggtyctya tvtccttgct gttctgg                                      27

<210> SEQ ID NO 60
<211> LENGTH: 27
<212> TYPE: DNA
<213> ORGANISM: Artificial Sequence
<220> FEATURE:
<223> OTHER INFORMATION: VL sense primer MmLKg4

<400> SEQUENCE: 60
atggtyctya tvttrctgct gctatgg                                      27

<210> SEQ ID NO 61
<211> LENGTH: 20
<212> TYPE: DNA
<213> ORGANISM: Artificial Sequence
<220> FEATURE:
<223> OTHER INFORMATION: VL sense primer LL_AG_1

<400> SEQUENCE: 61
attgctcagg ttctttctcc                                              20

<210> SEQ ID NO 62
<211> LENGTH: 20
<212> TYPE: DNA
<213> ORGANISM: Artificial Sequence
<220> FEATURE:
<223> OTHER INFORMATION: VL sense primer LL_AG_2

<400> SEQUENCE: 62
cagtcataat gtccagagga                                              20

<210> SEQ ID NO 63
<211> LENGTH: 20
<212> TYPE: DNA
<213> ORGANISM: Artificial Sequence
<220> FEATURE:
<223> OTHER INFORMATION: VL sense primer LL_AG_3

<400> SEQUENCE: 63
cagtcataat gtccagggga                                              20

<210> SEQ ID NO 64
<211> LENGTH: 20
<212> TYPE: DNA
<213> ORGANISM: Artificial Sequence
<220> FEATURE:
<223> OTHER INFORMATION: VL sense primer LL_AG_4

<400> SEQUENCE: 64
```

-continued

```
cagtcatact attcagagga                                        20

<210> SEQ ID NO 65
<211> LENGTH: 20
<212> TYPE: DNA
<213> ORGANISM: Artificial Sequence
<220> FEATURE:
<223> OTHER INFORMATION: VL sense primer LL_AG_5

<400> SEQUENCE: 65
cagtcatagt gtctaatgga                                        20

<210> SEQ ID NO 66
<211> LENGTH: 20
<212> TYPE: DNA
<213> ORGANISM: Artificial Sequence
<220> FEATURE:
<223> OTHER INFORMATION: VL sense primer LL_AG_6

<400> SEQUENCE: 66
cagtcatatt gaccaatgga                                        20

<210> SEQ ID NO 67
<211> LENGTH: 20
<212> TYPE: DNA
<213> ORGANISM: Artificial Sequence
<220> FEATURE:
<223> OTHER INFORMATION: VL sense primer LL_AG_7

<400> SEQUENCE: 67
cagtcatatt gtccagtgga                                        20

<210> SEQ ID NO 68
<211> LENGTH: 20
<212> TYPE: DNA
<213> ORGANISM: Artificial Sequence
<220> FEATURE:
<223> OTHER INFORMATION: VL sense primer LL_AG_8

<400> SEQUENCE: 68
cggtatctgg tacctgtgga                                        20

<210> SEQ ID NO 69
<211> LENGTH: 20
<212> TYPE: DNA
<213> ORGANISM: Artificial Sequence
<220> FEATURE:
<223> OTHER INFORMATION: VL sense primer LL_AG_9

<400> SEQUENCE: 69
cgagtccagc ctcaagcagt                                        20

<210> SEQ ID NO 70
<211> LENGTH: 20
<212> TYPE: DNA
<213> ORGANISM: Artificial Sequence
<220> FEATURE:
<223> OTHER INFORMATION: VL sense primer LL_AG_10

<400> SEQUENCE: 70
gaatcacagg cataatatgt                                        20

<210> SEQ ID NO 71
<211> LENGTH: 20
<212> TYPE: DNA
<213> ORGANISM: Artificial Sequence
```

-continued

```
<220> FEATURE:
<223> OTHER INFORMATION: VL sense primer LL_AG_11

<400> SEQUENCE: 71
gaatcccagg catgatatgt                                        20

<210> SEQ ID NO 72
<211> LENGTH: 20
<212> TYPE: DNA
<213> ORGANISM: Artificial Sequence
<220> FEATURE:
<223> OTHER INFORMATION: VL sense primer LL_AG_12

<400> SEQUENCE: 72
gcatgtctgg tgcctgtgca                                        20

<210> SEQ ID NO 73
<211> LENGTH: 20
<212> TYPE: DNA
<213> ORGANISM: Artificial Sequence
<220> FEATURE:
<223> OTHER INFORMATION: VL sense primer LL_AG_13

<400> SEQUENCE: 73
ggaccacggt ctcagctgtc                                        20

<210> SEQ ID NO 74
<211> LENGTH: 20
<212> TYPE: DNA
<213> ORGANISM: Artificial Sequence
<220> FEATURE:
<223> OTHER INFORMATION: VL sense primer LL_AG_14

<400> SEQUENCE: 74
ggacttcagc ctccagatgt                                        20

<210> SEQ ID NO 75
<211> LENGTH: 20
<212> TYPE: DNA
<213> ORGANISM: Artificial Sequence
<220> FEATURE:
<223> OTHER INFORMATION: VL sense primer LL_AG_15

<400> SEQUENCE: 75
ggatatcagg tgcccagtgt                                        20

<210> SEQ ID NO 76
<211> LENGTH: 20
<212> TYPE: DNA
<213> ORGANISM: Artificial Sequence
<220> FEATURE:
<223> OTHER INFORMATION: VL sense primer LL_AG_16

<400> SEQUENCE: 76
ggatccctgg agccactggg                                        20

<210> SEQ ID NO 77
<211> LENGTH: 20
<212> TYPE: DNA
<213> ORGANISM: Artificial Sequence
<220> FEATURE:
<223> OTHER INFORMATION: VL sense primer LL_AG_17

<400> SEQUENCE: 77
ggatccctgg atccactgca                                        20
```

```
<210> SEQ ID NO 78
<211> LENGTH: 20
<212> TYPE: DNA
<213> ORGANISM: Artificial Sequence
<220> FEATURE:
<223> OTHER INFORMATION: VL sense primer LL_AG_18

<400> SEQUENCE: 78
ggatctctgg agtcagtggg                                                20

<210> SEQ ID NO 79
<211> LENGTH: 20
<212> TYPE: DNA
<213> ORGANISM: Artificial Sequence
<220> FEATURE:
<223> OTHER INFORMATION: VL sense primer LL_AG_19

<400> SEQUENCE: 79
ggattcagga aaccaacggt                                                20

<210> SEQ ID NO 80
<211> LENGTH: 20
<212> TYPE: DNA
<213> ORGANISM: Artificial Sequence
<220> FEATURE:
<223> OTHER INFORMATION: VL sense primer LL_AG_20

<400> SEQUENCE: 80
ggattccagc ctccagaggt                                                20

<210> SEQ ID NO 81
<211> LENGTH: 20
<212> TYPE: DNA
<213> ORGANISM: Artificial Sequence
<220> FEATURE:
<223> OTHER INFORMATION: VL sense primer LL_AG_21

<400> SEQUENCE: 81
ggattcctgc ttccagcagt                                                20

<210> SEQ ID NO 82
<211> LENGTH: 20
<212> TYPE: DNA
<213> ORGANISM: Artificial Sequence
<220> FEATURE:
<223> OTHER INFORMATION: VL sense primer LL_AG_22

<400> SEQUENCE: 82
ggattcggga aaccaacggt                                                20

<210> SEQ ID NO 83
<211> LENGTH: 20
<212> TYPE: DNA
<213> ORGANISM: Artificial Sequence
<220> FEATURE:
<223> OTHER INFORMATION: VL sense primer LL_AG_23

<400> SEQUENCE: 83
ggatttcagc ctccacaggt                                                20

<210> SEQ ID NO 84
<211> LENGTH: 20
<212> TYPE: DNA
<213> ORGANISM: Artificial Sequence
<220> FEATURE:
<223> OTHER INFORMATION: VL sense primer LL_AG_24
```

<400> SEQUENCE: 84
ggctccaagg catgagctgt                                                      20

<210> SEQ ID NO 85
<211> LENGTH: 20
<212> TYPE: DNA
<213> ORGANISM: Artificial Sequence
<220> FEATURE:
<223> OTHER INFORMATION: VL sense primer LL_AG_25

<400> SEQUENCE: 85
ggcttcatgg tgctcagtgt                                                      20

<210> SEQ ID NO 86
<211> LENGTH: 20
<212> TYPE: DNA
<213> ORGANISM: Artificial Sequence
<220> FEATURE:
<223> OTHER INFORMATION: VL sense primer LL_AG_26

<400> SEQUENCE: 86
ggcttacaga cgcaggatgt                                                      20

<210> SEQ ID NO 87
<211> LENGTH: 20
<212> TYPE: DNA
<213> ORGANISM: Artificial Sequence
<220> FEATURE:
<223> OTHER INFORMATION: VL sense primer LL_AG_27

<400> SEQUENCE: 87
ggcttacaga tgccagatgt                                                      20

<210> SEQ ID NO 88
<211> LENGTH: 20
<212> TYPE: DNA
<213> ORGANISM: Artificial Sequence
<220> FEATURE:
<223> OTHER INFORMATION: VL sense primer LL_AG_28

<400> SEQUENCE: 88
gggtatctgg tacctgtggg                                                      20

<210> SEQ ID NO 89
<211> LENGTH: 20
<212> TYPE: DNA
<213> ORGANISM: Artificial Sequence
<220> FEATURE:
<223> OTHER INFORMATION: VL sense primer LL_AG_29

<400> SEQUENCE: 89
gggtatctgg tgcctgtgca                                                      20

<210> SEQ ID NO 90
<211> LENGTH: 20
<212> TYPE: DNA
<213> ORGANISM: Artificial Sequence
<220> FEATURE:
<223> OTHER INFORMATION: VL sense primer LL_AG_30

<400> SEQUENCE: 90
gggttccagg ttccactggt                                                      20

<210> SEQ ID NO 91

-continued

```
<211> LENGTH: 20
<212> TYPE: DNA
<213> ORGANISM: Artificial Sequence
<220> FEATURE:
<223> OTHER INFORMATION: VL sense primer LL_AG_31

<400> SEQUENCE: 91
ggttatatgg tgctgatggg                                              20

<210> SEQ ID NO 92
<211> LENGTH: 20
<212> TYPE: DNA
<213> ORGANISM: Artificial Sequence
<220> FEATURE:
<223> OTHER INFORMATION: VL sense primer LL_AG_32

<400> SEQUENCE: 92
ggttcccagg tgccagatgt                                              20

<210> SEQ ID NO 93
<211> LENGTH: 20
<212> TYPE: DNA
<213> ORGANISM: Artificial Sequence
<220> FEATURE:
<223> OTHER INFORMATION: VL sense primer LL_AG_33

<400> SEQUENCE: 93
ggttgtctgg tgttgaagga                                              20

<210> SEQ ID NO 94
<211> LENGTH: 20
<212> TYPE: DNA
<213> ORGANISM: Artificial Sequence
<220> FEATURE:
<223> OTHER INFORMATION: VL sense primer LL_AG_34

<400> SEQUENCE: 94
ggtttccagg tatcagatgt                                              20

<210> SEQ ID NO 95
<211> LENGTH: 20
<212> TYPE: DNA
<213> ORGANISM: Artificial Sequence
<220> FEATURE:
<223> OTHER INFORMATION: VL sense primer LL_AG_35

<400> SEQUENCE: 95
ggtttccagg tgcaagatgt                                              20

<210> SEQ ID NO 96
<211> LENGTH: 20
<212> TYPE: DNA
<213> ORGANISM: Artificial Sequence
<220> FEATURE:
<223> OTHER INFORMATION: VL sense primer LL_AG_36

<400> SEQUENCE: 96
ggtttgcagg tggtaaatgt                                              20

<210> SEQ ID NO 97
<211> LENGTH: 20
<212> TYPE: DNA
<213> ORGANISM: Artificial Sequence
<220> FEATURE:
<223> OTHER INFORMATION: VL sense primer LL_AG_37

<400> SEQUENCE: 97
```

-continued ggtttttagg tgccagatgt                                                    20

<210> SEQ ID NO 98
<211> LENGTH: 20
<212> TYPE: DNA
<213> ORGANISM: Artificial Sequence
<220> FEATURE:
<223> OTHER INFORMATION: VL sense primer LL_AG_38

<400> SEQUENCE: 98
gtgtcacagt gtcaaaggga                                                    20

<210> SEQ ID NO 99
<211> LENGTH: 20
<212> TYPE: DNA
<213> ORGANISM: Artificial Sequence
<220> FEATURE:
<223> OTHER INFORMATION: VL sense primer LL_AG_39

<400> SEQUENCE: 99
gtgtctctga ttctagggca                                                    20

<210> SEQ ID NO 100
<211> LENGTH: 20
<212> TYPE: DNA
<213> ORGANISM: Artificial Sequence
<220> FEATURE:
<223> OTHER INFORMATION: VL sense primer LL_AG_40

<400> SEQUENCE: 100
gtgtgtctgg tgctcatggg                                                    20

<210> SEQ ID NO 101
<211> LENGTH: 20
<212> TYPE: DNA
<213> ORGANISM: Artificial Sequence
<220> FEATURE:
<223> OTHER INFORMATION: VL sense primer LL_AG_41

<400> SEQUENCE: 101
gttttcaagg taccagatat                                                    20

<210> SEQ ID NO 102
<211> LENGTH: 20
<212> TYPE: DNA
<213> ORGANISM: Artificial Sequence
<220> FEATURE:
<223> OTHER INFORMATION: VL sense primer LL_AG_42

<400> SEQUENCE: 102
gttttcaagg taccagatgt                                                    20

<210> SEQ ID NO 103
<211> LENGTH: 65
<212> TYPE: DNA
<213> ORGANISM: Artificial Sequence
<220> FEATURE:
<223> OTHER INFORMATION: Illumina Index Antisense primer
<220> FEATURE:
<221> NAME/KEY: misc_feature
<222> LOCATION: (25)..(31)
<223> OTHER INFORMATION: n = a or g or c or t/u or other modified
      nucleotide

<400> SEQUENCE: 103
caagcagaag acggcatacg agatnnnnnn ngtgactgga gttcagacgt gtgctcttcc       60

-continued gatct                                                                                                                65

<210> SEQ ID NO 104
<211> LENGTH: 78
<212> TYPE: DNA
<213> ORGANISM: Artificial Sequence
<220> FEATURE:
<223> OTHER INFORMATION: VH sense primer VHs1

<400> SEQUENCE: 104
aatgatacgg cgaccaccga gatctacact ctttccctac acgacgctct tccgatctga            60
tgtgaagctt caggagtc                                                                                  78

<210> SEQ ID NO 105
<211> LENGTH: 78
<212> TYPE: DNA
<213> ORGANISM: Artificial Sequence
<220> FEATURE:
<223> OTHER INFORMATION: VH sense primer VHs2

<400> SEQUENCE: 105
aatgatacgg cgaccaccga gatctacact ctttccctac acgacgctct tccgatctca            60
ggtgcagctg aaggagtc                                                                                  78

<210> SEQ ID NO 106
<211> LENGTH: 78
<212> TYPE: DNA
<213> ORGANISM: Artificial Sequence
<220> FEATURE:
<223> OTHER INFORMATION: VH sense primer VHs3

<400> SEQUENCE: 106
aatgatacgg cgaccaccga gatctacact ctttccctac acgacgctct tccgatctca            60
ggtgcagctg aagcagtc                                                                                  78

<210> SEQ ID NO 107
<211> LENGTH: 78
<212> TYPE: DNA
<213> ORGANISM: Artificial Sequence
<220> FEATURE:
<223> OTHER INFORMATION: VH sense primer VHs4

<400> SEQUENCE: 107
aatgatacgg cgaccaccga gatctacact ctttccctac acgacgctct tccgatctca            60
ggttactctg aaagagtc                                                                                  78

<210> SEQ ID NO 108
<211> LENGTH: 79
<212> TYPE: DNA
<213> ORGANISM: Artificial Sequence
<220> FEATURE:
<223> OTHER INFORMATION: VH sense primer VHs5

<400> SEQUENCE: 108
aatgatacgg cgaccaccga gatctacact ctttccctac acgacgctct tccgatctga            60
ggtccagctg caacaatct                                                                                79

<210> SEQ ID NO 109
<211> LENGTH: 78
<212> TYPE: DNA
<213> ORGANISM: Artificial Sequence
<220> FEATURE:

<223> OTHER INFORMATION: VH sense primer VHs6

<400> SEQUENCE: 109
aatgatacgg cgaccaccga gatctacact ctttccctac acgacgctct tccgatctga      60
ggtccagctg cagcagtc                                                      78

<210> SEQ ID NO 110
<211> LENGTH: 79
<212> TYPE: DNA
<213> ORGANISM: Artificial Sequence
<220> FEATURE:
<223> OTHER INFORMATION: VH sense primer VHs7

<400> SEQUENCE: 110
aatgatacgg cgaccaccga gatctacact ctttccctac acgacgctct tccgatctca      60
ggtccaactg cagcagcct                                                     79

<210> SEQ ID NO 111
<211> LENGTH: 78
<212> TYPE: DNA
<213> ORGANISM: Artificial Sequence
<220> FEATURE:
<223> OTHER INFORMATION: VH sense primer VHs8

<400> SEQUENCE: 111
aatgatacgg cgaccaccga gatctacact ctttccctac acgacgctct tccgatctga      60
ggtgaagctg gtggagtc                                                      78

<210> SEQ ID NO 112
<211> LENGTH: 78
<212> TYPE: DNA
<213> ORGANISM: Artificial Sequence
<220> FEATURE:
<223> OTHER INFORMATION: VH sense primer VHs9

<400> SEQUENCE: 112
aatgatacgg cgaccaccga gatctacact ctttccctac acgacgctct tccgatctga      60
ggtgaagctg gtggaatc                                                      78

<210> SEQ ID NO 113
<211> LENGTH: 78
<212> TYPE: DNA
<213> ORGANISM: Artificial Sequence
<220> FEATURE:
<223> OTHER INFORMATION: VH sense primer VHs10

<400> SEQUENCE: 113
aatgatacgg cgaccaccga gatctacact ctttccctac acgacgctct tccgatctga      60
tgtgaacttg gaagtgtc                                                      78

<210> SEQ ID NO 114
<211> LENGTH: 78
<212> TYPE: DNA
<213> ORGANISM: Artificial Sequence
<220> FEATURE:
<223> OTHER INFORMATION: VH sense primer VHs11

<400> SEQUENCE: 114
aatgatacgg cgaccaccga gatctacact ctttccctac acgacgctct tccgatctga      60
ggtccagctg caacagtc                                                      78

<210> SEQ ID NO 115
<211> LENGTH: 78
<212> TYPE: DNA
<213> ORGANISM: Artificial Sequence
<220> FEATURE:
<223> OTHER INFORMATION: VH sense primer VHs12

<400> SEQUENCE: 115
aatgatacgg cgaccaccga gatctacact ctttccctac acgacgctct tccgatctga    60
ggtgcagctg gaggagtc                                                  78

<210> SEQ ID NO 116
<211> LENGTH: 79
<212> TYPE: DNA
<213> ORGANISM: Artificial Sequence
<220> FEATURE:
<223> OTHER INFORMATION: VL sense primer VKs1

<400> SEQUENCE: 116
aatgatacgg cgaccaccga gatctacact ctttccctac acgacgctct tccgatctga    60
tattgtgatg acgcaggct                                                 79

<210> SEQ ID NO 117
<211> LENGTH: 76
<212> TYPE: DNA
<213> ORGANISM: Artificial Sequence
<220> FEATURE:
<223> OTHER INFORMATION: VL sense primer VKs2

<400> SEQUENCE: 117
aatgatacgg cgaccaccga gatctacact ctttccctac acgacgctct tccgatctga    60
tattgtgata acccag                                                    76

<210> SEQ ID NO 118
<211> LENGTH: 79
<212> TYPE: DNA
<213> ORGANISM: Artificial Sequence
<220> FEATURE:
<223> OTHER INFORMATION: VL sense primer VKs3

<400> SEQUENCE: 118
aatgatacgg cgaccaccga gatctacact ctttccctac acgacgctct tccgatctga    60
cattgtgctg acccaatct                                                 79

<210> SEQ ID NO 119
<211> LENGTH: 79
<212> TYPE: DNA
<213> ORGANISM: Artificial Sequence
<220> FEATURE:
<223> OTHER INFORMATION: VL sense primer VKs4

<400> SEQUENCE: 119
aatgatacgg cgaccaccga gatctacact ctttccctac acgacgctct tccgatctga    60
cattgtgatg acccagtct                                                 79

<210> SEQ ID NO 120
<211> LENGTH: 79
<212> TYPE: DNA
<213> ORGANISM: Artificial Sequence
<220> FEATURE:
<223> OTHER INFORMATION: VL sense primer VKs5

<400> SEQUENCE: 120

-continued

```
aatgatacgg cgaccaccga gatctacact ctttccctac acgacgctct tccgatctga      60
tattgtgcta actcagtct                                                    79

<210> SEQ ID NO 121
<211> LENGTH: 79
<212> TYPE: DNA
<213> ORGANISM: Artificial Sequence
<220> FEATURE:
<223> OTHER INFORMATION: VL sense primer VKs6

<400> SEQUENCE: 121
aatgatacgg cgaccaccga gatctacact ctttccctac acgacgctct tccgatctga      60
tatccagatg acacagact                                                    79

<210> SEQ ID NO 122
<211> LENGTH: 79
<212> TYPE: DNA
<213> ORGANISM: Artificial Sequence
<220> FEATURE:
<223> OTHER INFORMATION: VL sense primer VKs7

<400> SEQUENCE: 122
aatgatacgg cgaccaccga gatctacact ctttccctac acgacgctct tccgatctga      60
catccagctg actcagtct                                                    79

<210> SEQ ID NO 123
<211> LENGTH: 79
<212> TYPE: DNA
<213> ORGANISM: Artificial Sequence
<220> FEATURE:
<223> OTHER INFORMATION: VL sense primer VKs8

<400> SEQUENCE: 123
aatgatacgg cgaccaccga gatctacact ctttccctac acgacgctct tccgatctca      60
aattgttctc acccagtct                                                    79

<210> SEQ ID NO 124
<211> LENGTH: 79
<212> TYPE: DNA
<213> ORGANISM: Artificial Sequence
<220> FEATURE:
<223> OTHER INFORMATION: VL sense primer VKs9

<400> SEQUENCE: 124
aatgatacgg cgaccaccga gatctacact ctttccctac acgacgctct tccgatctga      60
tgttttgatg acccaaact                                                    79

<210> SEQ ID NO 125
<211> LENGTH: 20
<212> TYPE: DNA
<213> ORGANISM: Artificial Sequence
<220> FEATURE:
<223> OTHER INFORMATION: primer RT_VLk

<400> SEQUENCE: 125
gatggtggga agatggatac                                                   20

<210> SEQ ID NO 126
<211> LENGTH: 58
<212> TYPE: DNA
<213> ORGANISM: Artificial Sequence
<220> FEATURE:
<223> OTHER INFORMATION: sense primer used in PCR3
```

<400> SEQUENCE: 126
aatgatacgg cgaccaccga gatctacact ctttccctac acgacgctct tccgatct          58

<210> SEQ ID NO 127
<211> LENGTH: 24
<212> TYPE: DNA
<213> ORGANISM: Artificial Sequence
<220> FEATURE:
<223> OTHER INFORMATION: antisense primer used in PCR3

<400> SEQUENCE: 127
caagcagaag acggcatacg agat                                               24

<210> SEQ ID NO 128
<211> LENGTH: 21
<212> TYPE: PRT
<213> ORGANISM: Artificial Sequence
<220> FEATURE:
<223> OTHER INFORMATION: CDR3

<400> SEQUENCE: 128

Cys Ala Arg Asp Trp Ser Arg Ser Trp Tyr Leu Ala Pro Asn Gly Pro
1               5                   10                  15

Asp Leu Asp Tyr Trp
            20

<210> SEQ ID NO 129
<211> LENGTH: 12
<212> TYPE: PRT
<213> ORGANISM: Artificial Sequence
<220> FEATURE:
<223> OTHER INFORMATION: CDR3

<400> SEQUENCE: 129

Cys Cys Ser Tyr Ala Gly Gly Ser Thr Leu Val Phe
1               5                   10

<210> SEQ ID NO 130
<211> LENGTH: 18
<212> TYPE: PRT
<213> ORGANISM: Artificial Sequence
<220> FEATURE:
<223> OTHER INFORMATION: CDR3

<400> SEQUENCE: 130

Cys Ala Arg Gly Gly Lys Ser Asp Asp Gly Asn Phe Arg Tyr Phe Asp
1               5                   10                  15

His Trp

<210> SEQ ID NO 131
<211> LENGTH: 13
<212> TYPE: PRT
<213> ORGANISM: Artificial Sequence
<220> FEATURE:
<223> OTHER INFORMATION: CDR3

<400> SEQUENCE: 131

Cys Gln Gln Arg Ser Ser Trp Pro Pro Gly Trp Thr Phe
1               5                   10

<210> SEQ ID NO 132
<211> LENGTH: 20
<212> TYPE: PRT
<213> ORGANISM: Artificial Sequence

<220> FEATURE:
<223> OTHER INFORMATION: CDR3

<400> SEQUENCE: 132

Cys Ala Lys Ser Phe Gly Phe Gly Gly Val Ile Val Ile Gly Gly Tyr
1               5                   10                  15

Phe Leu His Trp
            20

<210> SEQ ID NO 133
<211> LENGTH: 11
<212> TYPE: PRT
<213> ORGANISM: Artificial Sequence
<220> FEATURE:
<223> OTHER INFORMATION: CDR3

<400> SEQUENCE: 133

Cys Gln Gln Tyr Asp Asn Leu Pro Leu Thr Phe
1               5                   10

<210> SEQ ID NO 134
<211> LENGTH: 17
<212> TYPE: PRT
<213> ORGANISM: Artificial Sequence
<220> FEATURE:
<223> OTHER INFORMATION: CDR3

<400> SEQUENCE: 134

Cys Ala Arg His Lys Thr Thr Ser Gly Trp Tyr Ser Pro Leu Asp Tyr
1               5                   10                  15

Trp

<210> SEQ ID NO 135
<211> LENGTH: 11
<212> TYPE: PRT
<213> ORGANISM: Artificial Sequence
<220> FEATURE:
<223> OTHER INFORMATION: CDR3

<400> SEQUENCE: 135

Cys Gln Gln Tyr Ser Gly Ser Val Trp Thr Phe
1               5                   10

<210> SEQ ID NO 136
<211> LENGTH: 18
<212> TYPE: PRT
<213> ORGANISM: Artificial Sequence
<220> FEATURE:
<223> OTHER INFORMATION: CDR3

<400> SEQUENCE: 136

Cys Ala Arg Gly Val Lys Ala Ala Gly Arg Thr Pro Asn Trp Phe Gly
1               5                   10                  15

Pro Trp

<210> SEQ ID NO 137
<211> LENGTH: 14
<212> TYPE: PRT
<213> ORGANISM: Artificial Sequence
<220> FEATURE:
<223> OTHER INFORMATION: CDR3

<400> SEQUENCE: 137

Cys Gln Ser Tyr Asp Ser Ser Leu Ser Gly His Val Val Phe
1               5                   10

-continued

```
<210> SEQ ID NO 138
<211> LENGTH: 17
<212> TYPE: PRT
<213> ORGANISM: Artificial Sequence
<220> FEATURE:
<223> OTHER INFORMATION: CDR3

<400> SEQUENCE: 138

Cys Ala Arg Glu Val Ser Ala Asp Ile Leu Thr Gly Tyr Tyr Asp Tyr
1               5                   10                  15

Trp

<210> SEQ ID NO 139
<211> LENGTH: 11
<212> TYPE: PRT
<213> ORGANISM: Artificial Sequence
<220> FEATURE:
<223> OTHER INFORMATION: CDR3

<400> SEQUENCE: 139

Cys Gln His Tyr Asp Asn Leu Pro Pro Thr Phe
1               5                   10
```

METHOD FOR TRANSCRIPTOME ANALYSIS OF SINGLE CELLS

CROSS REFERENCE TO RELATED APPLICATIONS

This application claims the benefit of priority under 35 U.S.C. § 371 of International Application No. PCT/EP2016/080341, filed on Dec. 8, 2016, which claims the benefit of the filing date of European Application No. 16305783.9, filed on Jun. 28, 2016, and claims the benefit of U.S. Provisional Application No. 62/264,414, which was filed on Dec. 8, 2015. The content of these earlier filed applications is hereby incorporated by reference herein in its entirety.

The present invention concerns a method for capturing and barcoding nucleic acid from single cells, a plurality of compartments, in particular a plurality of microfluidic droplets and a method for preparing a plurality of microfluidic droplets.

There is a long-felt yet unmet need in the art for rapid isolation and sequencing from one or more transcripts up to the whole transcriptome present in a single cell. The need is particularly significant in the field of antibody drug discovery, immune cell and tumor cell profiling.

Global studies of single cells have been enabled by a tremendous increase in the sensitivity of scientific instruments and an ever-growing automation of all steps from sample preparation to data analysis. In the state of the art, different methods are so far described to capture single cell nucleic acids and to barcode said nucleic acids.

However most of said protocols still require large reaction volumes, or multiple, time consuming steps. High volumes have the disadvantage that they require larger amounts of cost expensive enzymes and nucleotides that are needed for the reverse transcription (RT) of RNAs.

Reducing the reaction volume and in the meantime obtaining a reliable and efficient reverse transcription is therefore an important need in the art.

In the state of the art, different authors addressed this problem and tried to reduce reaction volume in order to increase the throughput.

White et al. (Proc Natl Acad Sci USA. 2011 Aug. 23; 108(34):13999-4004) describe a microfluidic device capable of performing RT-qPCR measurements of gene expression from hundreds of single cells per run, executing single-cell processing, including cell capture, cell lysis, reverse transcription, and quantitative PCR. However, incited to try smaller reaction volumes, White et al. (Proc Natl Acad Sci USA. 2011 Aug. 23; 108(34):13999-4004) performed 300 parallel RT-qPCR and demonstrated that RT is inhibited in volumes that are smaller than 5 nL in the reaction conditions tested. The researchers thus performed the RT reaction in 67 nL per cell and further claimed that the combination of RT and qPCR in a single reaction precludes large-scale transcriptome analysis and/or unbiased amplification.

Furthermore, a method using a simple axisymmetric flow-focusing device has been described for single cell mRNA capture by DeKosky et al. (Nat Med. 2015 January; 21(1):86-91). The RT and PCR reaction of the method take place in an emulsion. This process has proven to be efficient, yet requiring performing sequential 3 steps process.

Along the same line, Eastburn et al. (Anal Chem. 2013 Aug. 20; 85(16):8016-21) performed RT in small droplet volume, yet in a time consuming 3-4 steps process. They mentioned also RT inhibition in small volume from cell proteinase. To overcome this problem, they treat the cells with proteinase, dilute cell lysate, split drops, and pico-inject RT-PCR reagents.

Rotem et al. (PLoS One. 2015 May 22; 10(5):e0116328) encapsulate oligo in droplet population and fuse them to droplet containing cells while pico-injecting the RT enzymes and buffers. This 3 step process produces ~100 pL droplets allowing encapsulation of 100.000 cells in 3 h. Although this method relies on single cell cDNA labeling, the transcriptomic sequence data comes from an aggregate of multiple phenotypically and genotypically uncorrelated cells.

Macosko et al. (Cell. 2015 May 21; 161(5):1202-14) used droplet-based microfluidics to encapsulate cells together with lysis reagents and barcoded beads to capture mRNA in 1 nL drops. The beads are then recovered to perform, off chip, the conversion of the mRNA captured on beads into cDNA. The third step is then devoted to library preparation and amplification.

The international patent application WO2015/164212 refers to a method for encapsulating and barcoding single cell nucleic acids. WO2015/164212 discloses that RT of mRNA is strongly inhibited in volumes that are smaller than 3 nL (Example 4 of WO2015/164212 and Georgio G. et al. Nat Biotechnol. 2014 February; 32(2):158-68).

Contrary to this, the inventors succeeded in developing a single-step, reverse transcription of single cell mRNA wherein barcoded cDNA is produced in volumes smaller than 3 nL. This method consists of a single step to obtain the cDNA and has an increased throughput (factor 5-10 times; 100.000 cells encapsulated with barcoded primers in 1 h) and reduced costs due to the reduced volume. The inventors thus established experimental conditions leading to efficient cDNA synthesis in micro reactors having a volume of less than 3 nL.

DETAILED DESCRIPTION OF THE INVENTION

Unless otherwise defined, scientific and technical terms used in connection with the disclosure shall have the meanings that are commonly understood by those of ordinary skill in the art.

Further, unless otherwise required by context, singular terms shall include pluralities and plural terms shall include the singular.

Generally, nomenclatures utilized in connection with, and techniques of, cell and tissue culture, molecular biology, and protein and oligo- or polynucleotide chemistry and hybridization described herein are those well-known and commonly used in the art.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The practice of the disclosure will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames &

S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

The term "nucleic acid" as herein used generally refers to at least one molecule or strand of DNA, RNA, miRNA or a derivative or mimic thereof, comprising at least one nucleobase, such as, for example, a naturally occurring purine or pyrimidine base found in DNA (e.g., adenine "A," guanine "G," thymine "T," and cytosine "C") or RNA (e.g. A, G, uracil "U," and C). The term "nucleic acid" encompasses the term "oligonucleotide".

"RNA" herein refers to functional RNA, such as, without limitation to the examples, mRNA, tRNA, rRNA, catalytic RNA, siRNA, miRNA, antisense RNA, lncRNA and piRNA.

As it will be understood by those skilled in the art, the depiction of a single strand also defines the sequence of the complementary strand. Thus, a nucleic acid also encompasses the complementary strand of a depicted single strand. The term nucleic acid thus encompasses complementary DNA. As it will also be appreciated by those skilled in the art, many variants of a nucleic acid may be used for the same purpose as a given nucleic acid. Thus, a nucleic acid also encompasses substantially identical nucleic acids and complements thereof. As it will also be understood by those skilled in the art, a single strand nucleic acid, such as, a primer, may hybridize to the target sequence under hybridization conditions, preferably stringent hybridization conditions. Thus, a nucleic acid also encompasses a primer that hybridizes under hybridization conditions to a target sequence.

The term "oligonucleotide" refers to at least one molecule of about 3 to about 200 nucleobases in length.

These definitions refer to at least one single-stranded molecule, but in some embodiments encompass also at least one additional strand that is partially, substantially or fully complementary to the at least one single-stranded molecule. Accordingly, in some embodiments said definitions refer to double stranded molecules.

Thus, in one embodiment, a nucleic acid refers to at least one double-stranded molecule that comprises one or more complementary strand(s) or "complement(s)" of a particular sequence comprising a strand of the molecule.

"Gene" as used herein may be a genomic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA, antisense RNA, lncRNA and piRNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

The term "stringent condition" or "high stringency condition" as used herein corresponds to conditions that are suitable to produce binding pairs between nucleic acids having a determined level of complementarity, while being unsuitable to the formation of binding pairs between nucleic acids displaying a complementarity inferior to said determined level. Stringent conditions are the combination of both hybridization and wash conditions and are sequence dependent. These conditions may be modified according to methods known from those skilled in the art (Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, high stringency conditions are selected to be about 5° C. lower than the thermal melting point (Tm), preferably at a temperature close to the Tm of perfectly base-paired duplexes (Andersen, Nucleic acid Hybridization, Springer, 1999, p. 54). Hybridization procedures are well known in the art and are described for example in Ausubel, F. M., Brent, R., Kingston, R. E., Moore, D. D., Seidman, J. G., Smith, J. A., Struhl, K. eds. (1998) Current protocols in molecular biology. V. B. Chanda, series ed. New York: John Wiley & Sons.

High stringency conditions typically involve hybridizing at about 50° C. to about 68° C., wherein said temperature typically corresponds to the highest melting temperature $T_M$ of the nucleic acid to be hybridized with a target sequence, for example, in 5×SSC/5×Denhardt's solution/1.0% SDS, and washing in 0.2×SSC/0.1% SDS at about 60° C. to about 68° C.

For instance, in context with the present invention the primer sequence comprised in the oligonucleotide typically hybridizes with a complementary nucleic acid, for example a complementary RNA sequence, cDNA or DNA sequence, at about 50° C. to about 68° C. in a compartment (in particular in a droplet), or in a plurality of compartments (in particular in a plurality of droplets) further comprising a lysing composition and a reverse transcription composition, as defined herein below.

The term "antibody" refers to immunoglobulin molecules and immunologically active portions of immunoglobulin molecules, i.e., molecules that contain an antigen binding site which immunospecifically binds an antigen. As such, the term antibody encompasses not only whole antibody molecules, but also antibody fragments as well as variants of antibodies, including derivatives such as humanized antibodies. In certain conventional antibodies, two heavy chains are linked to each other by disulfide bonds and each heavy chain is linked to a light chain by a disulfide bond. There are two types of light chain, lambda (λ) and kappa (κ). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non hypervariable or framework regions (FR) influence the overall domain structure and hence the combining site. Complementarity determining regions (CDRs) refer to amino acid sequences which, together, define the binding affinity and specificity of the natural Fv region of a native immunoglobulin binding-site. The light and heavy chains of an immunoglobulin each have three CDRs, designated L-CDR1, L-CDR2, L-CDR3 and H-CDR1, H-CDR2, H-CDR3, respectively. Therefore, an antigen-binding site includes six CDRs, comprising the CDR set from each of a heavy and a light chain V region. Framework Regions (FRs) refer to amino acid sequences interposed between CDRs, i.e. to those portions of immunoglobulin light and heavy chain variable regions that are relatively conserved among different immunoglobulins in a single species, as defined by Kabat, et al. (Sequences of Proteins of Immunological Interest (National Institutes of Health, Bethesda, Md., 1991).

An "antibody fragment" comprises a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

The term antibody further denotes single chain antibodies, for instance Camelidae antibodies, or nanobodies or $V_{HH}$.

The term "T-cell receptor" herein refers to an antigen-recognition molecule present on the surface of T cells (i.e., T lymphocytes). This definition expressly includes the understanding of the term as known in the art, and includes, for example, a receptor that comprises or consists of a disulfide-linked heterodimer of the highly variable alpha or beta chains expressed at the cell membrane as a complex with the invariant CD3 chains, or a receptor that comprises or consists of variable gamma and delta chains expressed at the cell membrane as a complex with CD3 on a subset of T-cells.

"Antibody genes" and "T-cell receptor genes" undergo a unique mechanism of genetic recombination, called V(D)J recombination, that occurs only in developing lymphocytes during the early stages of T and B cell maturation. It further involves somatic recombination, and results in the highly diverse repertoire of antibodies/immunoglobulins (Igs) and T cell receptors (TCRs) found on B cells and T cells, respectively.

Method for Capturing and Barcoding Single Cell Nucleic Acid

"Capturing" herein refers to hybridizing single cell nucleic acid(s) to primer(s), in a compartment, in particular in a droplet, or in a plurality of compartments, in particular in a plurality of droplets.

"Barcoding" herein refers to adding a genetic sequence, a so-called barcode sequence as further defined herein below, to a nucleic acid which allows distinguishing said barcoded nucleic acid from a nucleic acid having another added genetic sequence, i.e. another unique barcode sequence.

The inventors have developed a single-step, reverse transcription of single cell mRNA, wherein a single cell is captured in volumes less than 3 nL, and preferably in sub-nanoliter volumes of a droplet, and barcoded cDNA is produced with an increased throughput (factor 5-10 times; 100.000 cells encapsulated with barcoded primers in 1 h) and reduced costs. The inventors established experimental conditions leading to efficient cDNA synthesis micro reactors of less than 3 nL, independent of cell size and shape.

Accordingly, the present invention refers to a method for capturing and barcoding single cell nucleic acid comprising:

a) providing a plurality of cells contained within a plurality of compartments, at least some of the compartments comprising a single cell, a reverse transcriptase and at least one type of an oligonucleotide, wherein the at least one type of oligonucleotide comprises a barcode sequence and a primer sequence, wherein each different primer sequence defines a different oligonucleotide type, and wherein the compartments of the plurality of the compartments contain one or more barcode sequences distinguishable from barcode sequences contained in other compartments of the plurality of compartments;

b) lysing at least some of the cells within the compartments to release nucleic acids from the cells;

c) hybridizing at least some of the released nucleic acids to said oligonucleotide in at least some of the compartments;

d) reverse transcribing the released nucleic acids hybridized to said oligonucleotide using the primer sequence in at least some of the compartments;

wherein the plurality of compartments has a volume of less than 3 nL; and preferably wherein the concentration of each type of oligonucleotide in the microfluidic droplets is at least 100 nM.

"Compartment", also referred to as "container", herein refers, for example, to a plate, well, tube, channel, nano well, nano drop, nano tube, or nano channel.

In a preferred embodiment in context of the invention, a compartment is a droplet, more preferably a microfluidic droplet.

Accordingly, in a preferred embodiment, a plurality of compartments is a plurality of droplets, more preferably a plurality of microfluidic droplets.

In some embodiments, the at least one type of oligonucleotide is introduced into the compartments by initially binding the at least one type of oligonucleotide to a particle, then subsequently releasing them from the particle after the particle has been incorporated into a compartment.

In certain embodiments of the invention, binding the at least one type of oligonucleotide initially to the particle facilitates the introduction of only one type of oligonucleotide into each compartment.

According to the above, in one embodiment, step a) further comprises providing a plurality of particles contained within said plurality of compartments, and wherein at least some of the compartments further comprise a particle.

In a related embodiment, the at least one type of an oligonucleotide is bound to said particle.

Accordingly, in a preferred embodiment, the invention refers to a method for capturing and barcoding single cell nucleic acid comprising:

a) providing a plurality of cells and a plurality of particles contained within a plurality of compartments, at least some of the compartments comprising a single cell, a reverse transcriptase and a particle comprising at least one type of an oligonucleotide optionally bound thereto, wherein the at least one type of oligonucleotide comprises a barcode sequence and a primer sequence, wherein each different primer sequence defines a different oligonucleotide type, and wherein the compartments of the plurality of compartments contain one or more barcode sequences distinguishable from barcode sequences contained in other compartments of the plurality of compartments;

b) lysing at least some of the cells within the compartments to release nucleic acids from the cells;

c) hybridizing at least some of the released nucleic acids to said oligonucleotide in at least some of the compartments;

d) reverse transcribing the released nucleic acids hybridized to said oligonucleotide using the primer sequence in at least some of the compartments;

wherein the plurality of compartments has a volume of less than 3 nL; and preferably wherein the concentration of each type of oligonucleotide in the compartments containing a particle is at least 100 nM.

The "particle" in context of the present invention refers to a microparticle.

In one embodiment the particle is a hydrogel particle, a polymeric particle or a magnetic particle.

The particle may have irregular or regular shape. For example, the particle can be spherical, ellipsoidal, or cubic.

In one embodiment, the particle(s) and the cell(s) may be introduced into the compartment(s) or encapsulated within the compartments simultaneously or sequentially, in any suitable order.

In one preferred embodiment, the particle(s) and the cell(s) may be encapsulated within the droplet(s) simultaneously or sequentially, in any suitable order.

In some embodiments, the particle in context of the present invention is a hydrogel particle.

"Hydrogel particles" are for example described in the International Patent Application No. WO 2008/109176, entitled "Assay and other reactions involving droplets". Examples of hydrogels include, but are not limited to agarose, poly(ethylene glycol) diacrylate, or acrylamide-based gels, such as bis-acrylamide, polyacrylamide, streptavidine acrylamide, poly-N-isopropylacrylamide, or poly N-isopropylpolyacrylamide or mixtures thereof. In one example the hydrogel particle comprises acrylamide, bis-acrylamide and strepatvidine acrylamide.

For example, an aqueous solution of a monomer may be dispersed in a compartment, for instance a droplet, and then polymerized, e.g., to form a gel. Another example is a hydrogel, such as alginic acid that can be gelled by the addition of calcium ions. In some cases, gelation initiators (ammonium persulfate and TEMED for acrylamide, or $Ca^{2+}$ for alginate) can be added to a compartment, for instance a droplet, for example, by co-flow with the aqueous phase, by co-flow through the oil phase, or by coalescence of two different drops, e.g., as discussed in U.S. patent application Ser. No. 11/360,845, filed Feb. 23, 2006, entitled "Electronic Control of Fluidic Species," by Link, et ah, published as U.S. Patent Application Publication No. 2007/000342 on Jan. 4, 2007; or in U.S. patent application Ser. No. 11/698,298, filed Jan. 24, 2007, entitled "Fluidic Droplet Coalescence," by Ahn, et al.; each incorporated herein by reference in their entireties.

In another set of embodiments, the particles may comprise one or more polymers and are thus herein referred to as "polymeric particle". Exemplary polymers include, but are not limited to, polystyrene (PS), polycaprolactone (PCL), polyisoprene (PIP), poly(lactic acid), polyethylene, polypropylene, polyacrylonitrile, polyimide, polyamide, and/or mixtures and/or co-polymers of these and/or other polymers.

In addition, in some embodiments, the particles may be magnetic and is thus referred to as "magnetic particle", which could allow for the magnetic manipulation of the particles. For example, the particles may comprise iron or other magnetic materials. The particles could also be functionalized so that they could have other molecules attached, such as proteins, nucleic acids or small molecules. Thus, some embodiments of the present invention are directed to a set of particles defining a library of, for example, nucleic acids, proteins, small molecules, or other species such as those described herein. In some embodiments, the particle may be fluorescent.

In one embodiment, the particle comprises streptavidin. Streptavidin may be coupled to the surface of the particle defined herein above.

In one embodiment the hydrogel particles have a size from 1 pL to 1000 pL, such as 1 pL to 500 pL, 1 pL to 400 pL, 1 pL to 400 pL, 1 pL to 300 pL, for example 5 pL to 300 pL, 5 pL to 250 pL, 5 pL to 200 pL, 10 pL to 250 pL, 10 pL to 200 pL, preferably 10 pL to 200 pL.

As it will be understood by the skilled in the art and as it will be further explained in the section "A method for preparing a plurality of microfluidic droplets" the number of cells encapsulated in one compartment, for instance a droplet, follows a probability distribution, for example a Poisson distribution, and depends on, for example, the concentration of the cells in the first fluid, the concentration of particles in the second fluid, the geometry of the main channel and the secondary channel, the injection parameters of the first fluid, of the second fluid and of the carrier fluid used in the method for preparing a plurality of microfluidic droplets of the invention.

Accordingly, in step a) of the method of the invention, a plurality of cells comprised in an aqueous composition are introduced into a plurality of compartments, in particular encapsulated in a plurality of microfluidic droplets, and the number of cells introduced into 1 compartment, in particular encapsulated in 1 droplet follows, depending on the parameters used in the "method for preparing a plurality of microfluidic droplets" a Poisson distribution. The parameters can be adapted to obtain, for instance, compartments with either 1 or 0 cells in it, thus avoiding compartments containing several cells.

As shown by the inventors, the parameters used to introduce into or encapsulate, preferably encapsulate, cells can be adapted to obtain at least some of the compartments comprising a single cell. The at least some compartments further comprise, in context of the present invention, a reverse transcriptase and at least one type of an oligonucleotide, as further defined herein below.

Accordingly in one embodiment, the at least some compartments of step a), preferably droplets of step a), are provided at a velocity of 1 to 2000 compartments per second, such as 1 to 1000 compartments per second, 1 to 800 compartments per second, 1 to 700 compartments per second, 1 to 600 compartments per second, 1 to 500 compartments per second, 1 to 400 compartments per second, 1 to 300 compartments per second, 1 to 200 compartments per second, 1 to 100 compartments per second, 1 to 80 compartments per second, 1 to 70 compartments per second, 1 to 50 compartments per second, for example 10 to 300 compartments per second, 50 to 300 compartments per second, 100 to 300 compartments per second, 150 to 300 compartments per second, 150 to 250 compartments per second, 175 to 250 compartments per second, typically, 1 to 1000 compartments per second, preferably 175 to 250 compartments per second.

Furthermore, as it will be understood by the skilled in the art, based on different parameters, compartments can be produced in a way that they contain 0, 1 or 2 particles per compartment, thus avoiding compartments containing more than two particles. In one particular embodiment, the compartments are produced in a way that they contain 0 or 1 particle per compartment, thus avoiding compartments containing more than one particle.

In a particular example, as it will be understood by the skilled in the art, based on different parameters, such as, for example, particle concentration and flow velocities the droplets can be produced in a way that they contain 0, 1 or 2 particles per droplet, thus avoiding droplets containing more than two particles. In one particular embodiment, the droplets are produced in a way that they contain 0 or 1 particle per droplet, thus avoiding droplets containing more than one particle.

Accordingly, in one embodiment, the particles are introduced into or encapsulated within the compartments at no more than about 2 particles/compartments, preferably, in a further embodiment, the particles are introduced into or encapsulated within the compartments at no more than about 1 particle/compartment, or the particles are introduced into or encapsulated within the compartments preferentially with 1 particle/compartment, or the particles are introduced into or encapsulated within the compartments with an average of 1 particle/compartment.

In one embodiment, in particular when referring to droplets as compartments, the particles are preferably encapsulated within the droplets, with the number of particles as defined herein above. In line with the above, it will be also understood by the skilled in the art that, when referring to droplets, the size of the droplets as provided in step a) follows a probability distribution, such as a Poisson distribution. It will be further understood that the parameters used in step a) for providing microfluidic droplets wherein at least some of those droplets are as defined in the claim can be regulated in order to obtain a plurality of microfluidic droplets having a specific volume.

A "droplet" generally refers to a measure of volume and further refers in context of the present invention, to an isolated portion of a first fluid that is surrounded by a second fluid. It is to be noted that a droplet is not necessarily spherical, but may assume other shapes as well, for example, depending on the external environment.

By "the plurality of compartments has a volume of less than 3 nL", it is meant that each compartment, in the plurality of compartments, has a volume of less than 3 nL.

The "compartment" or "the plurality of compartments", preferably the "droplet" or "the plurality of droplets" in context of the invention has a volume of less than 3 nL. In one embodiment, said plurality of microfluidic droplets has a volume of less than 2.5 nL, less than 2 nL, less than 1.5 nL, less than 1 nL, less than 0.5 nL, for example 0.1 nL to 3 nL, 0.5 nL to 3 nL, 1 nL to 3 nL, typically, 0.1 nL, 0.5 nL, 1 nL, 1.2 nL, 1.4 nL, 1.6 nL, 1.8 nL, 2.0 nL, 2.2 nL, 2.4 nL, 2.6 nL, 2.8 nL, 3 nL.

In one preferred embodiment, the plurality of compartments has a volume equal to or less than 1 nL.

Contrary to prior art disclosure the inventors demonstrated that the method of the present invention can be used to capture and barcode efficiently the whole transcriptome of a single cell (as demonstrated in Example 10) or, alternatively, to specifically capture and barcode a gene specific transcriptome in volumes less than 3 nL provided the concentration of one type of an oligonucleotide as defined herein above is 100 nM or more.

The "transcriptome" generally refers to the set of all or a part of all messenger RNA molecules in one cell or a population of cells. Accordingly, the "transcriptome of a cell" or "the transcriptome of a single cell" herein refers to the set of all or a part of all messenger RNA molecules in one cell.

As it will be understood by the skilled in the art, a gene specific transcriptome thus refers to the set of all messenger RNA molecules derived from one gene.

As it is known by the skilled in the art, different gene products, so called isoforms, may be encoded by one gene. Accordingly, a gene specific transcriptome may further refer to the messenger RNA molecules of at least one specific isoform of one specific gene, such as the messenger RNA molecules of 1, 2, 3, or 4 specific isoforms of one specific gene or to the messenger RNA molecules of all isoforms of one specific gene.

Accordingly, in one embodiment, the nucleic acid in context of the present invention is cDNA or RNA, preferably RNA.

In one embodiment, RNA is selected from the group consisting of mRNA, tRNA, rRNA, catalytic RNA, siRNA, miRNA, antisense RNA, lncRNA and pIRNA, preferably mRNA.

In a further embodiment, mRNA comprises a poly A sequence, also called poly A tail.

Furthermore, in one particular embodiment, the "at least some of the released nucleic acids" in context of the present invention refers to at least one nucleic acid, preferably, at least 2, at least 3, at least 4, at least 5, nucleic acids or more. In one particular, the nucleic acids of step c) and d) refer to 1, 2, 3, 4, 5, 6, 7, 8, 9 or 10 nucleic acids.

The method of the invention can be used to transcribe from one specific nucleic acid up to all nucleic acids of a single cell.

Accordingly, in further embodiments, the "at least some of the released nucleic acids" of step c) and d) in context of the present invention refers to from 1 to 100000 nucleic acids, such as 1 to 80000, 1 to 60000, 1 to 40000, such as 1, 1000, 2000, 4000, 6000, 8000, 10000, 12000, 14000, 16000, 20000, 25000, 30000, 45000, 50000 nucleic acids. Accordingly, in one embodiment, the nucleic acid herein refers to the RNA of all genes.

As mentioned above, as demonstrated by the inventors the method of the invention also refers to capturing and transcribing a gene specific transcriptome.

Accordingly, in one embodiment, the nucleic acid herein refers to the RNA of (a) specific gene(s). As it will be understood by the skilled in the art said gene(s) may be any gene of interest.

In one embodiment, said specific gene is selected from the group consisting of antibody heavy chain variable gene, antibody heavy chain constant gene, antibody light chain variable gene, antibody light chain constant gene, alpha T-cell receptor gene, beta T-cell receptor gene, and delta T-cell receptor gene and gamma T-cell receptor gene.

In one embodiment the nucleic acid as referred to in step c) and d) is a gene specific nucleic acid wherein the gene may be selected from the list consisting of antibody heavy chain variable gene, antibody heavy chain constant gene, antibody light chain variable gene, antibody light chain constant gene, alpha T-cell receptor gene, beta T-cell receptor gene, and delta T-cell receptor gene and gamma T-cell receptor gene.

In one particular embodiment the nucleic acid referred to in step c) and d) is a nucleic acid specific to at least two genes, wherein the at least two genes are selected from the list consisting of antibody heavy chain variable gene, antibody heavy chain constant gene, antibody light chain variable gene, antibody light chain constant gene, alpha T-cell receptor gene, beta T-cell receptor gene, and delta T-cell receptor gene and gamma T-cell receptor gene.

In one embodiment the nucleic acid as referred to in step c) and d) is a gene specific nucleic acid wherein the gene may be selected from the list consisting of antibody heavy chain variable gene, antibody heavy chain constant gene, antibody light chain variable gene, antibody light chain constant gene, alpha T-cell receptor gene, beta T-cell receptor gene, and delta T-cell receptor gene and gamma T-cell receptor gene, preferably antibody heavy chain variable gene, antibody heavy chain constant gene, antibody light chain variable gene and antibody light chain constant gene.

In a further particular embodiment the nucleic acid referred to in step c) and d) is a nucleic acid specific to at least three genes, wherein the at least three genes are selected from the list consisting of antibody heavy chain variable gene, antibody heavy chain constant gene, antibody light chain variable gene, antibody light chain constant gene, alpha T-cell receptor gene, beta T-cell receptor gene, and delta T-cell receptor gene, preferably, alpha T-cell receptor gene, beta T-cell receptor gene, and delta T-cell receptor gene and gamma T-cell receptor gene.

It will be understood by the skilled in the art that when the transcriptome of a cell is captured, oligonucleotides having a primer sequence, wherein said primer sequence is specific to all mRNAs will be used, such as poly T primer sequences, as further defined herein below, whereas, when a gene specific transcriptome is captured and to be barcoded, oligonucleotides comprising a gene specific primer sequence are used, as further defined herein below.

"At least one type of an oligonucleotide" as used in context of the present invention refers to an oligonucleotide, as defined herein above, comprising a barcode sequence and a primer sequence, wherein each different primer sequence defines a different oligonucleotide type. In one embodiment, the at least one type of an oligonucleotide comprises from 5' to 3' a barcode sequence and a primer sequence.

"At least one" in the wording "at least one type of an oligonucleotide" refers to at least 2, at least 3, at least 4, at least 5, at least 6, at least 7, at least 8, at least 9 at least 10 types or more of an oligonucleotide. The number of different types of oligonucleotides present in one compartment depends on the number of genes of which the RNA is to be captured and barcoded.

As mentioned above, one type of an oligonucleotide distinguishes from another type of an oligonucleotide by its primer sequence.

The whole transcriptome may be transcribed using one primer sequence, the polydT primer. It will be understood, that the number of types of oligonucleotides corresponds to at least the number of specific genes of which the transcriptome is to be captured and barcoded.

Accordingly, in one further embodiment, at least one type of an oligonucleotide refers to 1 to 100 types of an oligonucleotide, 1 to 80, 1 to 60, 1 to 40, 1 to 30, 1 to 20, 1 to 10, preferably, 1, 2, 3, 4, 5, 6, 7, 8, 9 types of an oligonucleotide.

Accordingly, in one embodiment, different types of oligonucleotides bound to the particle contained in one compartment comprise the same barcode sequence.

In one embodiment, when the compartment is a droplet the particle is encapsulated in said droplet.

In one embodiment, different types of oligonucleotides bound to the particle encapsulated in one compartment comprise the same barcode sequence.

As defined in the methods of the invention preferably the concentration of each type of oligonucleotide in the compartment is at least 100 nM.

Accordingly, in some embodiments, the concentration of each type of oligonucleotide in the compartment is at least 100 nM, or preferably more than 100 nM.

In some embodiments, the concentration of each type of oligonucleotide in the compartments is at least 150 nM, at least 200 nM, at least 300 nM, at least 400 nM, at least 500 nM, at least 600 nM, at least 700 nM, at least 800 nM, at least 900 nM and at least 1 µM, such as for instance 100 nM to 5 µM, 100 nM to 4 µM, 100 nM to 3 µM, 100 nM to 2 µM, 100 nM to 1 µM, preferably 100 nM to 500 nM.

In one example, the primer sequence is a poly T primer sequence and the concentration of the oligonucleotide is 100 nM to 3300 nM (corresponding to 3.3 µM).

In a further example, the primer sequence is a gene specific primer sequence and the concentration of the oligonucleotide is 100 nM or 1000 nM (corresponding to 1 µM).

For instance, the inventors demonstrate that the oligonucleotide density/primer concentration per cell, related to compartment volume enable efficient capture and barcoding (with the hypothesis of 1 particle per compartment).

TABLE 1 relation oligonucleotide density/primer concentration (one type of oligonucleotide containing one given barcode sequence and one given primer and compartment volume)

| Oligonucleotide density | Primer concentration per cell | | | | |
| | in 100 pL | in 500 pL | in 1 nL | in 5 nL | in 10 nL |
|---|---|---|---|---|---|
| 10e9 | 16.6 µM | 3.3 µM | 1.66 µM | 332 nM | 166 nM |
| 10e8 | 1.66 µM | 332 nM | 166 nM | | |
| 10e7 | 166 nM | | | | |
| 10e6 | | | | | |
| 10e5 | | | | | |

The "barcode sequence" or simply called "barcode" herein refers to a unique nucleic acid sequence that can be distinguished by its sequence from another nucleic acid sequence, thus permitting to uniquely label a nucleic acid sequence so that it can be distinguished from another nucleic acid carrying another barcode sequence.

In one embodiment, the barcode sequence uniquely identifies the nucleic acids released by a single cell from nucleic acids released from other cells, for instance, even after the nucleic acids are pooled together.

In some embodiments, the barcode sequence may be used to distinguish tens, hundreds, or even thousands of nucleic acids, e.g., arising from different cells or other sources.

In one embodiment, the barcode sequence may be of any suitable length. The barcode sequence is preferably of a length sufficient to distinguish the barcode sequence from other barcode sequences. In one embodiment, a barcode sequence has a length of 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 72, 74, 76, 78, 80, 85, 90 or more nucleotides, such as 50 to 85, 60 to 80, 70 to 80 nucleotides.

In one embodiment, the barcode sequence consists of more than one barcode sequence, wherein the barcoded sequences are different.

In a related embodiment, the different barcode sequences may be taken from a "pool" of potential barcode sequences. If the barcode sequence consists of more than one barcode sequence, the barcode sequences may be taken from the same, or different pools of potential barcode sequences. The pool of sequences may be selected using any suitable technique, e.g., randomly, or such that the sequences allow for error detection and/or correction, for example, by being separated by a certain distance (e.g., Hamming distance) such that errors in reading of the barcode sequence can be detected, and in some cases, corrected. The pool may have any number of potential barcode sequences, e.g., at least 100, at least 300, at least 500, at least 1,000, at least 3,000, at least 5,000, at least 10,000, at least 30,000, at least 50,000, at least 100,000, at least 300,000, at least 500,000, or at least 1,000,000 barcode sequences.

Methods to join different barcode sequences taken from one "pool" or more than one pool are known to the skilled in the art and include, but are not limited to, the use of ligases and/or using annealing or a primer extension method.

Non-limiting examples of ligases include DNA ligases such as DNA Ligase I, DNA Ligase II, DNA Ligase III, DNA Ligase IV, T4 DNA ligase, T7 DNA ligase, T3 DNA Ligase, *E. coli* DNA Ligase, Taq DNA Ligase, or the like. Many such ligases may be purchased commercially.

In one embodiment, the barcode sequence is a double stranded or single stranded nucleic acid.

A "primer sequence" is typically a short single-stranded nucleic acid, of between 10 to 50 nucleotides in length, designed to perfectly or almost perfectly match a nucleic acid of interest, to be captured and then amplified by typically PCR or reverse transcribed by typically RT. The primer sequences are "specific" to the nucleic acids they hybridize to, i.e. they preferably hybridize under stringency hybridization conditions, more preferably under high stringency hybridization conditions, or are complementary to or almost complementary to the nucleic acids they hybridize to, also called target sequence.

Typically, the primer sequence serves as a starting point for nucleic acid synthesis, allowing polymerase enzymes such as nucleic acid polymerase to extend the primer sequence and replicate the complementary strand. A primer sequence may be complementary to and hybridize to a target nucleic acid. In some embodiments, a primer sequence is a synthetic primer sequence. In some embodiments, a primer sequence is a non-naturally-occurring primer sequence. A primer sequence typically has a length of 10 to 50 nucleotides. For example, a primer sequence may have a length of 10 to 40, 10 to 30, 10 to 20, 25 to 50, 15 to 40, 15 to 30, 20 to 50, 20 to 40, or 20 to 30 nucleotides. In some embodiments, a primer sequence has a length of 18 to 24 nucleotides.

In one embodiment, the primer sequence is located the 3' side of the oligonucleotide used in context with the invention (i.e. the primer is in 3' position compared to the barcode sequence).

In one embodiment, the primer sequence is selected from the group consisting of a poly-T sequence, a random DNA sequence, and a gene-specific sequence.

A "poly-T sequence" as herein referred to is a sequence comprising 10 to 50, 10 to 40, 10 to 30, 10 to 20, 25 to 50, 15 to 40, 15 to 30, 20 to 50, 20 to 40, or 20 to 30 thymine "T". The Poly T sequence hybridizes with the poly A tail present in mRNAs.

In one embodiment, the random DNA sequence can be of any suitable length, such as 6 to 50, 6 to 50, 6 to 40, 6 to 30, 6 to 20, 10 to 50, 10 to 40, 25 to 50, 15 to 40, 15 to 30, 20 to 50, 20 to 40, or 20 to 30 nucleotides.

In one particular embodiment, the primer sequence is a gene-specific sequence and the gene is selected from the group consisting of antibody heavy chain variable gene, antibody heavy chain constant gene, antibody light chain variable gene, antibody light chain constant gene, alpha T-cell receptor gene, beta T-cell receptor gene, delta T-cell receptor gene.

The term "antibody" in the wording "antibody heavy chain variable gene", "antibody heavy chain constant gene", "antibody light chain variable gene" and "antibody light chain constant gene" is as defined herein above.

The term "T-cell receptor" in the wording "alpha T-cell receptor gene", "beta T-cell receptor gene" and "delta T-cell receptor gene" or "gamma T-cell receptor gene" is as defined herein above.

The word "gene" is as defined herein above.

In one specific embodiment, the at least one type of an oligonucleotide is at least two types of oligonucleotides, wherein at least one type of oligonucleotide comprises a primer sequence specific for antibody heavy chain variable gene and wherein the other at least one type of oligonucleotide comprises a primer sequence specific for antibody light chain variable gene.

In another particular embodiment, the at least one type of an oligonucleotide is at least two types of oligonucleotides, wherein at least one type of oligonucleotide comprises a primer sequence specific for the alpha T-cell receptor gene or the beta T-cell receptor gene or gamma T-cell receptor, and wherein the other at least one type of oligonucleotide comprises a primer sequence specific for the delta T-cell receptor gene.

In another particular embodiment, the at least one type of an oligonucleotide is at least three types of oligonucleotide, wherein at least one type of oligonucleotide comprises a primer sequence specific for the alpha T-cell receptor gene and a second type of oligonucleotide comprises a primer sequence specific for the beta T-cell receptor gene, and wherein a third type of oligonucleotide comprises a primer sequence specific for the delta T-cell receptor gene.

In one embodiment, the oligonucleotide further comprises a promoter and/or a spacer sequence.

Examples of promoter sequences include, but are not limited to, T7 promoters, T3 promoters, or SP6 promoters.

It will be understood by the skilled in the art that binding the oligonucleotides temporally to a particle permits to provide particles having a high amount of oligonucleotides. Furthermore, binding the at least one type of oligonucleotide initially to the particle facilitates the introduction of oligonucleotides into each compartment, in particular into each droplet, wherein the at least one type of oligonucleotides have the same barcode sequence.

Accordingly, in one embodiment, the at least one type of oligonucleotide is covalently bonded or non-covalently bonded to the particle.

"Non-covalently bonded" herein refers, for example, to a streptavidin-biotin bond. Other non-covalent bonds are known to the skilled in the art, such as avidin biotin bonds or his tag and nickel bonds.

"Covalently bonded" herein refers for example to an amino bond or an acrydite phosphoramidite bond.

"Streptavidin" generally refers to a 52.8 kDa protein purified from the bacterium *Streptomyces avidinii*. Streptavidin homo-tetramers have an extraordinarily high affinity for biotin with a dissociation constant (Kd) on the order of $\approx 10^{-14}$ mol/L, the binding of biotin to streptavidin is one of the strongest non-covalent interactions known in nature.

In a preferred embodiment, the non-covalent bond is a streptavidin-biotin bond.

Streptavidin-Biotin bonds are known to the skilled in the art. Accordingly, in one embodiment the particle as herein defined comprises streptavidin. Accordingly, in the same embodiment, the at least one type of oligonucleotide, as herein defined comprises biotin. In other words, the at least one type of oligonucleotide is functionalized with biotin.

Independent of the type of bond used to link the at least one type of oligonucleotide to the particle, the at least one type of oligonucleotide may further comprise at least one linker sequence.

Accordingly, in a further embodiment, the "at least one type of an oligonucleotide" or simply the "oligonucleotide" further comprises at least one linker sequence, said linker sequence is preferably comprised at the 5' end. Accordingly, in one embodiment, the at least one type of an oligonucleotide comprises from 5' to 3' a linker sequence, a barcode sequence and a primer sequence.

In one embodiment, the "linker sequence" is a sequence with which one the oligonucleotide is optionally bonded to the particle.

"Optionally bonded herein" refers to the possibility that once the at least one type of oligonucleotide bonded to the particle is loaded into the compartment or the plurality of compartments, the at least one type of oligonucleotide might be released, so that the compartment comprises the particle and the at least one type of oligonucleotide without the at least one type of oligonucleotide being bond to said particle.

Preferably, the linker sequence is a cleavable linker sequence, e.g., that can be cleaved upon application of a suitable stimulus, such as enzymatic and/or photocleavage.

"Cleavable linkers" may include, but are not limited to, TEV, trypsin, thrombin, cathepsin B, cathespin D, cathepsin K, caspase lumatrix metalloproteinase sequences, phosphodiester, phospholipid, ester, -galactose, dialkyl dialkoxysilane, cyanoethyl group, sulfone, ethylene glycolyl disuccinate, 2-N-acyl nitrobenzenesulfonamide, a-thiophenylester, unsaturated vinyl sulfide, sulfonamide after activation, malondialdehyde (MDA)-indole derivative, levulinoyl ester, hydrazone, acylhydrazone, alkyl thioester, disulfide bridges, azo compounds, 2-Nitrobenzyl derivatives, phenacyl ester, 8-quinolinyl benzenesulfonate, coumarin, phosphotriester, bis-arylhydrazone, bimane bi-thiopropionic acid derivative, paramethoxybenzyl derivative, tert-butylcarbamate analogue, dialkyl or diaryl dialkoxysilane, orthoester, acetal, aconityl, hydrazone, b thiopropionate, phosphoramidate, imine, trityl, vinyl ether, polyketal, alkyl 2-(diphenylphosphino)benzoate derivatives, allyl ester, 8-hydroxyquinoline ester, picolinate ester, vicinal diols, and selenium compounds (see, e.g. Leriche G, Chisholm L, Wagner A.

Cleavable Linkers are well known to the skilled in the art and are further described in Chemical Biology, for example in Leriche H. et al. (Bioorg Med Chem. 15; 20(2):571-82. 2012). Cleavage conditions and reagents include, but are not limited to, enzymes, nucleophilic/basic reagents, reducing agents, photo-irradiation, electrophilic/acidic reagents, organometallic and metal reagents, and oxidizing reagents.

As mentioned above, in one embodiment, the method of the invention further comprises a step of releasing the at least some of the oligonucleotides bound to a particle from said particle prior or after lysing the cells.

The step of releasing at least some of the oligonucleotides may further occur after lysing the cells and before reverse transcribing the released nucleic acids hybridized to said oligonucleotide or after lysing the cells and after reverse transcribing the released nucleic acids hybridized to said oligonucleotide.

The skilled in the art will understand that depending on the time point selected for releasing the at least some of the oligonucleotides, the term "at least some of the oligonucleotides" might refer to, for example, at least some of the oligonucleotides hybridized to the nucleic acids released by the cells or a DNA/RNA duplex, as defined above.

In one embodiment, the at least some of the oligonucleotides can be released using any means, such as enzymes, nucleophilic/basic reagents, reducing agents, photo-irradiation, electrophilic/acidic reagents, organometallic and metal reagents, and oxidizing reagents.

In one embodiment, the at least some of the oligonucleotides can be released using enzymatic and/or photo cleavage. For example, an endonuclease may be used to cleave a linker sequence or any other sequence to release the at least some of the oligonucleotides from the particle.

In a further embodiment, releasing the oligonucleotide refers to disrupting the bond, such as a streptavidin biotin. Methods to disrupt a streptavidin biotin bond are known to the skilled in the art and include enzymatic digestion of streptavidin and/or denaturation of streptavidin.

In one embodiment, the oligonucleotide is released by enzymatic digestion of streptavidin.

The "cell" in context of the present invention is given its ordinary meaning as used in biology, for example a cell refers to an autonomous self-replicating unit that may exist as functional independent unit of life, for example for unicellular organism, or as sub-unit in a multicellular organism, for example in plants and mammals, that is specialized into carrying out particular functions towards the cause of the organism as a whole. However a "cell" may further refer to quiescent cells which typically is still capable of cell division when mitotic stimulation is applied.

In one embodiment, cells refer to prokaryotic cells or eukaryotic cells, preferably, eukaryotic cells.

The defining feature distinguishing an "eukaryotic cell" from a prokaryotic cell is that they have membrane-bound organelles, especially the nucleus, which contains the genetic material, and is enclosed by the nuclear envelope.

An "eukaryotic cell" in context of the present invention is selected from the group consisting of a mammal cells, plant cell and fungal cell, preferably mammalian cell.

A "mammal" herein refers to any mammal, including humans, domestic and farm animals, and zoo, sports, or pet animals, such as dogs, cats, cattle, horses, sheep, pigs, goats, rabbits, etc. Preferably, the mammal is human.

Accordingly, in one embodiment, the cell is a mammalian cell, an engineered mammalian cell or a cell line or a mammalian immune cell.

In one embodiment, the mammalian cell is an immune cell.

In one embodiment, an immune cell may be, but is not limited to, B cells, T cells, or hybridomas, preferably B cell.

In one embodiment, a cell or plurality of cells herein refers to different types of cells or to cells of the same type or origin exposed to different conditions.

In one particular embodiment, the cell is a non-mammalian cell.

In one further particular embodiment, the non-mammalian cell is a yeast cell, an avian cell or a shark cell.

Step d) of the methods of the invention refers to reverse transcribing the released nucleic acids hybridized to said oligonucleotide using the primer sequence in at least some of the compartments. Reverse transcription is performed using the reverse transcriptase (RT) comprised in at least some of the compartment.

The "reverse transcriptase (RT)" in context of the present invention is an enzyme used to generate complementary DNA (cDNA) from an RNA template, in a process termed reverse transcription.

In one embodiment, the reverse transcriptase is selected from the group consisting of Superscriptase I, Superscriptase II, Superscriptase III, Superscriptase IV, Murine Leukemia RT, SmartScribe RT or MultiScribe RT.

In one embodiment, the reverse transcriptase is at a concentration of 1 to 50 U/μl, preferably 5 to 25 U/μl, for example at 12.5 U/μl.

"Reverse Transcription" or "RT reaction" is a process in which single-stranded RNA is reverse transcribed into a single-stranded complementary DNA (cDNA) by using total cellular RNA or poly(A) RNA, a reverse transcriptase enzyme, a primer, dNTPs and an RNase inhibitor. It will be understood by the skilled in the art, that the product of the reverse transcription is a RNA/DNA duplex comprising a single strand cDNA hybridized to its template RNA. As it will be further understood, said RNA/DNA duplex is further linked to the oligonucleotide comprising the primer sequence used for the reverse transcription.

Accordingly, it will be understood by the skilled in the art, that after reverse transcribing the nucleic acids in step d) of the methods of the invention the compartment or the plurality of compartments further comprises cDNAs.

Accordingly, in one embodiment, the at least some of the compartments further comprise single cell cDNAs produced by reverse transcription of nucleic acids from the single cell lysate.

In one embodiment, said cDNA refers to a single-stranded complementary DNA.

In a further embodiment, said cDNA is comprised in a RNA/DNA duplex.

In one embodiment, the RNA/DNA duplex refers to the RNA that has been reverse transcribed and is hybridized to the primer sequence of the at least one type of oligonucleotide.

As it will be understood by the skilled in the art, in one embodiment, the RNA/DNA duplex is linked to the oligonucleotide comprising the primer sequence to which the nucleic acid, preferably mRNA was hybridized in step c) and which was used for reverse transcription in step d).

In one embodiment, the compartment or plurality of compartments comprise a reverse transcriptase composition.

In one embodiment, a reverse transcriptase composition comprises a protease inhibitor, dNTPs and/or DTT, preferably protease inhibitor, dNTPs and DTT.

In one embodiment, DTT is at a concentration of 1 mM to 10 mM, preferably 5 mM.

In one embodiment, the protease inhibitor comprises a plurality of protease inhibitors.

In one embodiment, the protease inhibitor is selected from the list consisting of Leupeptin hemisulfate salt, pepstatin A, AEBSF, Aprotinin, Bestatin hydrochloride, E-64 and PMSF.

For example, the protease inhibitor may comprise one or more of Leupeptin hemisulfate salt, pepstatin A, AEBSF, Aprotinin, Bestatin hydrochloride, E-64 and PMSF.

As used herein, the term "dNTP" refers to a deoxynucleoside triphosphate, e.g. deoxyadenosine-5'-triphosphate (dATP, "A"), deoxycytidine-5'-triphosphate (dCTP, "C"), deoxyguanosine-5'-triphosphate (dGTP, "G"), deoxythymidine-5'-triphosphate (dTTP, "T") or deoxyuridine-5'-triphosphate (dUTP, "U"). The term "dNTP" is intended to refer also to deoxynucleoside triphosphates comprising modified bases and base analogues that are capable of mimicking the base pairing of A, C, G, T, or U, or that are capable of base pairing in a degenerate mode, e.g., a base that pairs with A or G, C or T, A or C, G or T, G or C, or A or T, called nucleotide analogues. Said nucleotide analogues may be used, for example, for purification, as further explained herein below.

In one embodiment, the dNTP is at a concentration of 0.01 mM to 10 mM, preferably 0.1 to 1 mM, more preferably 0.5 mM.

In one embodiment, a reverse transcriptase composition further comprises a RNase inhibitor.

In context of the present invention, the compartment or plurality of compartments comprises an aqueous composition.

The "aqueous composition" in context of the invention is typically adapted to the cells used in the method of the invention and typically comprises a buffered solution as defined herein below.

Step b) of the method of the invention refers to lysing at least some of the cells within the compartments.

Said "cell lysis" in context of the present invention may be accomplished by enzymatic, physical, and/or chemical means, or any combination thereof, in particular enzymatic, physical, and/or chemical means. Other cell disruption methods may be also be used.

Accordingly, in one embodiment, the compartment or plurality of compartments are lysed in step a) using enzymatic, physical, and/or chemical cell lysis.

"Enzymatic methods" to remove cell walls is well-established in the art. The enzymes are generally commercially available and, in most cases, were originally isolated from biological sources. Enzymes commonly used include lysozyme, lysostaphin, zymolase, mutanolysin, glycanases, proteases, and mannose.

As known by the skilled in the art "chemical cell lysis" is achieved using chemicals such as detergents, which disrupt the lipid barrier surrounding cells by disrupting lipid-lipid, lipid-protein and protein-protein interactions. The ideal detergent for cell lysis depends on cell type and source. Nonionic and zwitterionic detergents are milder detergents. The Triton X series of nonionic detergents and 3-[(3-Cholamidopropyl)dimethylammonio]-l-propanesulfonate (CHAPS), a zwitterionic detergent, are commonly used for these purposes. In contrast, ionic detergents are strong solubilizing agents and tend to denature proteins, thereby destroying protein activity and function. SDS, an ionic detergent that binds to and denatures proteins, is used extensively in the art to disrupt cells.

"Physical cell lysis" refers to the use of sonication, ice shock or electroporation.

In one example the cells within the compartments are lysed on ice.

In one preferred embodiment, the cell lysis of step a) does not destroy the compartments, in particular the droplets, in context of the invention.

According to the above, in one embodiment, the compartment or plurality of compartments comprise a lysis composition.

In one embodiment, the lysis composition comprises enzymes selected from the group consisting of lysozyme, lysostaphin, zymolase, mutanolysin, glycanases, proteases, and mannose.

In one preferred embodiment, the lysing composition in context of the present invention comprises magnesium chloride, a detergent, a buffered solution and an RNase inhibitor.

In one embodiment, the magnesium chloride is used at a concentration of between 1 mM to 20 mM.

In one embodiment, the detergent is selected from the group consisting of Triton-X-100, NP-40, Nonidet P40, and Tween-20 and IGEPAL CA 630.

In one embodiment, the detergent is at a concentration of 0.1% to 10%.

Nonlimiting examples of the buffered solution may include Tris-HCl, Hepes-KOH, Pipes-NaOH, maleic acid, phosphoric acid, citric acid, malic acid, formic acid, lactic acid, succinic acid, acetic acid, pivalic (trimethylacetic) acid, pyridine, piperazine, picolinic acid, L-histidine, MES, Bis-tris, bis-tris propane, ADA, ACES, MOPSO, PIPES, imidazole, MOPS, BES, TES, HEPES, DIPSO, TAPSO, TEA (triethanolamine), N-Ethylmorpholine, POPSO, EPPS, HEPPS, HEPPSO, Tris, tricine, Glycylglycine, bicine, TAPS, morpholine, N-Methyldiethanolamine, AMPD (2-amino-2-methyl-1,3-propanediol), Diethanolamine, AMPSO, boric acid, CHES, glycine, CAPSO, ethanolamine, AMP (2-amino-2-methyl-1-propanol), piperazine, CAPS, 1, 3-Diaminopropane, CABS, or piperidine (see also, www.reachdevices.com/Protein/BiologicalBuffers.html). Nonlimiting examples of RNase inhibitors may include RNase OUT, IN, SuperIN Rnase, and those inhibitors targeting a wide range of RNAse (e.g., A, B, C, 1 and T1).

In one example the lysis composition is typically 0.2% Triton, 3 mM MgCl$_2$, 50 mM Tris-HCl pH 7.4.

Step c) of the method of the invention refers to hybridizing at least some of the released nucleic acids to said oligonucleotide in at least some of the compartments.

The hybridization of step c) herein refers to a phenomenon in which the primer sequence present in the oligonucleotide anneals to a complementary nucleic acid sequence of the released nucleic acids, accordingly, as known by the skilled in the art, the temperature to use depends on the primer sequence and/or the RT enzyme used.

In one example, step c) and d) are performed by incubating the compartments for example for 1 h at 55° C. or 2 h at 50° C. during typically mixing of the compartments at for example 550 rpm.

In one embodiment, the cDNAs produced by the reverse transcription of step d) are recovered and further used for, typically, subsequent amplification and sequencing library preparation.

Accordingly, in one embodiment, the method of the invention further comprises recovering single cell cDNAs produced by reverse transcription in at least some of the compartments.

"Recovering" herein refers to isolating the cDNAs produced by reverse transcription in at least some of the compartments from said plurality of compartments.

In one embodiment, recovering herein refers to collecting the compartments comprising cDNA produced by reverse transcription or collecting the aqueous composition contained in said compartments comprising said cDNA, and separating the cDNA comprised in the aqueous composition.

In one particular embodiment, recovering herein refers to collecting the microfluidic droplets comprising cDNA produced by reverse transcription, breaking the microfluidic droplets and separating the cDNA comprised in the aqueous composition from the oil phase of said microfluidic droplets.

Methods to isolate nucleic acids, in particular cDNA from microfluidic droplets are known to the skilled in the art and comprise for example, collecting the microfluidic droplets and breaking the microfluidic droplets using typically perfluoro-octanol (v/v emulsion). Then incubating the emulsion obtained in the previous step until the aqueous and oil phase are separated. In one example, the aqueous phase is typically centrifuged for, for example, 10 min at 10000 g at 4° C. and the supernatant comprising the cDNA is recovered.

In one embodiment, the method further comprises the step of removing unincorporated oligonucleotides, preferably, removing unincorporated oligonucleotides from the aqueous composition of the compartments. In one preferred embodiment, the step of removing unincorporated oligonucleotides composition from the at least some of the compartments takes place after the step of recovering the cDNA produced by reverse transcription as defined herein above.

Preferably, the step of removing unincorporated oligonucleotides precedes the amplification step and/or the sequencing step defined herein below.

It will be understood by the skilled in the art that the step of removing unincorporated oligonucleotides encompasses removing unincorporated barcode sequences.

In one embodiment, removing unincorporated oligonucleotides comprises contacting the aqueous composition of the at least some of the compartments with a purification substrate wherein the purification substrate removes unincorporated oligonucleotides. In one embodiment, the purification substrate comprises beads or particles, which, optionally, form a column. In a further example, unincorporated oligonucleotides are removed by size selection using for example an acrylamide gel.

In one embodiment, the step of removing unincorporated oligonucleotides comprises contacting the aqueous composition of the at least some of the compartments with an exonuclease to degrade the unincorporated oligonucleotides within the aqueous composition of the at least some of the compartments.

In certain embodiments of this step, the exonuclease degrades single stranded nucleic acid sequences from the aqueous compositions comprising the cDNA.

It will be understood by the skilled in the art, that the cDNA obtained in step d) is typically present in form of a RNA/DNA complex and thus protected from said exonucleases.

In one embodiment, the cDNA comprises one or more nucleotide analogs, as defined herein above, facilitating purification of the cDNA sequences or molecules.

As it will be understood by the skilled in the art, in certain embodiments, purified cDNA does not comprise unincorporated oligonucleotides. Accordingly, in certain embodiments, purified cDNA does not comprise unincorporated barcode sequences.

In one embodiment, the cDNA is further treated with RNAse A and/or RNAse H.

"RNAse A" is an endoribonuclease that specifically degrades single-stranded RNA at C and U residues.

In one embodiment, the RNAse A is at a concentration of 10 to 1000 μg/μL, preferably 50 to 200 μg/μL for example at 100 μg/μL.

"RNAse H" is a family of non-sequence-specific endonucleases that catalyze the cleavage of RNA via a hydrolytic mechanism. RNase H's ribonuclease activity cleaves the 3'-O—P bond of RNA in a DNA/RNA duplex substrate to produce 3'-hydroxyl and 5'-phosphate terminated products.

In one embodiment, the RNAse H is at a concentration of 10 to 1000 μg/μL, preferably 50 to 200 μg/μL, for example at 100 μg/μL.

In one embodiment, the cDNA is further treated with Proteinase K.

"Proteinase K" is a broad-spectrum serine protease and digests proteins, preferentially after hydrophobic amino acids.

In one embodiment, the Proteinase K is at a concentration of 0.1 to 5 mg/mL, preferably 0.1 to 1 mg/mL, for example at 0.8 mg/mL.

In one embodiment the method further comprises the step of amplifying the cDNA obtained in step d) of the method of the invention. In one embodiment, said amplification step is performed after removing unincorporated oligonucleotides. In one embodiment, said amplification step is performed prior to the sequencing step defined herein below.

In one embodiment, the amplifying step is performed in a multiplex reaction, a separated polymerase chain reaction (PCR), or a linear amplification.

In one embodiment, the linear amplification is an in vitro transcription.

In one embodiment, the cDNA produced in step d) is quantified using qPCR, such as simplex and/or multiplex qPCR reaction.

In a further embodiment the method further comprises a step of sequencing the cDNA obtained in step d).

In context of the present invention, in one embodiment, the step of sequencing the cDNA herein refers to first contacting the cDNA to a sequencing library and amplifying the sequences of interest from the sequencing library that correspond to the cDNA, respectively.

In one embodiment, the step of sequencing the cDNA may comprise performing a next generation sequencing (NGS) protocol on a sequencing library.

In certain embodiments, the NGS protocol comprises loading an amount of the sequencing library between 4 pM to 20 pM per flow cell of a reagent kit.

In one embodiment, the NGS sequencing protocol further comprises the step of adding 5-60% PhiX to the amount of the sequencing library or to the flow cell of the reagent kit.

Plurality of Microfluidic Droplets

The invention further refers to a plurality of compartments wherein at least some of the compartments comprise (i) a single cell or a single cell lysate comprising nucleic acids and (ii) at least one type of oligonucleotide, and (iii) a reverse transcriptase, wherein the at least one type of oligonucleotide comprises a barcode sequence and a primer sequence, wherein each different primer sequence defines a different oligonucleotide type, and wherein the compartments of the plurality of the compartments contain one or more barcode sequences distinguishable from barcode sequences contained in other compartments of the plurality of compartments;

wherein the plurality of compartments has a volume of less than 3 nL; and preferably wherein the concentration of each type of oligonucleotide in the compartments is at least 100 nM.

As explained herein above, in some embodiments, the at least one type of oligonucleotide is introduced into the compartments by initially binding the at least one oligonucleotide to a particle (e.g., a hydrogel or a polymeric particle or magnetic particle).

Accordingly, in one embodiment, the at least some of compartments further comprise (iv) a particle, wherein the at least one type of oligonucleotide of ii) is preferably bonded to the particle of iv).

Accordingly, in one particular embodiment the invention further refers to a plurality of compartments wherein at least some of the compartments comprise (i) a single cell or a single cell lysate comprising nucleic acids and (ii) at least one type of oligonucleotide, (iii) a reverse transcriptase and (iv) a particle, wherein the at least one type of oligonucleotide of ii) is optionally bonded to said particle (iv), and wherein the at least one type of oligonucleotide comprises a barcode sequence and a primer sequence, wherein each different primer sequence defines a different oligonucleotide type, and wherein the compartments of the plurality of the compartments contain one or more barcode sequences distinguishable from barcode sequences contained in other compartments of the plurality of compartments;

wherein the plurality of compartments has a volume of less than 3 nL; and preferably wherein the concentration of each type of oligonucleotide in the compartments is at least 100 nM.

In one embodiment, the at least one type of oligonucleotide of iii) might be non-covalently bonded or covalently bonded to the particle of iv). Non-covalent bonds and covalent bonds are as defined herein above.

In one particular embodiment, the plurality of compartments has a volume equal to or less than 1 nL.

In one embodiment, at least some of the compartments further comprise v) single cell cDNAs produced by reverse transcription of nucleic acids from the single cell lysate.

The terms "cell", "nucleic acids", "oligonucleotide" or "each type of oligonucleotide", "reverse transcriptase", "barcode sequence", "primer sequence", "volume of compartments", "concentration of each type of oligonucleotide", "particle", "bonded" are as defined herein above in the section "Method for capturing and barcoding single cell nucleic acid".

The features described in the previous section "Method for capturing and barcoding single cell nucleic acid" are entirely applicable to the instant description of the plurality of compartments.

A Method for Preparing a Plurality of Microfluidic Droplets

The invention further refers to a method for preparing a plurality of microfluidic droplets comprising the following steps:

providing a first fluid source, the first fluid comprising a suspension of cells, providing a second fluid source, the second fluid comprising at least one type of an oligonucleotide, wherein the at least one type of oligonucleotide comprises one barcode sequence and a primer sequence, wherein each different primer sequence defines a different oligonucleotide type, and wherein the droplets of the plurality of the microfluidic droplets contain one or more barcode sequences distinguishable from barcode sequences contained in other droplets of the plurality of microfluidic droplets;

providing a carrier fluid, the carrier fluid being immiscible with the first fluid and the second fluid, injecting the carrier fluid in a main channel of a chip, generating a flow of droplets in the carrier fluid by injecting the second fluid and the first fluid in at least a secondary channel of the chip, the secondary channel opening in the main channel, each generated droplet comprising a mix of the first fluid and the second fluid, wherein the concentration of the cells in the first fluid, the concentration of oligonucleotides in the second fluid, the geometry of the main channel and the secondary channel, the injection parameters of the first fluid, of the second fluid and of the carrier fluid are adapted such that each droplet comprises only a single cell and presents a volume of less than 3 nL, and, preferably, such that the concentration of each type of oligonucleotide in each droplet is at least 100 nM.

In one embodiment, the second fluid further comprises a plurality of particles, each particle comprising at least one type of an oligonucleotide bonded thereto, wherein the term "bonded" is as defined herein above.

In the same embodiment, the concentration of the cells in the first fluid, the concentration of particles in the second fluid, the number of oligonucleotides bonded to each particle, the geometry of the main channel and the secondary channel, the injection parameters of the first fluid, of the second fluid and of the carrier fluid are adapted such that each droplet comprises only a single cell and a particle and presents a volume of less than 3 nL, and, preferably, such that the concentration of each type of oligonucleotide in each droplet is at least 100 nM.

In one embodiment, the second fluid further comprises the reverse transcriptase, wherein the reverse transcriptase is as defined herein above.

In one embodiment, the second fluid further comprises a lysis composition.

In one embodiment, the second fluid further comprises the reverse transcription composition as defined herein above.

In an alternative embodiment, the second fluid does not comprise the reverse transcription composition and does not comprise the reverse transcriptase, in the same embodiment, the method for preparing a plurality of microfluidic droplets further comprises providing a third fluid source, the third fluid comprising the reverse transcriptase.

In a related embodiment, the third fluid further comprises a reverse transcriptase composition.

Accordingly, in a further embodiment the invention refers to a method for preparing a plurality of microfluidic droplets comprising the following steps:

providing a first fluid source, the first fluid comprising a suspension of cells, providing a second fluid source, the second fluid comprising at least one type of an oligonucleotide, wherein the at least one type of oligonucleotide comprises one barcode sequence and a primer sequence, wherein each different primer sequence defines a different oligonucleotide type, and wherein the droplets of the plurality of the microfluidic droplets contain one or more barcode sequences distinguishable from barcode sequences contained in other droplets of the plurality of microfluidic droplets;

providing a third fluid source, the third fluid comprising the reverse transcriptase, providing a carrier fluid, the carrier fluid being immiscible with the first fluid, the second fluid and the third fluid, injecting the carrier fluid in a main channel of a chip, generating a flow of droplets in the carrier fluid by injecting the first fluid, the second fluid and the third fluid in at least a secondary channel of the chip, the secondary channel opening in the main channel, each generated droplet comprising a mix of the first fluid, the second and the third fluid, wherein the concentration of the cells in the first fluid, the concentration of oligonucleotides in the second fluid, the geometry of the main channel and the secondary channel, the injection parameters of the first fluid, the second fluid, the third fluid and of the carrier fluid are adapted such that each droplet comprises only a single cell and a particle and presents a volume of less than 3 nL, and, preferably, such that the concentration of each type of oligonucleotide in each droplet is at least 100 nM.

In the same embodiment, the second fluid may further comprise a plurality of particles; each particle comprising at least one type of an oligonucleotide bonded thereto, wherein the term "bonded" is as defined herein above.

In the same embodiment, the concentration of the cells in the first fluid, the concentration of particles in the second fluid, the number of oligonucleotides bonded to each particle, the geometry of the main channel and the secondary channel, the injection parameters of the first fluid, the second fluid and the third fluid and of the carrier fluid are adapted such that each droplet comprises only a single cell and a particle and presents a volume of less than 3 nL, and, preferably, such that the concentration of each type of oligonucleotide in each droplet is at least 100 nM.

In a related embodiment, the second fluid or the third fluid may further comprise a lysis composition.

In a further related embodiment, the third fluid further comprises a reverse transcriptase composition.

In a further embodiment, the invention refers to a method for preparing a plurality of microfluidic droplets comprising the following steps:

providing a first fluid source, the first fluid comprising a suspension of cells, providing a second fluid source, the second fluid comprising at least one type of an oligonucleotide, wherein the at least one type of oligonucleotide comprises one barcode sequence and a primer sequence, wherein each different primer sequence defines a different oligonucleotide type, and wherein the droplets of the plurality of the microfluidic droplets contain one or more barcode sequences distinguishable from barcode sequences contained in other droplets of the plurality of microfluidic droplets;

providing a third fluid source, the third fluid comprising the reverse transcriptase, providing a fourth fluid source, the fourth fluid comprising the lysis composition, providing a carrier fluid, the carrier fluid being immiscible with the first fluid, the second fluid, the third fluid and the fourth fluid, injecting the carrier fluid in a main channel of a chip, generating a flow of droplets in the carrier fluid by injecting the first fluid, the second fluid, the third fluid and the fourth fluid in at least a secondary channel of the chip, the secondary channel opening in the main channel, each generated droplet comprising a mix of the first fluid, the second, the third fluid and the fourth fluid, wherein the concentration of the cells in the first fluid, the concentration of oligonucleotides, the geometry of the main channel and the secondary channel, the injection parameters of the first fluid, the second fluid, the third fluid, the fourth fluid and of the carrier fluid are adapted such that each droplet comprises only a single cell and a particle and presents a volume of less than 3 nL, and, preferably, such that the concentration of each type of oligonucleotide in each droplet is at least 100 nM.

In a related embodiment, the third fluid further comprises a reverse transcriptase composition.

In one embodiment, the second fluid further comprises a plurality of particles; each particle comprising at least one type of an oligonucleotide bonded thereto, wherein the term "bonded" is as defined herein above.

In the same embodiment, the concentration of the cells in the first fluid, the concentration of particles in the second fluid, the number of oligonucleotides bonded to each particle, the geometry of the main channel and the secondary channel, the injection parameters of the first fluid, the second fluid, the third fluid, the fourth fluid and of the carrier fluid are adapted such that each droplet comprises only a single cell and a particle and presents a volume of less than 3 nL, and, preferably, such that the concentration of each type of oligonucleotide in each droplet is at least 100 nM.

It will be understood that in the methods described herein above, in one embodiment, the particles and the cells may be encapsulated within the droplets simultaneously or sequentially, in any suitable order.

The "lysis composition" comprises the same ingredients as defined herein above in the section "Method for capturing and barcoding single cell nucleic acid". However, as it will be understood by the skilled in the art, the concentration of the ingredients present in the lysis composition of the second fluid will be increased in comparison to the concentration of the ingredients present in the plurality of microfluidic droplets that are obtained by set method. In other words, the concentration of the ingredients of the lysis composition present in the plurality of microfluidic droplets will be decreased in comparison to the concentration of the ingredients present in the second fluid.

For example, the concentrations of the ingredients of the lysis composition present in the second fluid may be 3 to 7 times higher, preferably, 3 to 5 times higher, for example 4 times higher than the concentrations present in the final microfluidic droplet or the plurality of microfluidic droplets.

The "reverse transcriptase composition", in context of the method for preparing a plurality of microfluidic droplets, comprises the same ingredients as defined herein above. However, as it will be further understood by the skilled in the art, the concentration of the ingredients contained in the reverse transcriptase composition of the second or third fluid will be increased in comparison to the concentration of the ingredients contained in the reverse transcriptase composition present in the plurality of microfluidic droplets that are obtained by said method.

For example, the concentrations of the ingredients of the reverse transcriptase composition present in the second or third fluid may be 2 to 7 times higher, preferably, 2 to 5 times higher, for example 2.6 times higher than the concentrations present in the plurality of microfluidic droplets, which is as defined herein above.

In one embodiment, the first and second fluid sources are organized in the form of a junction.

In a further embodiment, the first, second and third fluid sources are organized in the form of a junction.

In a further embodiment, the first, second, third fluid and fourth fluid sources are organized in the form of a junction.

The junction may be, for instance, a T-junction, a Y-junction, a channel-within-a-channel junction (e.g., in a coaxial arrangement, or comprising an inner channel and an outer channel surrounding at least a portion of the inner channel), a cross (or "X") junction, a flow-focusing junction, or any other suitable junction for creating droplets. See, for example, International Patent Application No. PCT/US2004/010903, filed Apr. 9, 2004, entitled "Formation and Control of Fluidic Species," by Link, et ah, published as WO 2004/091763 on Oct. 28, 2004, or International Patent Application No. PCT/US2003/020542, filed Jun. 30, 2003, entitled "Method and Apparatus for Fluid Dispersion," by Stone, et ah, published as WO 2004/002627 on Jan. 8, 2004.

In some embodiments, the junction may be configured and arranged to produce substantially monodisperse droplets.

In one embodiment, the plurality of microfluidic droplets are prepared in such a way that there is no more than about 2 particle/droplet, preferably, the plurality of microfluidic droplets are prepared in such a way that there is no more than about 1 particle/droplet or microfluidic droplets are prepared preferentially with 1 particle/droplet, or the microfluidic droplets are prepared with an average of 1 particle/droplet.

The amount of particles/droplet may also be referred to as loading rate.

For example, the average loading rate may be less than about 1 particle/droplet, less than about 0.9 particles/droplet, less than about 0.8 particles/droplet, less than about 0.7 particles/droplet, less than about 0.6 particles/droplet, less than about 0.5 particles/droplet, less than about 0.4 particles/droplet, less than about 0.3 particles/droplet, less than about 0.2 particles/droplet, less than about 0.1 particles/droplet, less than about 0.05 particles/droplet, less than about 0.03 particles/droplet, less than about 0.02 particles/droplet, or less than about 0.01 particles/droplet. In some cases, lower particle loading rates may be chosen to minimize the probability that a droplet will be produced having two or more particles in it. Thus, for example, at least about 50%, at least about 60%, at least about 70%, at least about 80%, at least about 90%, at least about 95%, at least about 97%, at least about 98%, or at least about 99% of the droplets may contain either no particle or only one particle.

Similarly, in some embodiments, the plurality of microfluidic droplets are prepared in such a way that, on the average, each droplet has less than 1 cell in it. In the same embodiments the amounts of cells/droplet may be referred to as loading rate.

For example, the average loading rate may be less than about 1 cell/droplet, less than about 0.9 cells/droplet, less than about 0.8 cells/droplet, less than about 0.7 cells/droplet, less than about 0.6 cells/droplet, less than about 0.5 cells/droplet, less than about 0.4 cells/droplet, less than about 0.3 cells/droplet, less than about 0.2 cells/droplet, less than about 0.1 cells/droplet, less than about 0.05 cells/droplet, less than about 0.03 cells/droplet, less than about 0.02 cells/droplet, or less than about 0.01 cells/droplet. In some cases, lower cell loading rates may be chosen to minimize the probability that a droplet will be produced having two or more cells in it. Thus, for example, at least about 50%, at least about 60%, at least about 70%, at least about 80%, at least about 90%, at least about 95%, at least about 97%, at least about 98%, or at least about 99% of the droplets may contain either no cell or only one cell. In addition, it should be noted that the average rate of particle loading and the average rate of cell loading within the droplets may the same or different.

In some cases, a relatively large number of droplets may be prepared per second, e.g., at least about 10 per second, at least about 30 per second, at least about 50 per second, at least about 100 per second, at least about 300 per second, at least about 500 per second, at least about 1,000 per second, at least about 3,000 per second, at least about 5,000 per second, at least about 10,000 per second, at least about 30,000 per second, at least about 50,000 per second, at least about 100,000 droplets per second, etc. In particular, 1 to 2000 droplets may be prepared per second, such as 1 to 800 droplets per second, 1 to 700 droplets per second, 1 to 600 droplets per second, 1 to 500 droplets per second, 1 to 400 droplets per second, 1 to 300 droplets per second, 1 to 200 droplets per second, 1 to 100 droplets per second, 1 to 80 droplets per second, 1 to 70 droplets per second, 1 to 50 droplets per second, for example 10 to 300 microfluidic droplets per second, 50 to 300 droplets per second, 100 to 300 droplets per second, 150 to 300 droplets per second, 150 to 250 droplets per second, 175 to 250 microfluidic droplets per second, typically, 1 to 1000 droplets per second, preferably 175 to 250 microfluidic droplets per second.

In some cases, as previously discussed, some or all of the droplets may be distinguishable, e.g., on the basis of the type of oligonucleotides present in at least some of the droplets (e.g., which preferably comprises one barcode sequence as defined herein above). In some cases, at least about 50%, at least about 60%, at least about 70%, at least about.

The volume of the plurality of droplets is as defined herein above in the section "Method for capturing and barcoding single cell nucleic acid".

In one embodiment, after preparing a plurality of microfluidic droplets according to the method herein above, the method may further comprise the steps b) to d) of the Method for capturing and barcoding single cell nucleic acid as defined herein above and other further steps of the Method for capturing and barcoding single cell nucleic acid as defined herein above.

The invention further relates to items as described in the priority application U.S. 62/264,414, the content of which is incorporated herein by reference.

Accordingly, the invention further refers to a method for identifying at least two gene sequences from at least one cell comprising, (a) encapsulating at least a first cell, a first carrier linked to a plurality of a first unique DNA barcode, and a reverse transcriptase enzyme to form a first aqueous composition, under conditions such that the first cell releases at least two RNA molecules within the first aqueous composition;

under conditions such that the first unique DNA barcode hybridizes to each of the at least two RNA molecules to form at least two DNA/RNA duplexes, and under conditions such that at least two cDNA transcripts comprising the first unique DNA barcode are generated within the first aqueous composition, wherein the volume of the first aqueous composition is less than 5 nanoliters;

(b) removing unincorporated DNA barcode sequences; and (c) sequencing each of the at least two cDNA transcripts; thereby identifying at least two gene sequences from at least one cell.

According to a further item, the invention refers to a method for identifying at least two gene sequences from at least one cell comprising, (a) encapsulating at least a first cell and a first carrier linked to a plurality of a first unique DNA barcode to form a first aqueous composition, under conditions such that the first cell releases at least two RNA molecules within the first aqueous composition; and under conditions such that the first unique DNA barcode hybridizes to each of the at least two RNA molecules to form at least two DNA/RNA duplexes, (b) contacting the first aqueous composition with a reverse transcriptase enzyme under conditions such that at least two cDNA transcripts comprising the first unique DNA barcode are generated within the first aqueous composition, wherein the volume of the first aqueous composition is less than 5 nanoliters;

(c) removing unincorporated DNA barcode sequences; and (d) sequencing each of the at least two cDNA transcripts; thereby identifying at least two gene sequences from at least one cell.

According to one item, the methods of the invention further comprise the step of amplifying each of the at least two cDNA transcripts prior to sequencing each of the at least two cDNA transcripts.

According to one item, the amplifying step is performed in a multiplex reaction, a separated polymerase chain reaction (PCR), or a linear amplification.

According to one item, the linear amplification is an in vitro transcription.

According to a further item, the methods of the invention further comprise the step of releasing each of the at least two DNA/RNA duplexes from the first carrier within the first aqueous composition prior to amplifying each of the at least two cDNA transcripts.

According to another item, the methods of the invention further comprise the step of releasing each of the at least two DNA/RNA duplexes from the first carrier within the first aqueous composition after amplifying each of the at least two cDNA transcripts.

According to one item, the methods of the invention further comprise the step of releasing each of the at least two DNA/RNA duplexes from the first carrier within the first aqueous composition prior to contacting the first aqueous composition with the reverse transcriptase enzyme.

According to a further item, the first aqueous composition further comprises a first lysing composition.

According to a further item, the first aqueous composition further comprises a first reverse transcriptase composition.

According to a further item, the first cell is an immune cell.

According to a further item, the immune cell is a B cell, a T cell, or a hybridoma, preferably a B cell.

According to another item, the first cell is a mammalian cell.

According to another item, the first cell is a non-mammalian cell.

According to one item, the non-mammalian cell is a yeast cell.

According to another item, the non-mammalian cell is an avian cell.

According to another item, the non-mammalian cell is a shark cell.

According to a further item, the at least two RNA molecules comprise a first RNA molecule comprising a first target sequence and a second RNA molecule comprising a second target sequence.

According to a particular item, the first cell is an immune cell; the at least two RNA molecules comprise a first RNA molecule comprising a sequence that encodes a heavy chain variable region (VH) and a second RNA molecule comprising a sequence that encodes a light chain variable region (VL); the at least two DNA/RNA duplexes comprise a first DNA/RNA duplex comprising a sequence that encodes a heavy chain variable region (VH) and a second DNA/RNA duplex comprising a sequence that encodes a light chain variable region (VL); and the at least two cDNA transcripts comprising the first unique DNA barcode comprise a first cDNA transcript comprises a sequence that encodes a VH and the first unique DNA barcode sequence and a second cDNA transcript comprises a sequence that encodes a light chain variable region (VL) and the first unique DNA barcode sequence.

According to a particular item, the first cell is an immune cell; the at least two RNA molecules comprise a first RNA molecule comprising a sequence that encodes a T-cell Receptor α-chain (TCR-α) and a second RNA molecule comprising a sequence that encodes a T-cell Receptor β-chain (TCR-β);

the at least two DNA/RNA duplexes comprise a first DNA/RNA duplex comprising a sequence that encodes a TCR-α and a second DNA/RNA duplex comprising a sequence that encodes a TCR-β; and the at least two cDNA transcripts comprising the first unique DNA barcode comprise a first cDNA transcript comprises a sequence that encodes a TCR-α and the first unique DNA barcode sequence and a second cDNA transcript comprises a sequence that encodes TCR-β and the first unique DNA barcode sequence.

According to one item, the at least two RNA molecules comprise a first RNA molecule comprising a polyA sequence and a second RNA molecule comprising a polyA sequence.

According to a further item, the first unique DNA barcode sequence comprises a DNA sequence comprising, from 5' to 3', a first unique barcode sequence, wherein the barcode sequence is single- or double-stranded, and a first priming sequence for reverse-transcription, wherein the priming sequence is single-stranded.

According to a further item, the first unique DNA barcode sequence further comprises a linker sequence 5' to the first unique barcode sequence and the first priming sequence.

According to a further item, the method further comprises, (a) encapsulating at least a second cell, a second carrier linked to a plurality of a second unique DNA barcode, and a reverse transcriptase enzyme to form a second aqueous composition, under conditions such that the second cell releases at least two RNA molecules within the second aqueous composition;

under conditions such that the second unique DNA barcode hybridizes to each of the at least two RNA molecules to form at least two DNA/RNA duplexes, and under conditions such that at least two cDNA transcripts comprising the second unique DNA barcode are generated within the second aqueous composition, wherein the volume of the second aqueous composition is less than 5 nanoliters;

(b) removing unincorporated DNA barcode sequences; and (c) sequencing each of the at least two cDNA transcripts.

According to another item, the method further comprises, (a) encapsulating at least a second cell and a second carrier linked to a plurality of a second unique DNA barcode to form a second aqueous composition, under conditions such that the second cell releases at least two RNA molecules within the second aqueous composition; and under conditions such that the second unique DNA barcode hybridizes to each of the at least two RNA molecules to form at least two DNA/RNA duplexes, (b) contacting the second aqueous composition with a reverse transcriptase enzyme under conditions such that at least two cDNA transcripts comprising the second unique DNA barcode are generated within the second aqueous composition, wherein the volume of the second aqueous composition is less than 5 nanoliters;

(b) removing unincorporated DNA barcode sequences; and (c) sequencing each of the at least two cDNA transcripts.

According to one item, the methods of the invention further comprise the step of amplifying each of the at least two cDNA transcripts prior to sequencing each of the at least two cDNA transcripts.

According to one item, said amplifying step is performed in a multiplex reaction, a separated polymerase chain reaction (PCR), or a linear amplification.

According to a further item, the linear amplification is an in vitro transcription.

According to another item, the methods of the invention further comprise the step of releasing each of the at least two DNA/RNA duplexes from the second carrier within the second aqueous composition prior to amplifying each of the at least two cDNA transcripts.

According to another item, the methods of the invention further comprise the step of releasing each of the at least two DNA/RNA duplexes from the second carrier within the second aqueous composition after amplifying each of the at least two cDNA transcripts.

According to further item, the methods of the invention further comprise the step of releasing each of the at least two DNA/RNA duplexes from the second carrier within the second aqueous composition prior to contacting the second aqueous composition with the reverse transcriptase enzyme.

According to one item, the second aqueous composition further comprises a second lysing composition.

According to another item, the second aqueous composition further comprises a second reverse transcriptase composition.

According to a further item, the second cell is an immune cell.

According to a further item, the immune cell is a B cell, a T cell, or a hybridoma, preferably a B cell.

According to another item, the second cell is a mammalian cell.

According to another item, the second cell is a non-mammalian cell as defined according to one of the items herein above.

According to one particular item, the second cell is an immune cell; the at least two RNA molecules comprise a first RNA molecule comprising a sequence that encodes a heavy chain variable region (VH) and a second RNA molecule comprising a sequence that encodes a light chain variable region (VL);

the at least two DNA/RNA duplexes comprise a first DNA/RNA duplex comprising a sequence that encodes a heavy chain variable region (VH) and a second DNA/RNA duplex comprising a sequence that encodes a light chain variable region (VL); and the at least two cDNA transcripts comprising the second unique DNA barcode comprise a first cDNA transcript comprises a sequence that encodes a VH and the second unique DNA barcode sequence and a second cDNA transcript comprises a sequence that encodes a light chain variable region (VL) and the second unique DNA barcode sequence.

According to one further particular item, the second cell is an immune cell;

the at least two RNA molecules comprise a first RNA molecule comprising a sequence that encodes a T-cell Receptor α-chain (TCR-α) and a second RNA molecule comprising a sequence that encodes a T-cell Receptor β-chain (TCR-β);

the at least two DNA/RNA duplexes comprise a first DNA/RNA duplex comprising a sequence that encodes a TCR-α and a second DNA/RNA duplex comprising a sequence that encodes a TCR-β; and the at least two cDNA transcripts comprising the first unique DNA barcode comprise a first cDNA transcript comprises a sequence that encodes a TCR-α and the first unique DNA barcode sequence and a second cDNA transcript comprises a sequence that encodes TCR-β and the first unique DNA barcode sequence.

According to one further item, the second unique DNA barcode sequence comprises a DNA sequence comprising, from 5' to 3', a second unique barcode sequence, wherein the barcode sequence is single- or double-stranded and a second priming sequence for reverse-transcription, wherein the priming sequence is single-stranded.

According to one item, the first lysing composition and the second lysing composition are identical.

According to one item, the first unique DNA barcode sequence and the second unique DNA barcode sequence are different.

According to one item, the volume of the first aqueous composition is between about 10 and 5000 picoliters, inclusive of the endpoints. For example, the volume of the first aqueous composition may be 0.01, 0.05, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0 nanoliters or any amount in between.

According to one particular item, the volume of the first aqueous composition has has a volume of less than 3 nL. According to a more particular item, the volume of the first aqueous composition has a volume of less than 2.5 nL, less than 2 nL, less than 1.5 nL, less than 1 nL, less than 0.5 nL, for example 0.1 nL to 3 nL, 0.5 nL to 3 nL, 1 nL to 3 nL, typically, 0.1 nL, 0.5 nL, 1 nL, 1.2 nL, 1.4 nL, 1.6 nL, 1.8 nL, 2.0 nL, 2.2 nL, 2.4 nL, 2.6 nL, 2.8 nL, 3 nL.

According to one item, the volume of the second aqueous composition is between about 10 and 5000 picoliters, inclusive of the endpoints. For example, the volume of the second aqueous composition of the disclosure may be 0.01, 0.05, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0 nanoliters or any amount in between.

According to one particular item, the volume of the second aqueous composition has a volume of less than 3 nL. According to a more particular item, the volume of the second aqueous composition has a volume of less than 2.5 nL, less than 2 nL, less than 1.5 nL, less than 1 nL, less than 0.5 nL, for example 0.1 nL to 3 nL, 0.5 nL to 3 nL, 1 nL to 3 nL, typically, 0.1 nL, 0.5 nL, 1 nL, 1.2 nL, 1.4 nL, 1.6 nL, 1.8 nL, 2.0 nL, 2.2 nL, 2.4 nL, 2.6 nL, 2.8 nL, 3 nL.

According to one item, the concentration of the first unique DNA barcode sequence in the first aqueous composition is at least or preferably more than 100 nM.

According to one item, the concentration of the second unique DNA barcode sequence in the second aqueous composition is at least or preferably more than 100 nM.

According to one item, the first lysing composition and/or the second lysing composition comprise magnesium chloride, a detergent, a buffered solution, and an RNAse inhibitor.

According to one item, the magnesium chloride is at a concentration of between 1 mM to 20 mM, inclusive of the endpoints.

According to one item, the detergent is selected from the group consisting of Triton-X-100, Nonidet P40, and Tween-20.

According to one item, the detergent is at a concentration of 0.1% to 10%, inclusive of the endpoints.

According to one item, the buffered solution is selected form the group consisting of Tris-HCl, Hepes-KOH and Pipes-NaOH.

According to one further item, the RNase inhibitor is selected from the group consisting of RNase OUT, IN, and SuperIN RNase.

According to one item, the first reverse transcriptase composition and/or the second reverse transcriptase composition comprise(s) a protease inhibitor, dNTPs and DTT.

According to one item, the protease inhibitor comprises a plurality of protease inhibitors.

According to one item, the protease inhibitor comprises one or more of Leupeptin hemisulfate salt, pepstatin A, AEBSF, Aprotinin, Bestatin hydrochloride, E-64 and PMSF.

According to one item, the reverse transcriptase enzyme is Superscriptase I, Superscriptase II, Superscriptase III, Superscriptase IV, Moloney Leukemia RT, SmartScribe RT or MultiScribe RT.

According to one item, removing unincorporated DNA barcode sequences comprises contacting the first aqueous composition to a purification substrate wherein the purification substrate removes the unincorporated DNA barcode sequences.

According to another item, removing unincorporated DNA barcode sequences comprises contacting the second aqueous composition to a purification substrate wherein the purification substrate removes the unincorporated DNA barcode sequences.

According to one item, the purification substrate comprises beads or particles.

According to one item, the beads or particles form a column.

According to one item, sequencing each of the at least two cDNA transcripts comprises performing a next generation sequencing (NGS) protocol on a sequencing library.

According to one item, the NGS protocol comprises loading an amount of the sequencing library between 8 pM to 14 pM per flow cell of a reagent kit.

According to one item, the NGS sequencing protocol further comprises the step of adding 10-25% PhiX to the amount of the sequencing library or to the flow cell of the reagent kit.

According to one item, the methods of the invention further comprise inserting the sequence of the first cDNA transcript and the sequence of the second cDNA transcript into an expression vector.

The term "Vector" as used in context of these items includes shuttle and expression vectors. Typically, the plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells.

According to one item, the methods of the invention further comprise the steps of contacting the first cDNA transcript and the second cDNA transcript to a sequencing library and amplifying at least two sequences of interest from the sequencing library that correspond to the first cDNA transcript and the second cDNA transcript, respectively.

According to one item, the methods of the invention further comprise inserting the first sequence of interest corresponding to the first cDNA transcript and the sequence of interest corresponding to the second cDNA transcript into an expression vector.

According to one item, the methods of the invention further comprise expressing the expression vector in a host cell, thereby producing a recombinant polypeptide.

According to one item, the host cell is a mammalian cell.

According to one item, the mammalian cell s a 293, 293T, HeLa, CHO or U2OS cell.

According to one item, the first aqueous composition is a droplet.

According to one item, the first aqueous composition is contained in a first container or any compartment thereof.

According to one item, the first container or any compartment thereof is a plate, well, tube, channel, nano well, nano tube, or nano channel.

According to one item, the second aqueous composition is a droplet.

According to one item, the second aqueous composition is contained in a second container or any compartment thereof.

According to one item, the second container or any compartment thereof is a plate, well, tube, channel, nano well, nano tube, or nano channel.

According to one item, the first container has a maximal volume of between 3 to 5 nanoliters, inclusive of the endpoints.

According to one item, the first container and/or the second container has a maximal volume of between 3 to 5 nanoliters, inclusive of the endpoints.

According to one item, the first carrier is a solid support or a liquid carrier.

According to one item, the solid support is a bead, a hydrogel bead, a polystyrene bead, a magnetic particle, or a surface.

According to one item, the liquid carrier is an emulsion, a solution, a buffer, an aqueous solution, a non-aqueous solution.

According to one item, the second carrier is a solid support or a liquid carrier.

According to one item, the solid support is a bead, a hydrogel bead, a polystyrene bead, a magnetic particle, or a surface.

According to one item, the liquid carrier is an emulsion, a solution, a buffer, an aqueous solution, a non-aqueous solution.

Throughout the instant application, the term "and/or" is a grammatical conjunction that is to be interpreted as encompassing that one or more of the cases it connects may occur. For example, the wording "error detection and/or correction" in the phrase "the sequences allow for error detection and/or correction" indicates that the sequences may allow for error detection and the sequence may allow for error correction or the sequences may allow for error detection or the sequence may allow for error correction.

As used in this specification and the appended claims, the singular forms "a," "an" and "the" include plural references, such as a plurality of the object referred to, unless the content clearly dictates otherwise.

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of").

In the entire description, features described in one section are entirely applicable to other sections of the instant description. For instance, the description referring to "primers" as given in the section "Method for capturing and barcoding single cell nucleic acid" is entirely applicable to the section called "Plurality of microfluidic droplets" and the section called "A method for preparing a plurality of microfluidic droplets" or, for example, the description referring to "at least one type of oligonucleotide" as given in the section "Method for capturing and barcoding single cell nucleic acid" is entirely applicable to the section called "Plurality of microfluidic droplets" and the section called "A method for preparing a plurality of microfluidic droplets".

The invention will now be described in more detail with reference to the following examples. All literature and patent documents cited herein are hereby incorporated by reference. While the invention has been illustrated and described in detail in the foregoing description, the examples are to be considered illustrative or exemplary and not restrictive.

FIGURES

Figure 3A:
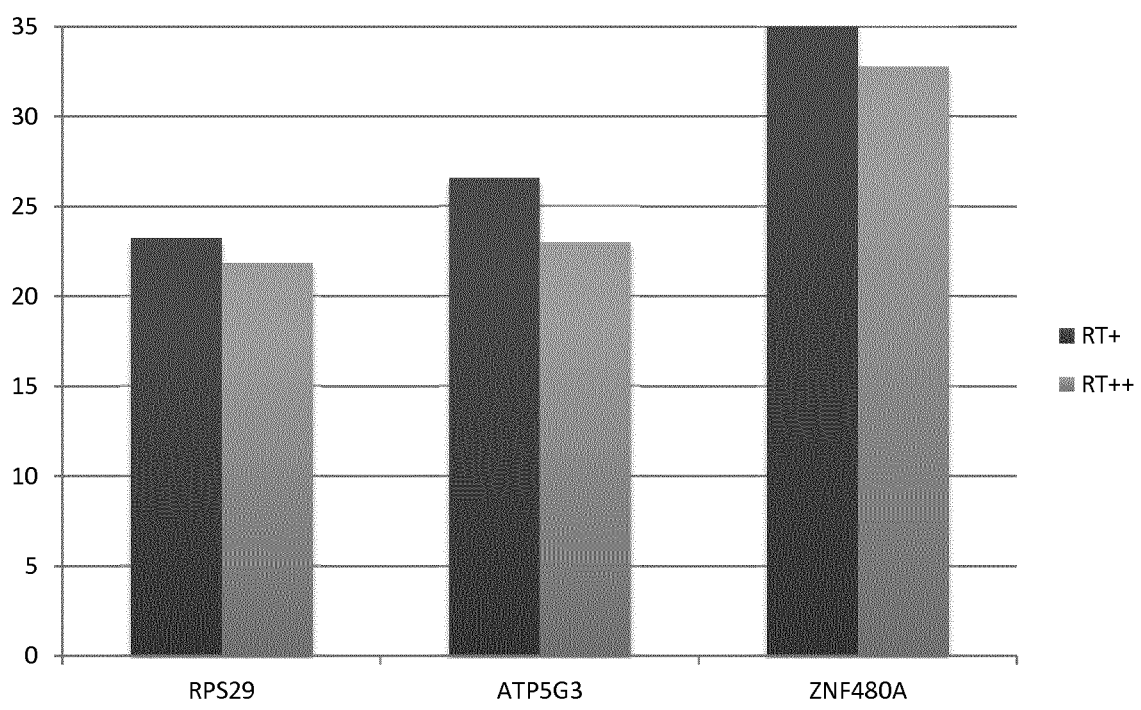
FIG. 3A is a graph depicting the changes in Cp value by increasing the reverse transcriptase (RT) concentration in a droplet-based experiment across three different genes (RPS29, ATP5G3 and ZNF480A).
Figure 3B:
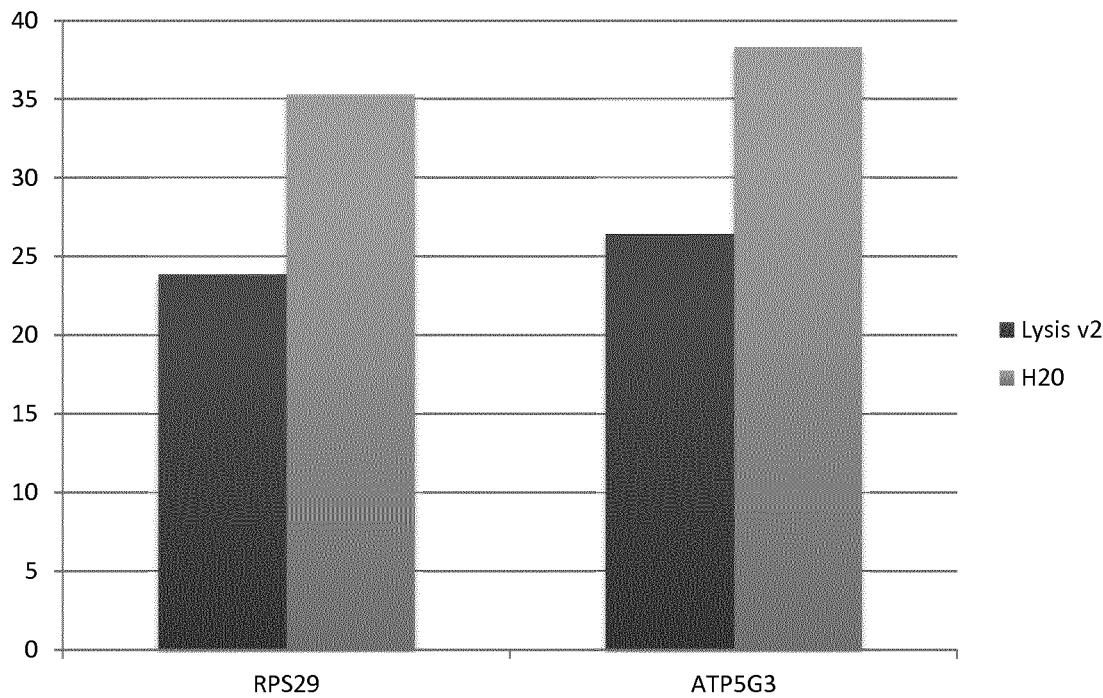
FIG. 3B is a graph depicting the impact of lysis buffer composition for efficient cDNA synthesis in a droplet-based experiment across two different genes (RPS29, ATP5G3).
Figures 3C, 3D:
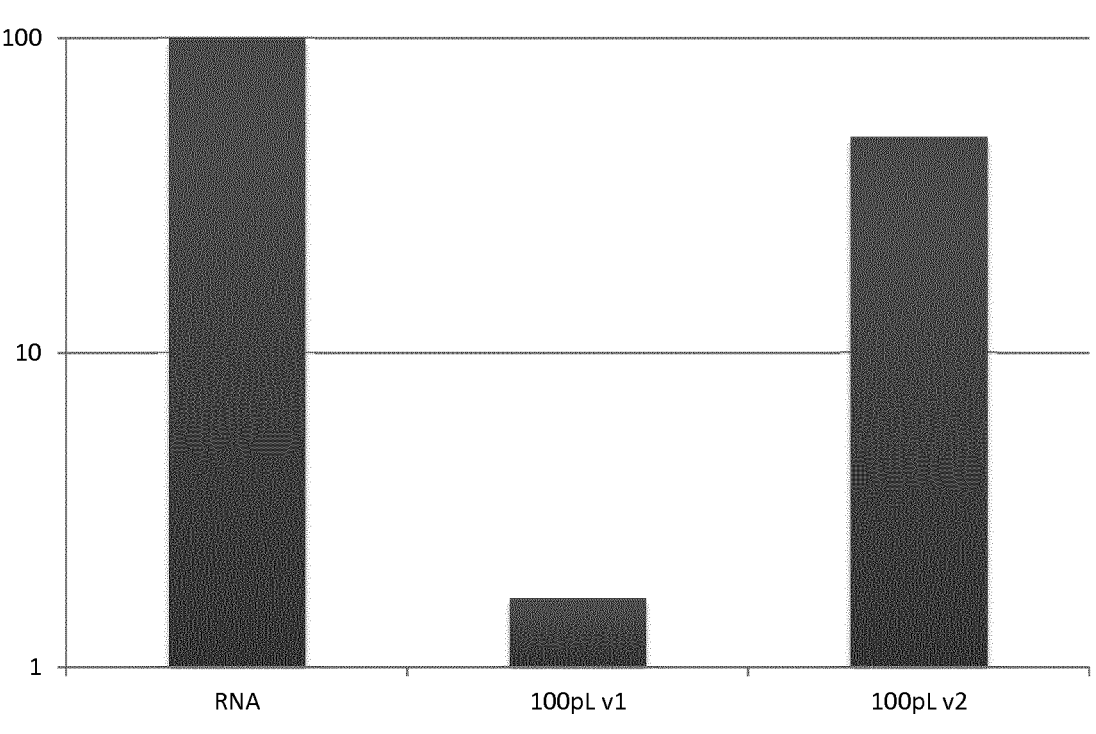
FIG. 3C is a graph recapitulating the impact of the changes in RT amount (FIG. 3A) and lysis conditions (FIG. 3B) in the efficiency of cDNA synthesis for the ATP5G3 gene.
FIG. 3D is a graph depicting the further impact of both increased drop volume and changes in the reverse transcription (RT) conditions in the efficiency of reverse transcription, measured by the Cp value for ATP5G3 gene. In this experiment, the amount of RT enzyme and RNase inhibitor were increased and the lysis buffer was altered.
Figure 3E:
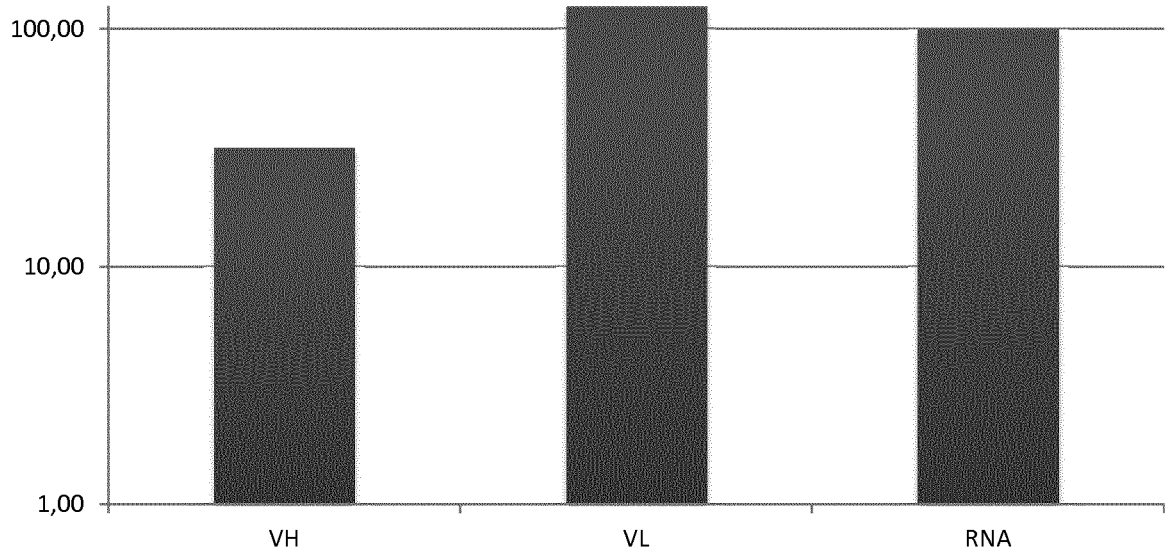

FIG. 3E is a graph depicting the percentage of RT efficiency of droplet-based approaches compared to purified RNA. The percentage of RT efficiency is above 100% for the immunoglobulin light chain variable genes and approximately 30% for the immunoglobulin heavy chain variable genes. The lower value for VH may be due to lower PCR efficiency on barcoded sample.

FIG. 4A is a series of gels depicting the results of a nested polymerase chain reaction (PCR) amplification of barcoded single cell transcripts encoding immunoglobulin variable heavy (VH) and variable light (VL) chains. The top gel is the first PCR reaction (VH amplicon on the left and VL amplicon on the right), the gel in the middle is the second PCR (VH amplicon on the left and VL amplicon on the right) and the bottom gel is the QC of the final PCR sequencing library product confirming the presence of Illumina NGS P5/P7 sequences and the presence of Light and Heavy chain associated barcode in the corresponding sequencing libraries.

Figure 4B:
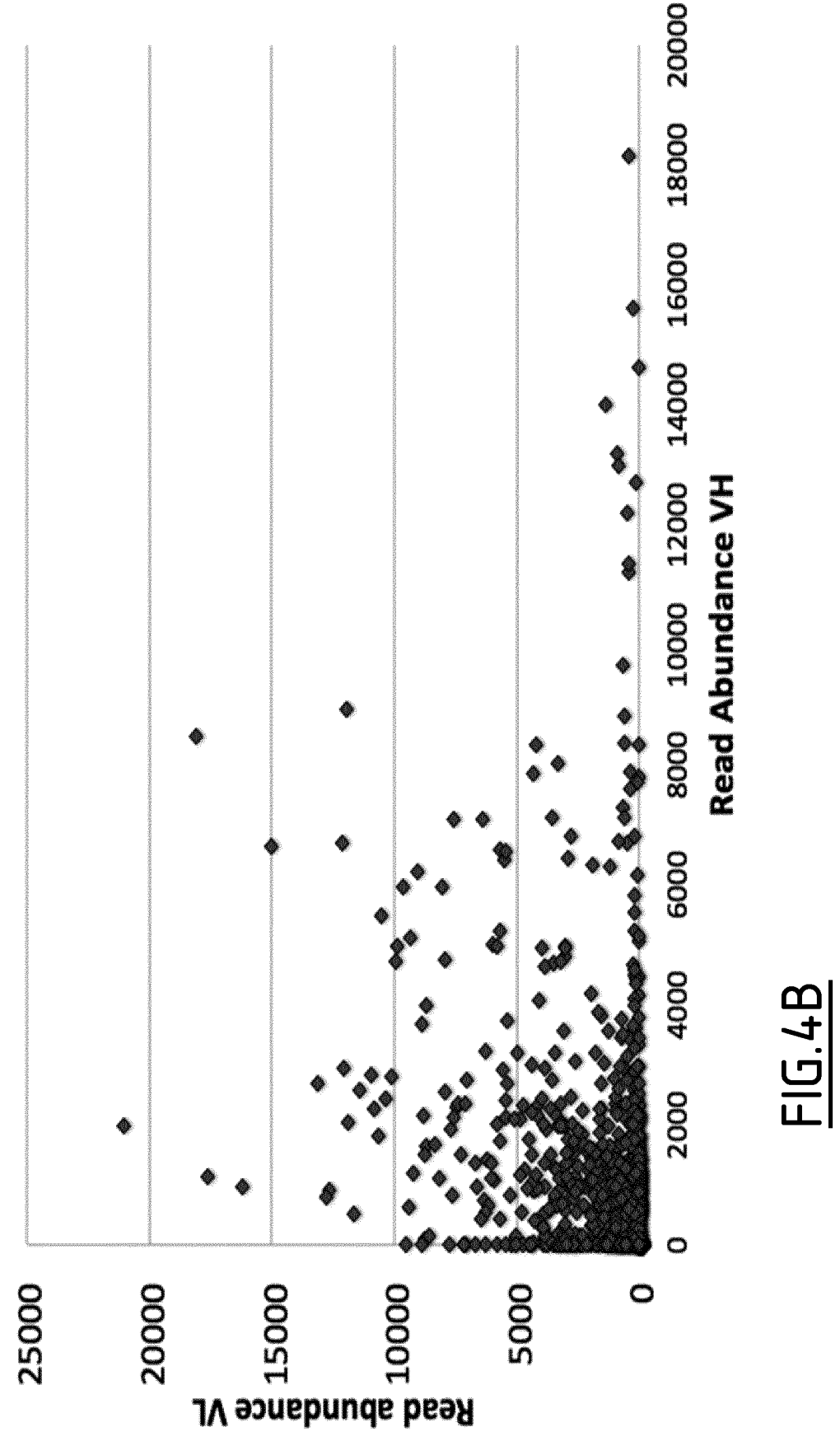

FIG. 4B is a graph depicting paired antibody sequence reads sharing the same barcode (i.e. coming from the same cells) plotted according to the number of VH reads (x axis) and VL reads (y axis).

Figures 4C, 4D:
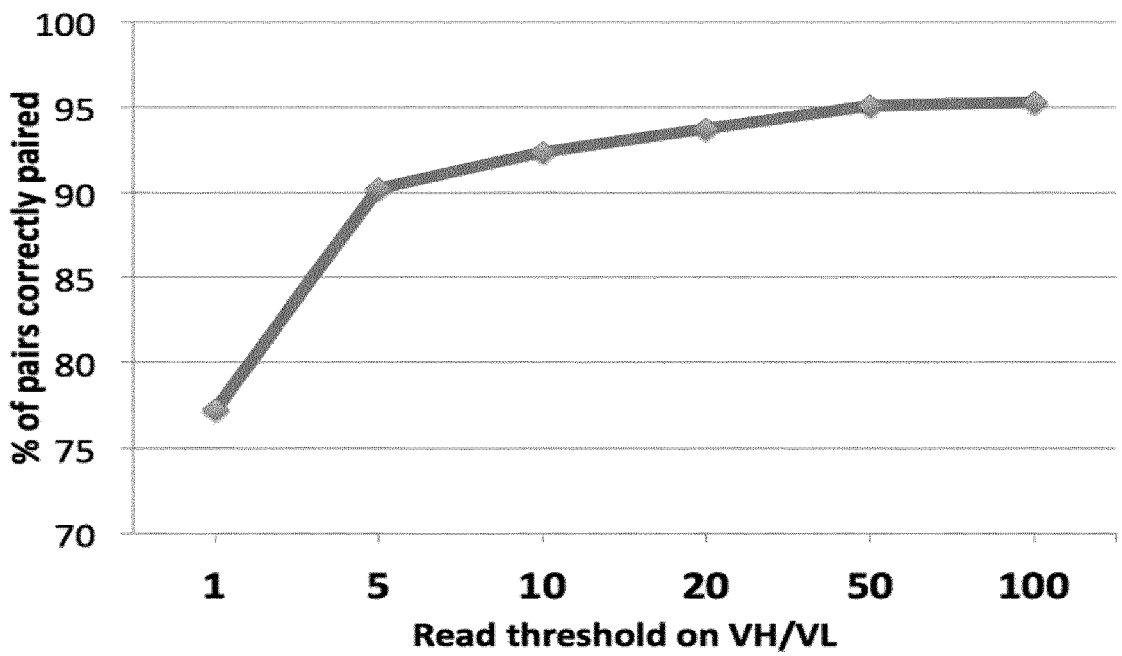

FIG. 4C is a graph depicting the rate of correct hybridoma VH/VL pairing as a function of read threshold for each VH/VL chain.

FIG. 4D is a chart depicting the number of hybridoma VH/VL pairs as a function of read threshold (for both chain)

Figure 5A:
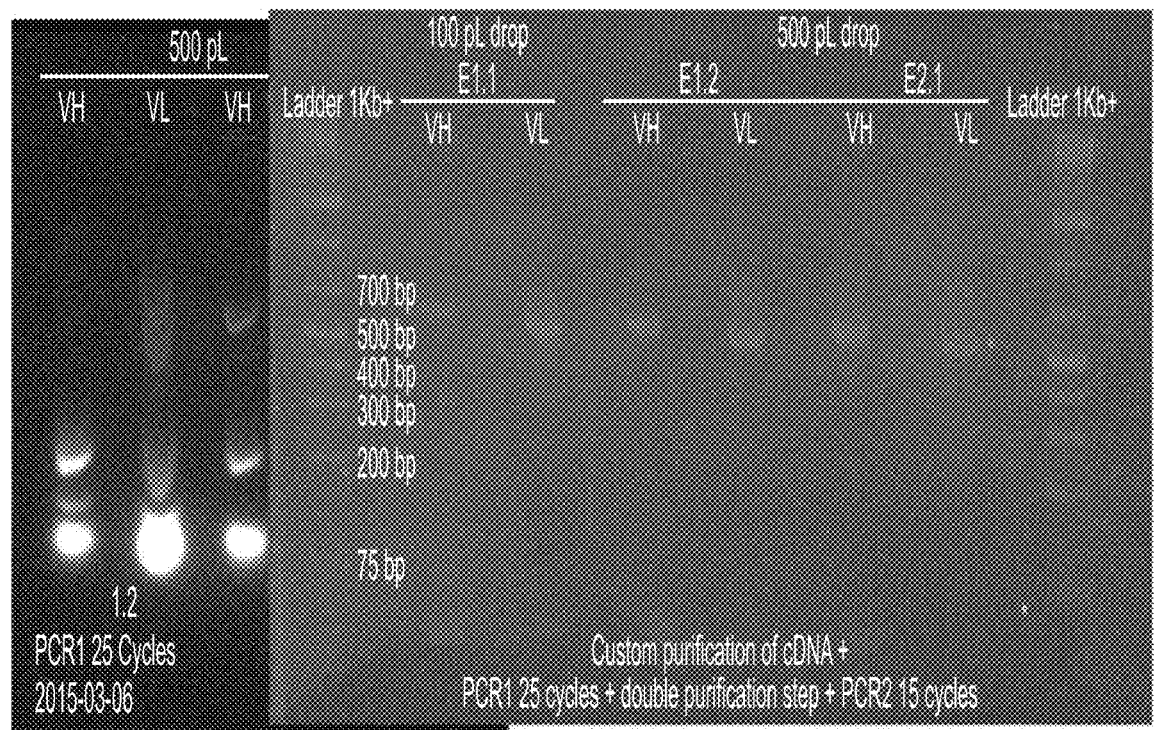

FIG. 5A is a pair of gels depicting the results of a nested polymerase chain reaction (PCR) amplification of barcoded single cell VH/VL.

Figure 5B:
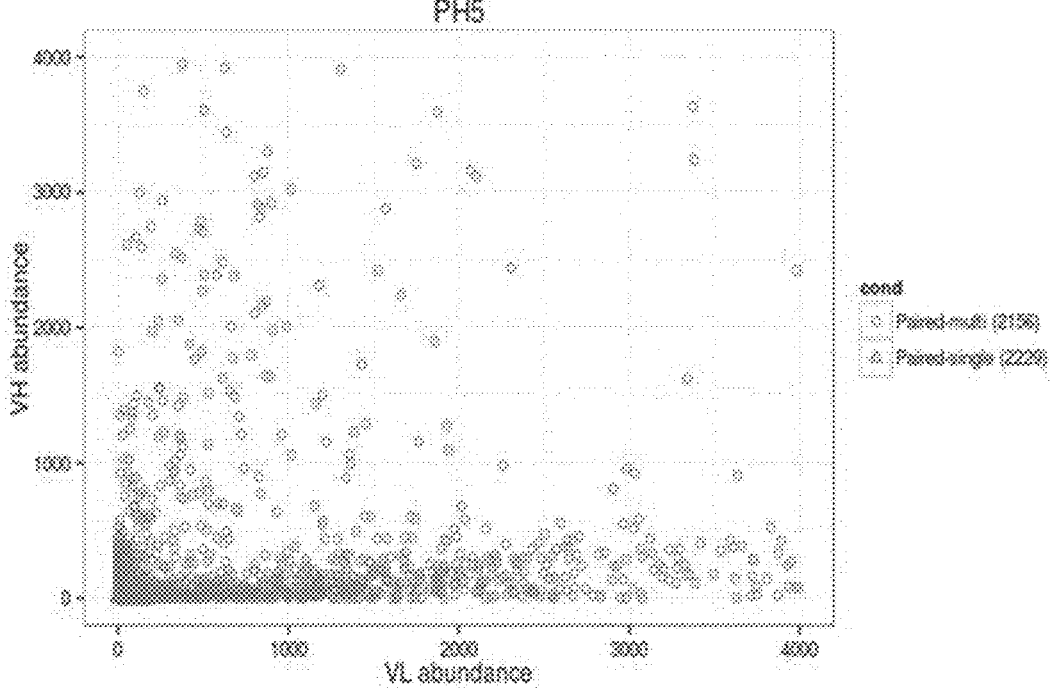

FIG. 5B is a graph depicting the number of VH and VL reads in the paired sequences.

Figure 5C:
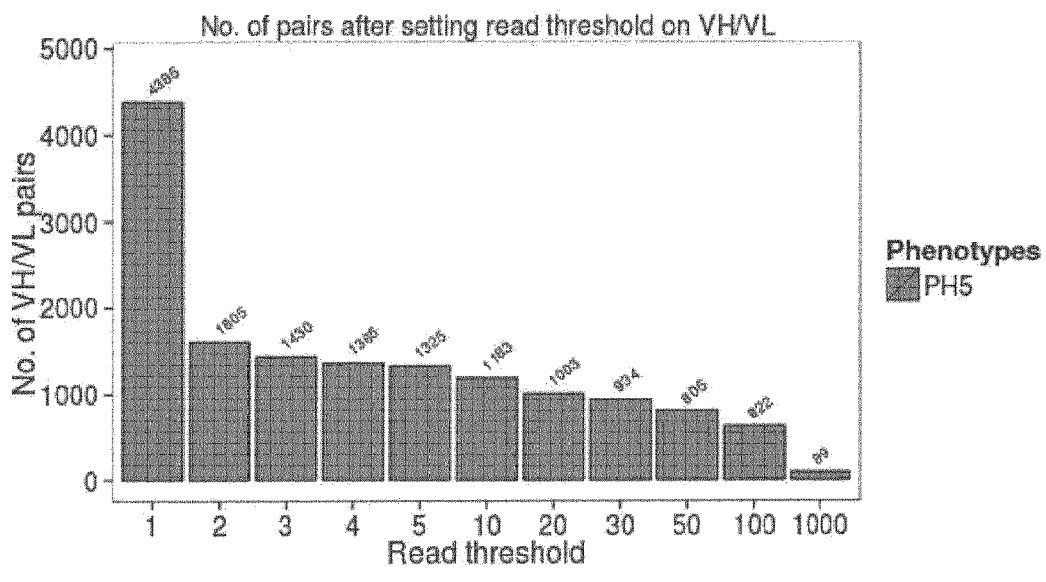

FIG. 5C is a graph depicting the number of hybridoma VH/VL pairings as a function of read threshold (for both VH and VL chains).

Figure 5D:
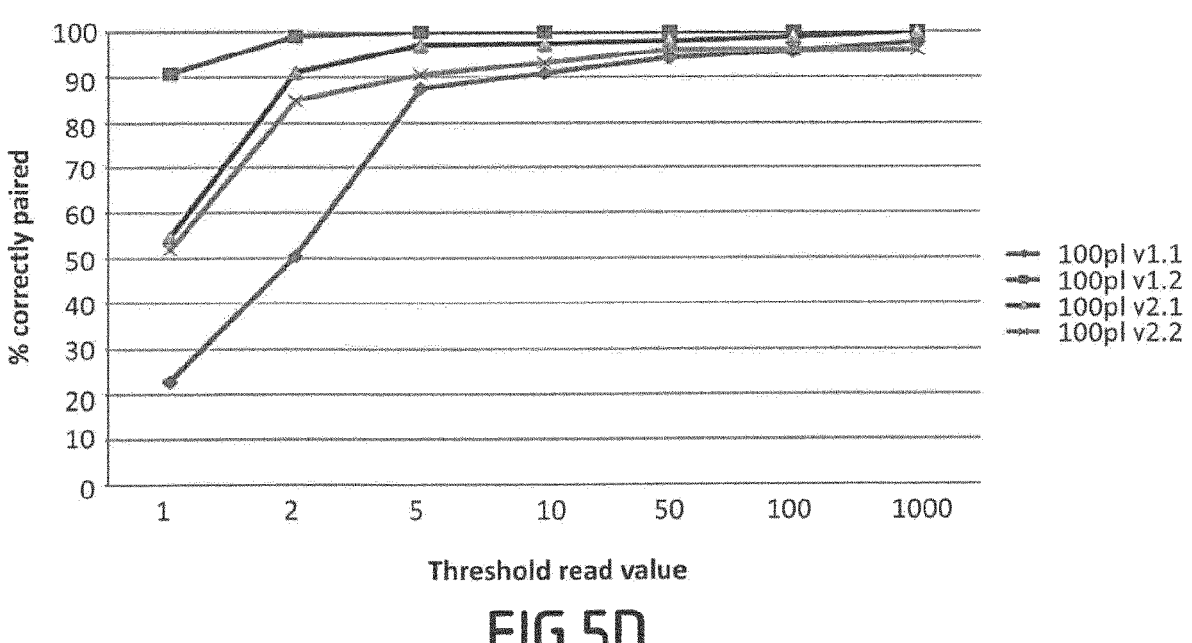

FIG. 5D is a graph depicting the number of correct hybridoma VH/VL pairings as a function of read threshold (for both VH and VL chains) and droplet volume and cDNA purification method.

Figure 5E:
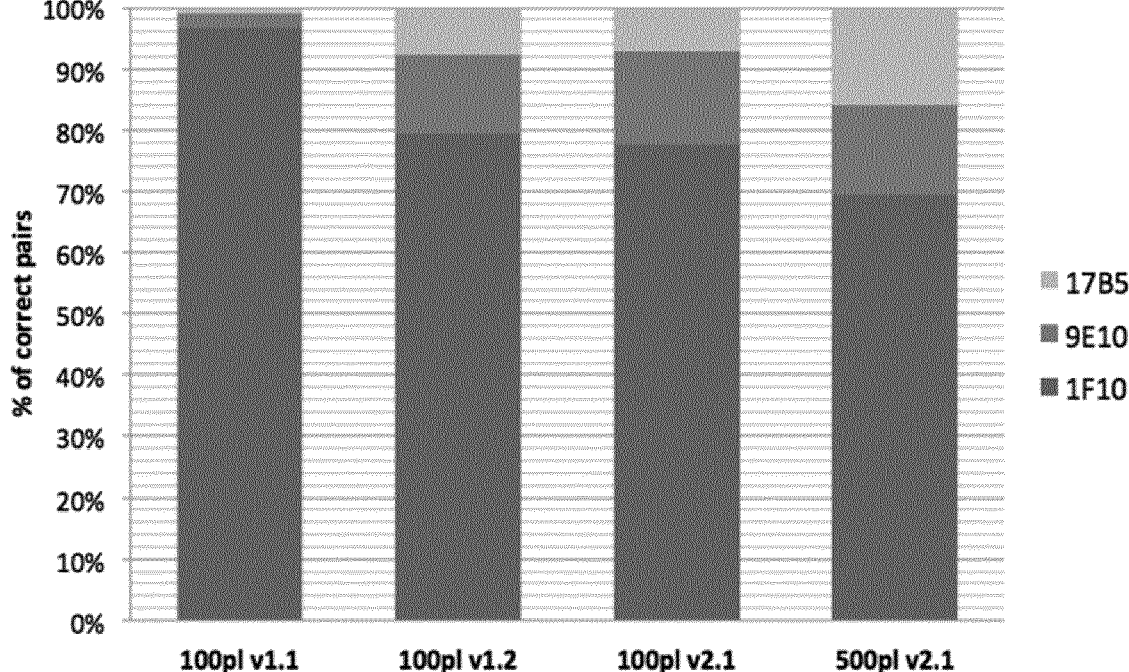

FIG. 5E is a graph depicting the distribution of recovered hybridoma pairs at a threshold of 10 reads per chain depending on droplet volume and purification method.

Figure 6A:
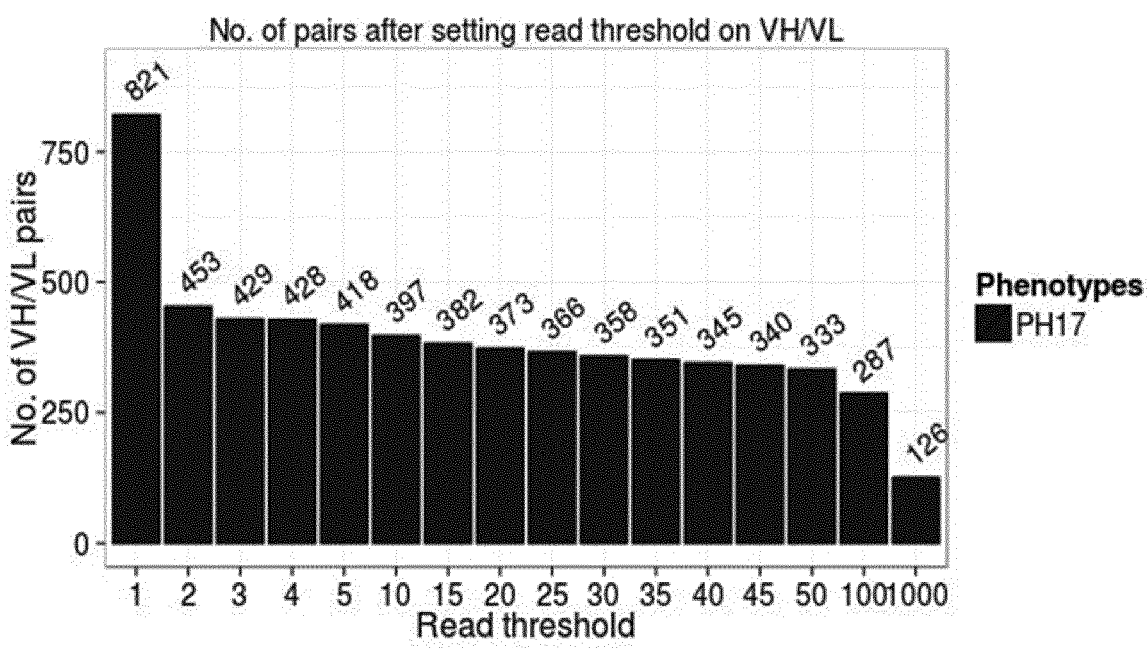

FIG. 6A is a graph depicting the number of VH/VL pairings from sorted B cells as a function of read threshold (for both VH and VL chains).

Figure 6B:
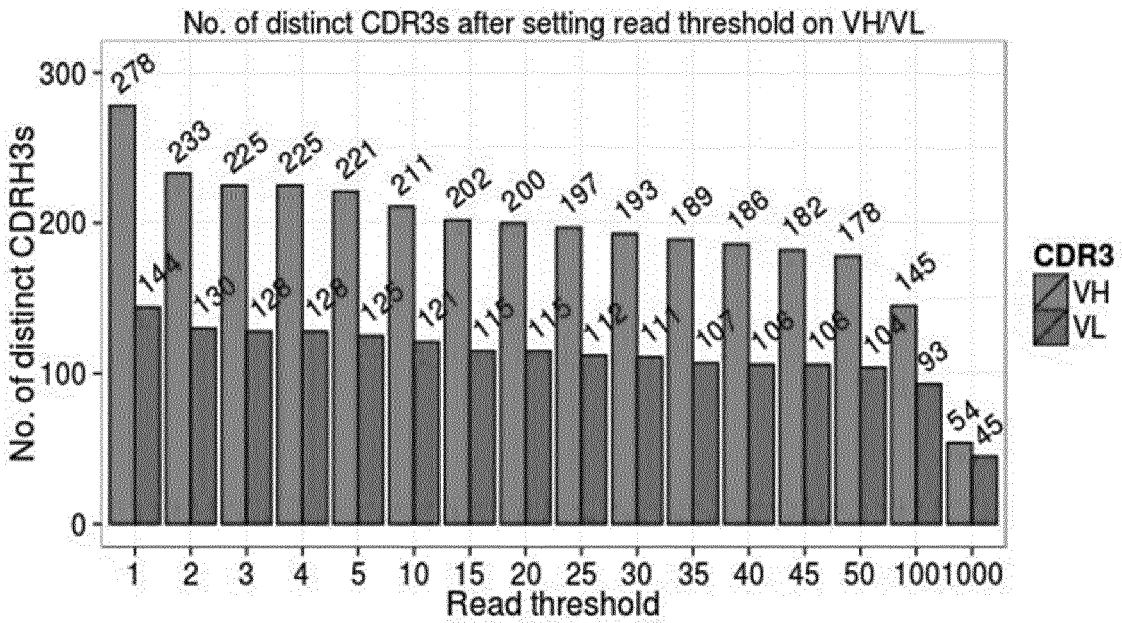

FIG. 6B is a graph depicting the number of distinct CDR3 sequences identified as a function of read threshold (for both VH and VL chains).

Figure 6C:
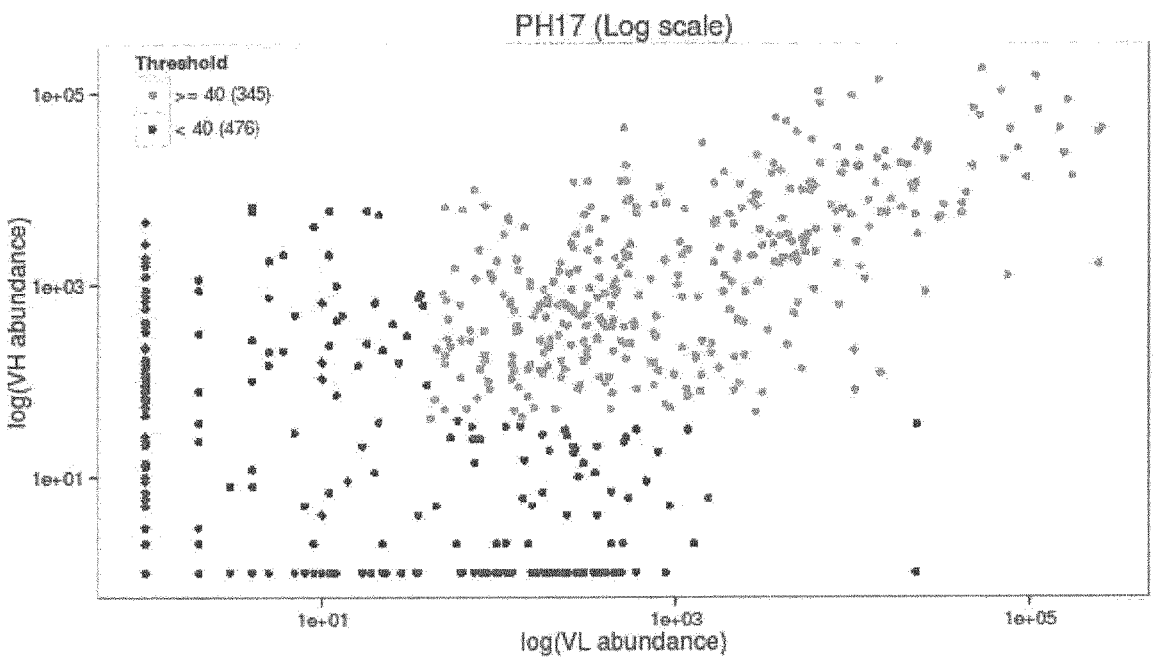

FIG. 6C is a graph depicting paired sequence reads sharing the same barcode (i.e., coming from the same cells) plotted according to the number of VH and VL reads.

Figure 6D:
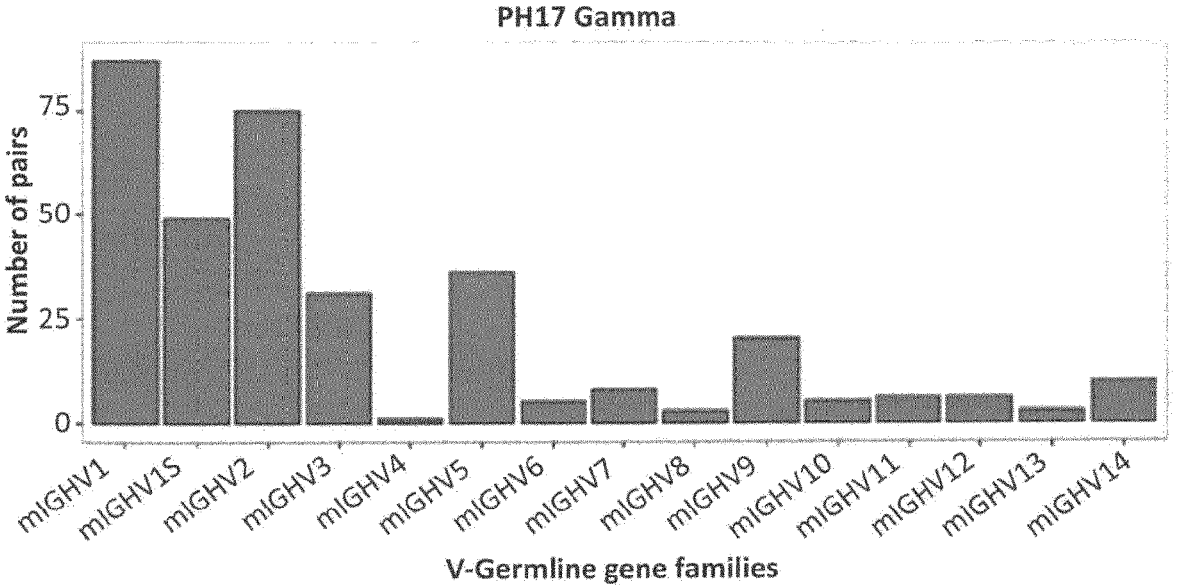

FIG. 6D is a graph depicting Heavy Variable gene usage in the paired sequences identified at a threshold of 40 reads per chain.

Figure 6E:
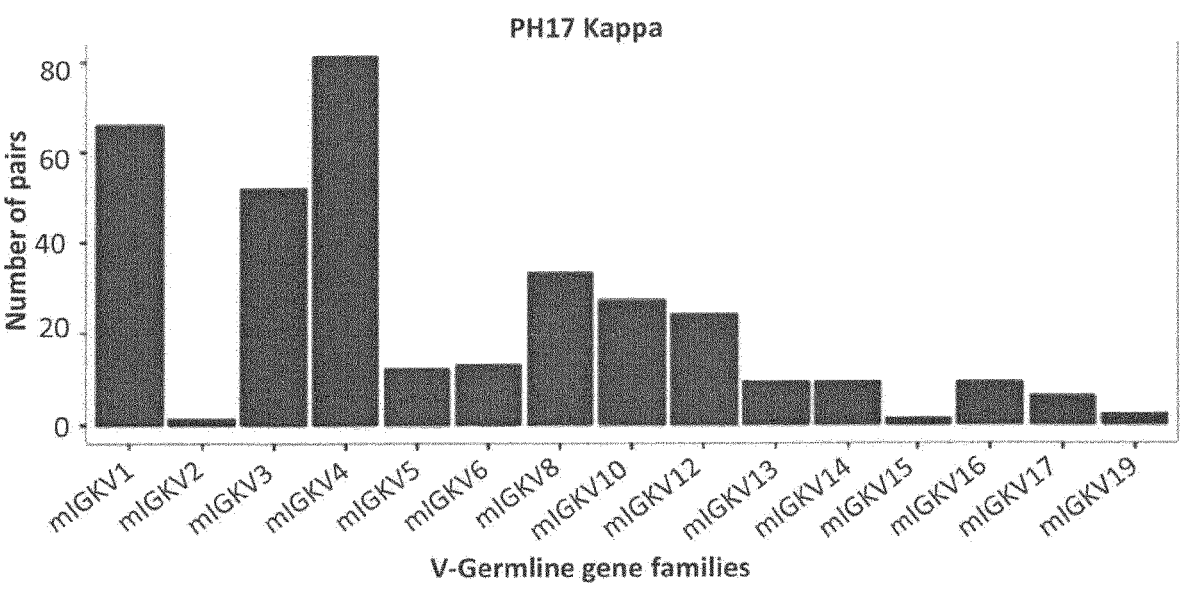

FIG. 6E is a graph depicting Light Kappa Variable gene usage in the paired sequences identified at a threshold of 40 reads per chain.

Figure 6F:
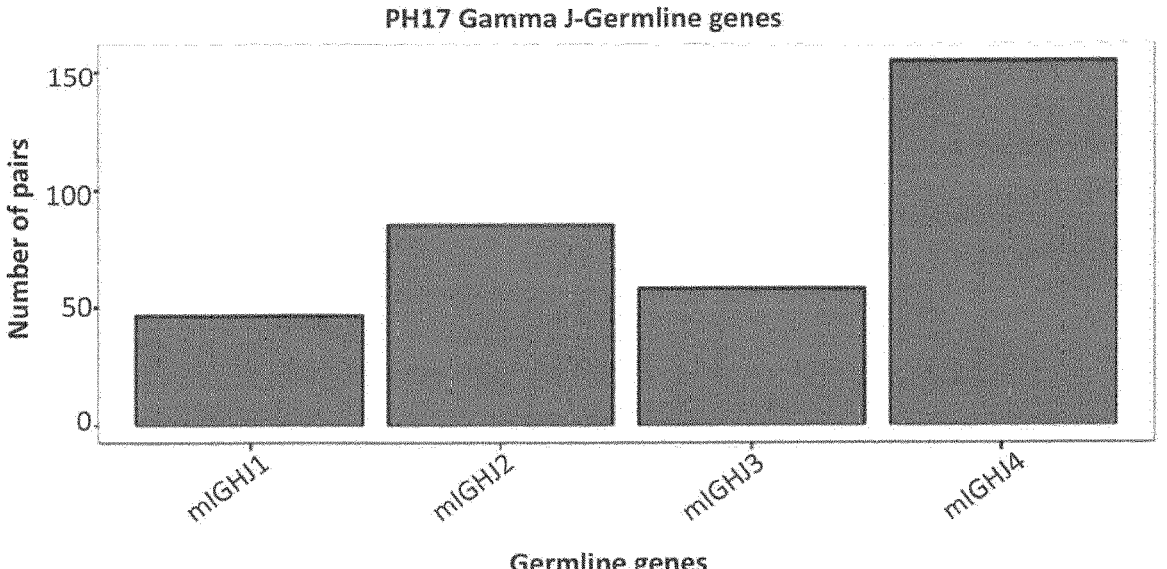

FIG. 6F is a graph depicting gamma J-germline gene usage in the paired sequences identified at a threshold of 40 reads per chain.

Figure 6G:
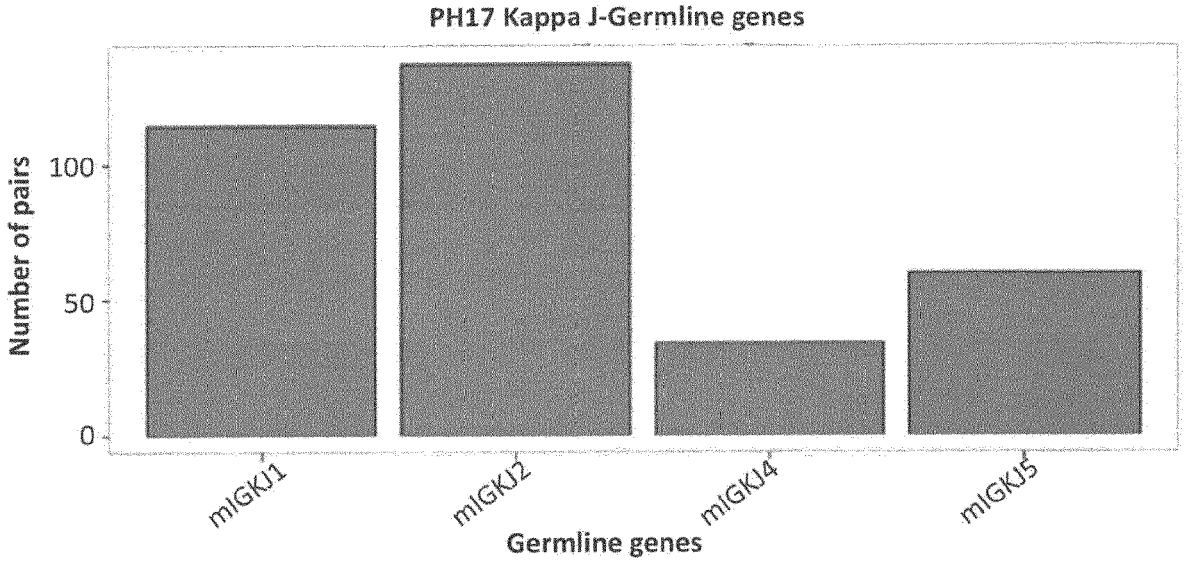

FIG. 6G is a graph depicting kappa J-germline gene usage in the paired sequences identified at a threshold of 40 reads per chain.

Figure 7:
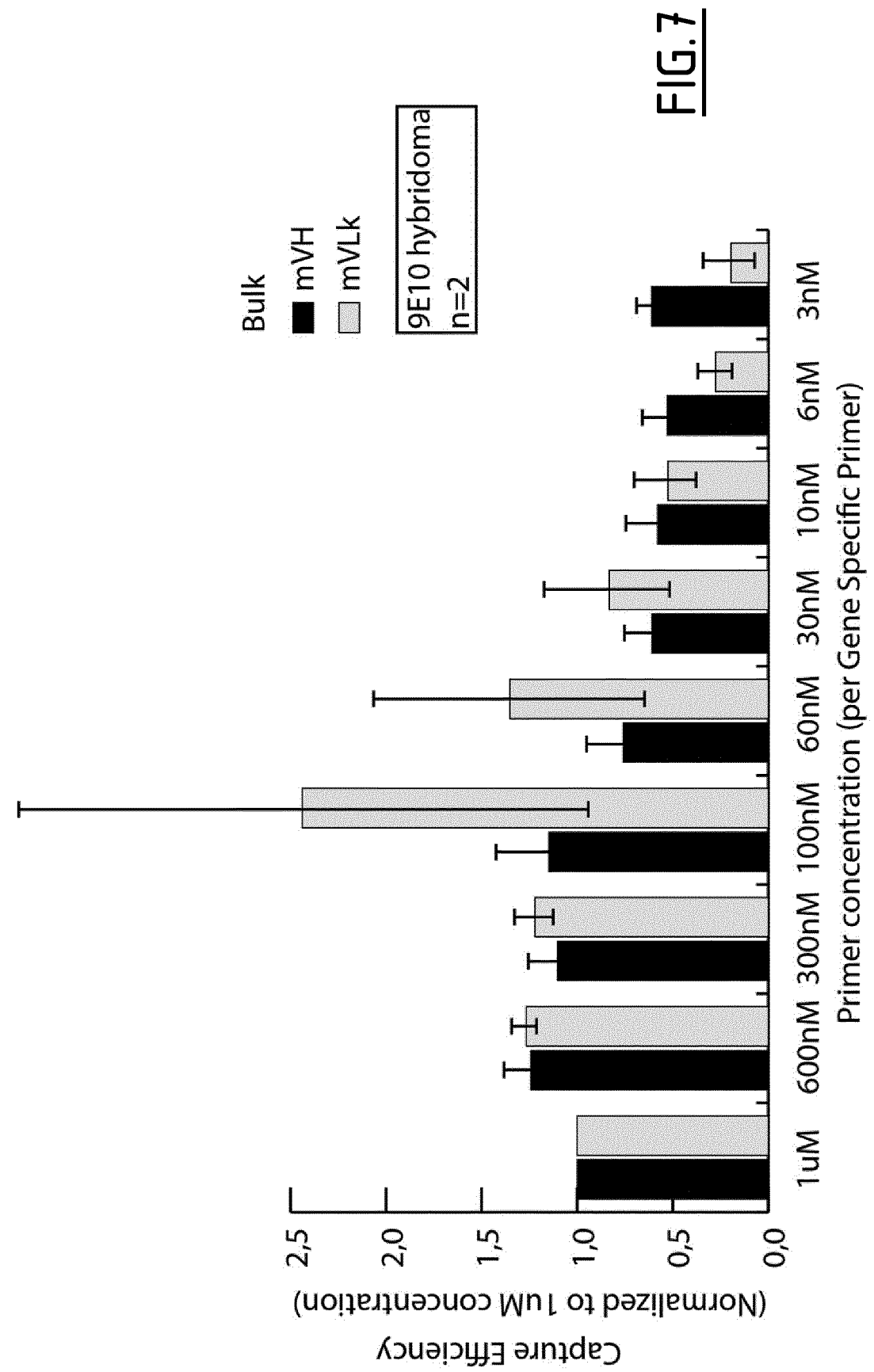

FIG. 7 is a graph depicting capture efficiency of mouse immonuglobulin variable heavy (VH) and variable light (VL) chains reverse transcription for different primer concentrations.

Figures 8A, 8B:
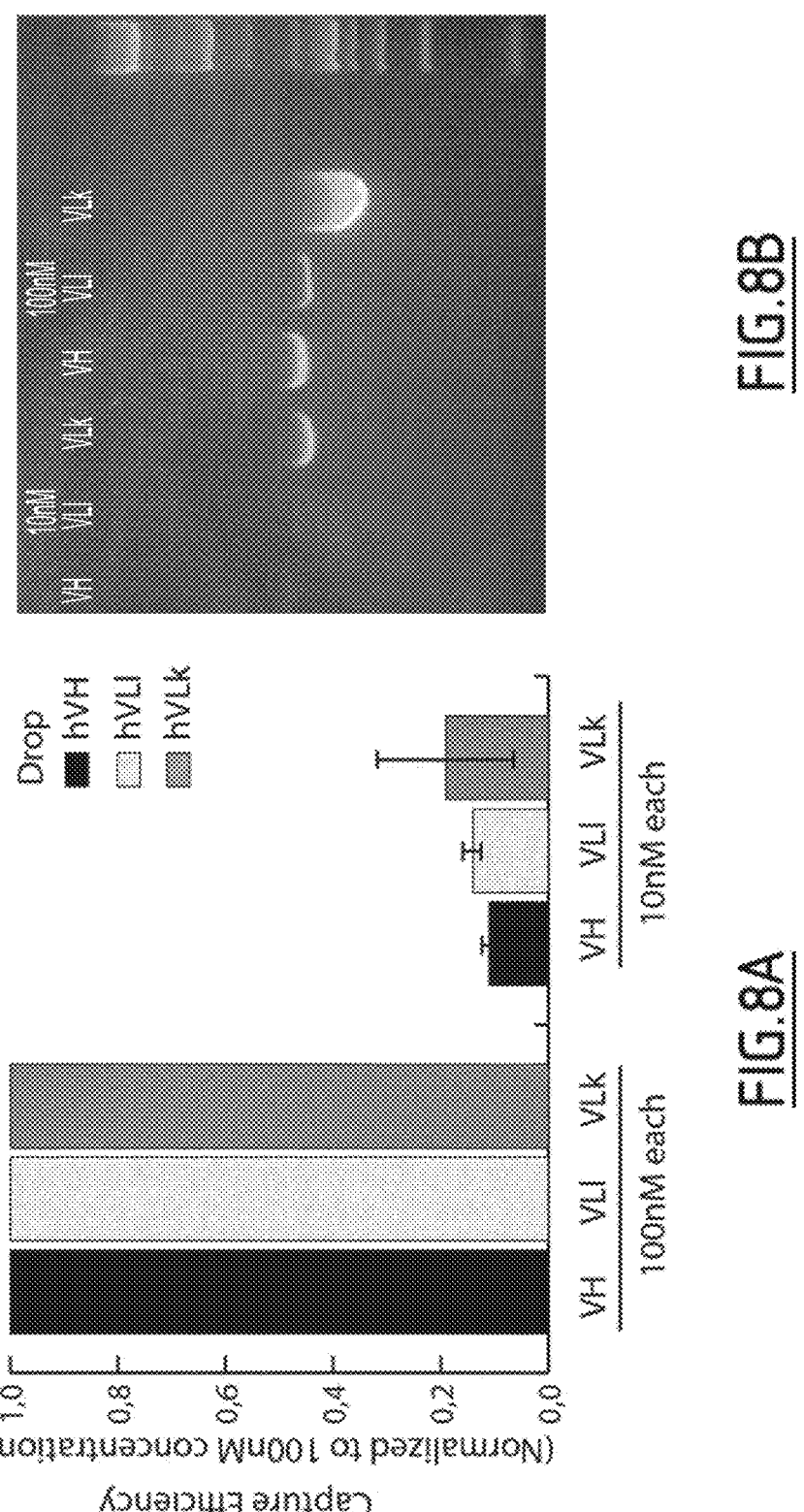

FIG. 8A) is a graph depicting capture efficiency of mouse immonuglobulin variable heavy (VH) and variable light kappa (VLk) and lambda (VLl) chains reverse transcription for different primer concentrations (10 nM and 100 nM) B) is the picture of the agarose gel loaded with samples of the reverse transcription performed in A)

Figure 9:
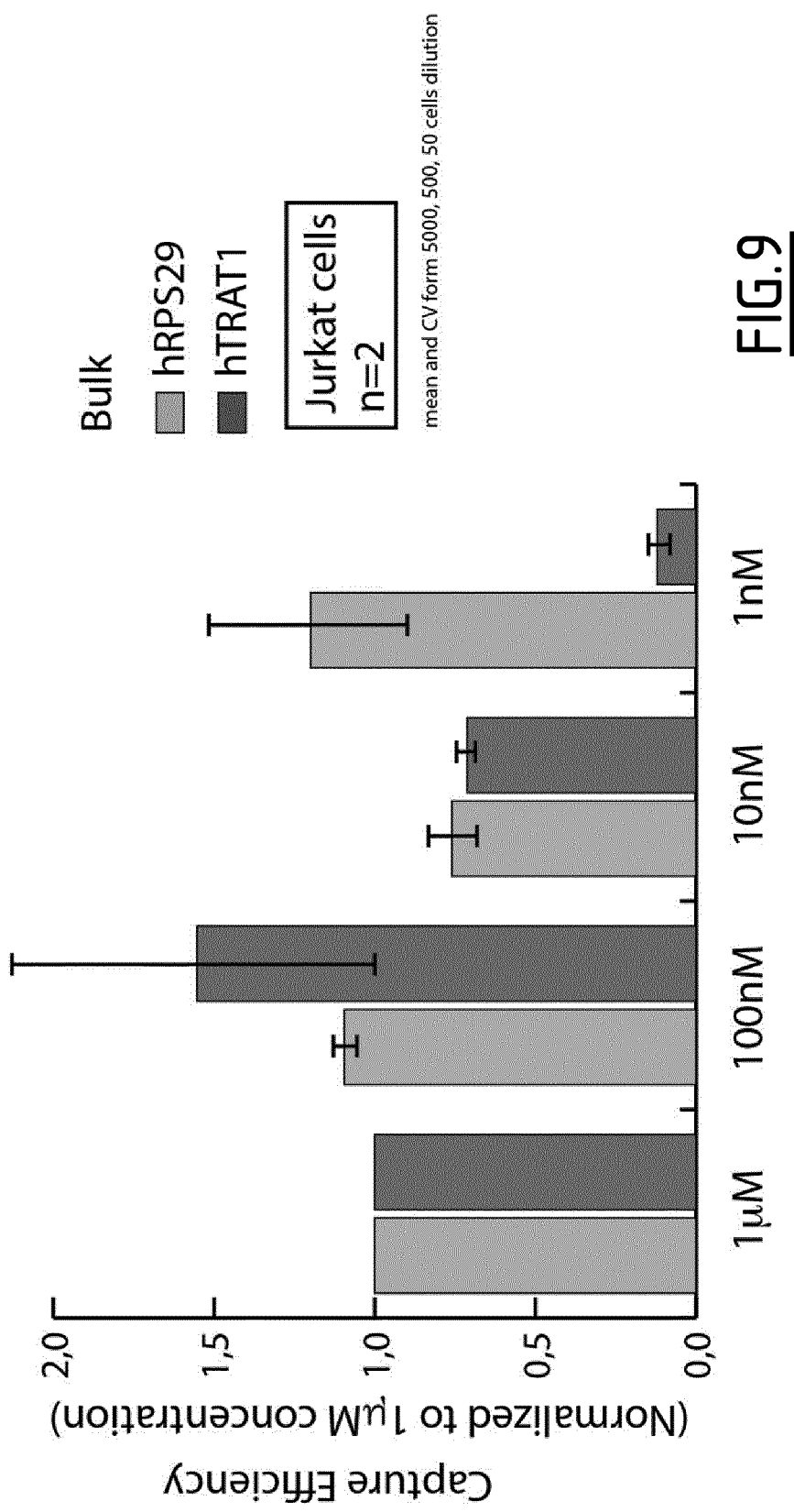

FIG. 9 is a graph depicting capture efficiency of human housekeeping gene RPS29 and TRAT1 reverse transcription for different primer concentrations (1 μM, 100 nM, 1 QnM, 1 nM).

Figure 10:
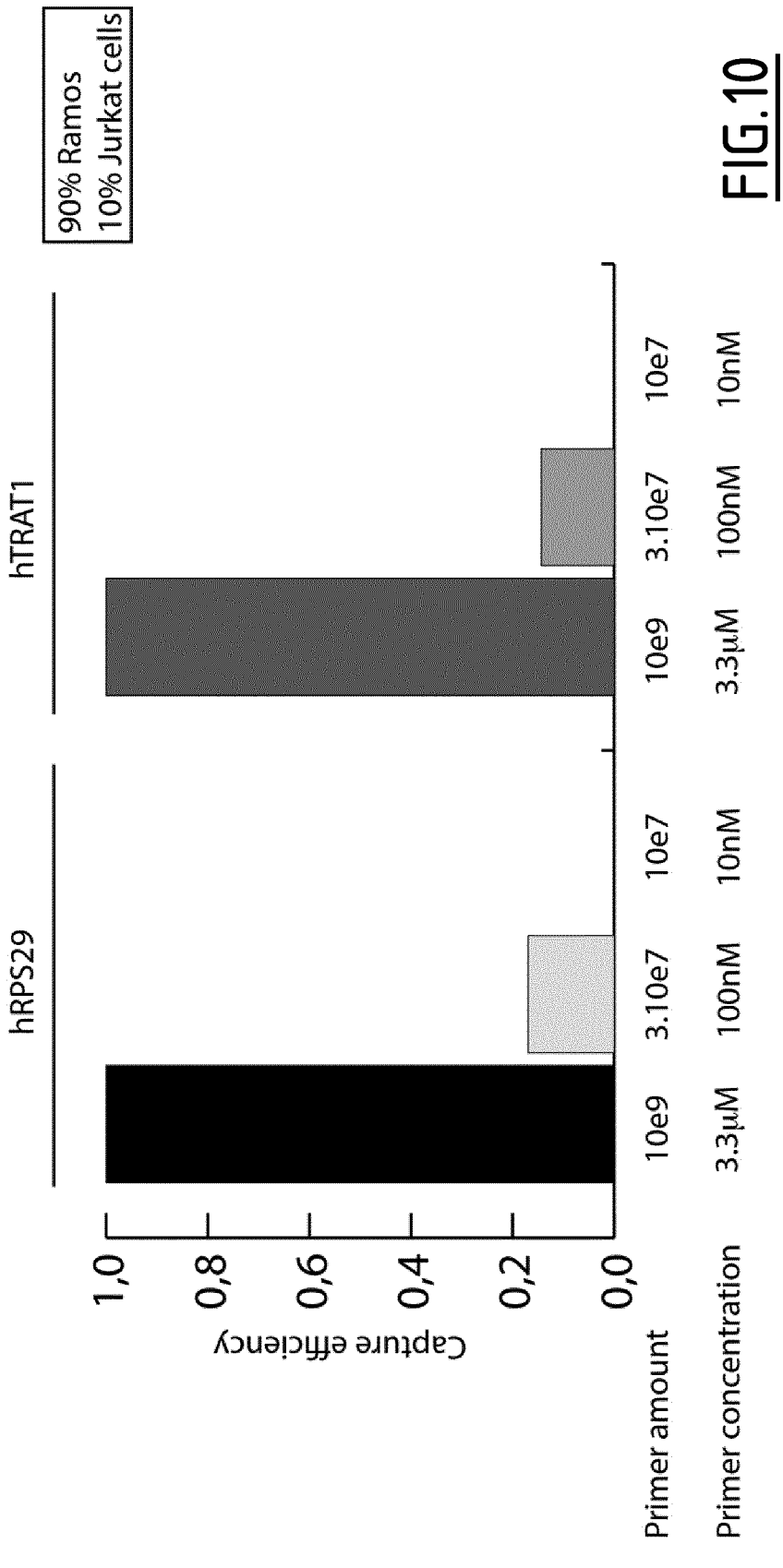

FIG. 10 is a graph depicting the capture efficiency of human housekeeping gene RPS29 and TRAT1 using polydT primer at different concentrations (either 3.3 μM or 100 or 33 nM.

SEQUENCE LISTING

SEQ ID NO: 1 shows the nucleotide sequence of the antisense primer Top_SBS12-ATP5G3 consisting of the nucleic acid sequence CAACGTGACTGGAGTTCAGACGTGTGCT

CTTCCGATCTCTGCTTCAGCGAAGGGTTTC

SEQ ID NO: 2 shows the nucleotide sequence of the antisense primer Top_SBS12-RPS29 consisting of -continued the nucleic acid sequence
CAACGTGACTGGAGTTCAGACGTGTGCTCTTCCGATCTAC

AGACACGACAAGAGCGA

SEQ ID NO: 3 shows the nucleotide sequence of the antisense primer Top_SBS12-ZNF780A consisting of the nucleic acid sequence CAACGTGACTGGAGTTCAGACGTGTGCTCTTCCGATCTTGAT

CCATGGACCATGTTGCT

SEQ ID NO: 4 shows the nucleotide sequence of the sense primer SBS3-ATP5G3 consisting of the nucleic acid sequence ACACTCTTTCCCTACACGACGCTCTTCCGATCTCAGGTGCTGCAACAGTA

GGA

SEQ ID NO: 5 shows the nucleotide sequence of the sense primer SBS3-RPS29 consisting of the nucleic acid sequence ACACTCTTTCCCTACACGACGCTCTTCCGATCTTTACCTCGTT

GCACTGCTGA

SEQ ID NO: 6 shows the nucleotide sequence of the sense primer SBS3-ZNF780A consisting of the nucleic acid sequence ACACTCTTTCCCTACACGACGCTCTTCCGATCTAGAGCGTTACTGCTGCA

CA

SEQ ID NO: 7 shows the nucleotide sequence of the antisense primer for mouse ATP5G3 consisting of the nucleic acid sequence CAACTGCAACTCTGGATCCAGCTC SEQ ID NO: 8 shows the nucleotide sequence of the sense primer for mouse ATP5G3 consisting of the nucleic acid sequence ACACTCTTTCCCTACACGACGCTCTTCCGAT

CTTCGCCTGTCACCTAGATCCA

SEQ ID NO: 9 shows the nucleotide sequence of the RT primer VH_1 for VH consisting of the nucleic acid sequence GGCCAGTGGATAGACAGATGGGGG SEQ ID NO: 10 shows the nucleotide sequence of the RT primer VH_2 for VH consisting of the nucleic acid sequence GGCCAGTGGATAGACCGATGGGGC SEQ ID NO: 11 shows the nucleotide sequence of the RT primer VH_3 for VH consisting of the nucleic acid sequence GGCCAGTGGATAGACTGATGGGGG SEQ ID NO: 12 shows the nucleotide sequence of the RT primer VH_4 for VH consisting of the nucleic acid sequence GTCACCGCAGCCAGGGACCAAGGG SEQ ID NO: 13 shows the nucleotide sequence of the RT primer VLk_1 for VH consisting of the nucleic acid sequence GCGTTTCATTTCCAGCTTGG SEQ ID NO: 14 shows the nucleotide sequence of the RT primer VLk_2 for VH consistin of the nucleic acid sequence GCGTTTGATTTCCAGCTTGG SEQ ID NO: 15 shows the nucleotide sequence of the RT primer VLk_3 for VH consisting of the nucleic acid sequence GCGTTTTATTTCCAATTTTG -continued SEQ ID NO: 16 shows the nucleotide sequence of
the T7 antisense PCR1 primer consisting of the
nucleic acid sequence
GAATTTAATACGACTCACTATAGGGAGA SEQ ID NO: 17 shows the nucleotide sequence of
the sense primer MmLH_AG1 consisting of the
nucleic acid sequence
TAACTGCAGGTGTCCACTCC SEQ ID NO: 18 shows the nucleotide sequence of
the sense primer MmLH_AG2 consisting of the
nucleic acid sequence
CAGCTACAGGTGTCCACTCC SEQ ID NO: 19 shows the nucleotide sequence of
the sense primer MmLH_AG3 consisting of the
nucleic acid sequence
TTTATCAAGGTGTGCATTGT SEQ ID NO: 20 shows the nucleotide sequence of
the sense primer MmLH_AG4 consisting of the
nucleic acid sequence
GAACTGCAGGCGTCCACTCT SEQ ID NO: 21 shows the nucleotide sequence of
the sense primer MmLH_AG5 consisting of the
nucleic acid sequence
TAACTGCAGGTGTTCACTCC SEQ ID NO: 22 shows the nucleotide sequence of
the sense primer MmLH_AG6 consisting of the
nucleic acid sequence
TCCCAAGCTGTGTCCTATCC SEQ ID NO: 23 shows the nucleotide sequence of
the sense primer MmLH_AG7 consisting of the
nucleic acid sequence
TTCCAAGCTGTGTCCTGTCC SEQ ID NO: 24 shows the nucleotide sequence of
the sense primer MmLH_AG8 consisting of the
nucleic acid sequence
CTTTTAAAGGTATTCACTGT SEQ ID NO: 25 shows the nucleotide sequence of
the sense primer MmLH_AG9 consisting of the
nucleic acid sequence
TTTTAAAAGGGGTCCAGTGT SEQ ID NO: 26 shows the nucleotide sequence of
the sense primer MmLH_AG10 consisting of the
nucleic acid sequence
TTTTAAAAGGTGTCCAGTGT SEQ ID NO: 27 shows the nucleotide sequence of
the sense primer MmLH_AG11 consisting of the
nucleic acid sequence
TTTTAAATGGTATCCAGTGT SEQ ID NO: 28 shows the nucleotide sequence of
the sense primer MmLH_AG12 consisting of the
nucleic acid sequence
CTGCCCAAAGTGCCCAAGCA SEQ ID NO: 29 shows the nucleotide sequence of
the sense primer MmLH_AG13 consisting of the
nucleic acid sequence
CTGCCCAAAGTATCCAAGCA SEQ ID NO: 30 shows the nucleotide sequence of
the sense primer MmLHa consisting of the
nucleic acid sequence
ATGRASTTSKGGYTMARCTKGRTTT SEQ ID NO: 31 shows the nucleotide sequence of
the sense primer MmLHb consisting of the
nucleic acid sequence
ATGRAATGSASCTGGGTYWTYCTCTT -continued SEQ ID NO: 32 shows the nucleotide sequence of
the sense primer MmLHc1 consisting of the
nucleic acid sequence
ATGGACTCCAGGCTCAATTTAGTTTTCCT SEQ ID NO: 33 shows the nucleotide sequence of
the sense primer MmLHc2 consisting of the
nucleic acid sequence
ATGGCTGTCYTRGBGCTGYTCYTCTG SEQ ID NO: 34 shows the nucleotide sequence of
the sense primer MmLHc3 consisting of the
nucleic acid sequence
ATGGVTTGGSTGTGGAMCTTGCYATTCCT SEQ ID NO: 35 shows the nucleotide sequence of
the sense primer MmLHd1 consisting of the
nucleic acid sequence
ATGAAATGCAGCTGGRTYATSTTCTT SEQ ID NO: 36 shows the nucleotide sequence of
the sense primer MmLHd2 consisting of the
nucleic acid sequence
ATGGRCAGRCTTACWTYYTCATTCCT SEQ ID NO: 37 shows the nucleotide sequence of
the sense primer MmLHd3 consisting of the
nucleic acid sequence
ATGATGGTGTTAAGTCTTCTGTACCT SEQ ID NO: 38 shows the nucleotide sequence of
the sense primer MmLHe1 consisting of the
nucleic acid sequence
ATGGGATGGAGCTRTATCATSYTCTT SEQ ID NO: 39 shows the nucleotide sequence of
the sense primer MmLHe2 consisting of the
nucleic acid sequence
ATGAAGWTGTGGBTRAACTGGRT SEQ ID NO: 40 shows the nucleotide sequence of
the sense primer MmLHe3 consisting of the
nucleic acid sequence
ATGGRATGGASCKKIRTCTTTMTCT SEQ ID NO: 41 shows the nucleotide sequence of
the sense primer MmLHf1 consisting of the
nucleic acid sequence
ATGAACTTYGGGYTSAGMTTGRTTT SEQ ID NO: 42 shows the nucleotide sequence of
the sense primer MmLHf2 consisting of the
nucleic acid sequence
ATGTACTTGGGACTGAGCTGTGTAT SEQ ID NO: 43 shows the nucleotide sequence of
the sense primer MmLHf3 consisting of the
nucleic acid sequence
ATGAGAGTGCTGATTCTTTTGTG SEQ ID NO: 44 shows the nucleotide sequence of
the sense primer MmLHf4 consisting of the
nucleic acid sequence
ATGGATTTTGGGCTGATTTTTTTTATTG SEQ ID NO: 45 shows the nucleotide sequence of
the VL sense primer MmLKa consisting of the
nucleic acid sequence
ATGRAGWCACAKWCYCAGGTCTTT SEQ ID NO: 46 shows the nucleotide sequence of
the VL sense primer MmLKb consisting of the
nucleic acid sequence
ATGGAGACAGACACACTCCTGCTAT SEQ ID NO: 47 shows the nucleotide sequence of
the VL sense primer MmLKc consisting of the
nucleic acid sequence
ATGGAGWCAGACACACTSCTGYTATGGGT -continued SEQ ID NO: 48 shows the nucleotide sequence of
the VL sense primer MmLKd1 consisting of the
nucleic acid sequence
ATGAGGRCCCCTGCTCAGWTTYTTGGIWTCTT SEQ ID NO: 49 shows the nucleotide sequence of
the VL sense primer MmLKd2 consisting of the
nucleic acid sequence
ATGGGCWTCAAGATGRAGTCACAKWYYCWGG SEQ ID NO: 50 shows the nucleotide sequence of
the VL sense primer MmLKe1 consisting of the
nucleic acid sequence
ATGAGTGTGCYCACTCAGGTCCTGGSGTT SEQ ID NO: 51 shows the nucleotide sequence of
the VL sense primer MmLKe2 consisting of the
nucleic acid sequence
ATGTTGGGAYCGKTTTYAMMCTTTTCAATTG SEQ ID NO: 52 shows the nucleotide sequence of
the VL sense primer MmLKe3 consisting of the
nucleic acid sequence
ATGGAAGCCCCAGCTCAGCTTCTCTTCC SEQ ID NO: 53 shows the nucleotide sequence of
the VL sense primer MmLKf1 consisting of the
nucleic acid sequence
ATGAGIMMKTCIMTTCAITTCYTGGG SEQ ID NO: 54 shows the nucleotide sequence of
the VL sense primer MmLKf2 consisting of the
nucleic acid sequence
ATGAKGTHCYCIGCTCAGYTYCTIRG SEQ ID NO: 55 shows the nucleotide sequence of
the VL sense primer MmLKf3 consisting of the
nucleic acid sequence
ATGGTRTCCWCASCTCAGTTCCTTG SEQ ID NO: 56 shows the nucleotide sequence of
the VL sense prime MmLKf4 consisting of the
nucleic acid sequence
ATGTATATATGTTTGTTGTCTATTTCT SEQ ID NO: 57 shows the nucleotide sequence of
the VL sense primer MmLKg1 consisting of the
nucleic acid sequence
ATGAAGTTGCCTGTTAGGCTGTTGGTGCT SEQ ID NO: 58 shows the nucleotide sequence of
the VL sense primer MmLKg2 consisting of the
nucleic acid sequence
ATGGATTTWCARGTGCAGATTWTCAGCTT SEQ ID NO: 59 shows the nucleotide sequence of
the VL sense primer MmLKg3 consisting of the
nucleic acid sequence
ATGGTYCTYATVTCCTTGCTGTTCTGG SEQ ID NO: 60 shows the nucleotide sequence of
the VL sense primer MmLKg4 consisting of the
nucleic acid sequence
ATGGTYCTYATVTTRCTGCTGCTATGG SEQ ID NO: 61 shows the nucleotide sequence of
the VL sense primer LL_AG_1 consisting of the
nucleic acid sequence
attgctcaggttctttctcc SEQ ID NO: 62 shows the nucleotide sequence of
the VL sense primer LL_AG_2 consisting of the
nucleic acid sequence
cagtcataatgtccagagga SEQ ID NO: 63 shows the nucleotide sequence of
the VL sense primer LL_AG_3 consisting of the
nucleic acid sequence
cagtcataatgtccagggga -continued SEQ ID NO: 64 shows the nucleotide sequence of
the VL sense primer LL_AG_4 consisting of the
nucleic acid sequence
cagtcatactattcagagga SEQ ID NO: 65 shows the nucleotide sequence of
the VL sense primer LL_AG_5 consisting of the
nucleic acid sequence
cagtcatagtgtctaatgga SEQ ID NO: 66 shows the nucleotide sequence of
the VL sense primer LL_AG_6 consisting of the
nucleic acid sequence
cagtcatattgaccaatgga SEQ ID NO: 67 shows the nucleotide sequence of
the VL sense primer LL_AG_7 consisting of the
nucleic acid sequence
cagtcatattgtccagtgga SEQ ID NO: 68 shows the nucleotide sequence of
the VL sense primer LL_AG_8 consisting of the
nucleic acid sequence
cggtatctggtacctgtgga SEQ ID NO: 69 shows the nucleotide sequence of
the VL sense primer LL_AG_9 consisting of the
nucleic acid sequence
cgagtccagcctcaagcagt SEQ ID NO: 70 shows the nucleotide sequence of
the VL sense primer LL_AG_10 consisting of the
nucleic acid sequence
gaatcacaggcataatatgt SEQ ID NO: 71 shows the nucleotide sequence of
the VL sense primer LL_AG_11 consisting of the
nucleic acid sequence
gaatcccaggcatgatatgt SEQ ID NO: 72 shows the nucleotide sequence of
the VL sense primer LL_AG_12 consisting of the
nucleic acid sequence
gcatgtctggtgcctgtgca SEQ ID NO: 73 shows the nucleotide sequence of
the VL sense primer LL_AG_13 consisting of the
nucleic acid sequence
ggaccacggtctcagctgtc SEQ ID NO: 74 shows the nucleotide sequence of
the VL sense primer LL_AG_14 consisting of the
nucleic acid sequence
ggacttcagcctccagatgt SEQ ID NO: 75 shows the nucleotide sequence of
the VL sense primer LL_AG_15 consisting of the
nucleic acid sequence
ggatatcaggtgcccagtgt SEQ ID NO: 76 shows the nucleotide sequence of
the VL sense primer LL_AG_16 consisting of the
nucleic acid sequence
ggatccctggagccactggg SEQ ID NO: 77 shows the nucleotide sequence of
the VL sense primer LL_AG_17 consisting of the
nucleic acid sequence
ggatccctggatccactgca SEQ ID NO: 78 shows the nucleotide sequence of
the VL sense primer LL_AG_18 consisting of the
nucleic acid sequence
ggatctctggagtcagtggg SEQ ID NO: 79 shows the nucleotide sequence of
the VL sense primer LL_AG_19 consisting of the
nucleic acid sequence
ggattcaggaaaccaacggt -continued SEQ ID NO: 80 shows the nucleotide sequence of
the VL sense primer LL_AG_20 consisting of the
nucleic acid sequence
ggattccagcctccagaggt SEQ ID NO: 81 shows the nucleotide sequence of
the VL sense primer LL_AG_21 consisting of the
nucleic acid sequence
ggattcctgcttccagcagt SEQ ID NO: 82 shows the nucleotide sequence of
the VL sense primer LL_AG_22 consisting of the
nucleic acid sequence
ggattcgggaaaccaacggt SEQ ID NO: 83 shows the nucleotide sequence of
the VL sense primer LL_AG_23 consisting of the
nucleic acid sequence
ggatttcagcctccacaggt SEQ ID NO: 84 shows the nucleotide sequence of
the VL sense primer LL_AG_24 consisting of the
nucleic acid sequence
ggctccaaggcatgagctgt SEQ ID NO: 85 shows the nucleotide sequence of
the VL sense primer LL_AG_25 consisting of the
nucleic acid sequence
ggcttcatggtgctcagtgt SEQ ID NO: 86 shows the nucleotide sequence of
the VL sense primer LL_AG_26 consisting of the
nucleic acid sequence
ggcttacagacgcaggatgt SEQ ID NO: 87 shows the nucleotide sequence of
the VL sense primer LL_AG_27 consisting of the
nucleic acid sequence
ggcttacagatgccagatgt SEQ ID NO: 88 shows the nucleotide sequence of
the VL sense primer LL_AG_28 consisting of the
nucleic acid sequence
gggtatctggtacctgtggg SEQ ID NO: 89 shows the nucleotide sequence of
the VL sense primer LL_AG_29 consisting of the
nucleic acid sequence
gggtatctggtgcctgtgca SEQ ID NO: 90 shows the nucleotide sequence of
the VL sense primer LL_AG_30 consisting of the
nucleic acid sequence
gggttccaggttccactggt SEQ ID NO: 91 shows the nucleotide sequence of
the VL sense primer LL_AG_31 consisting of the
nucleic acid sequence
ggttatatggtgctgatggg SEQ ID NO: 92 shows the nucleotide sequence of
the VL sense primer LL_AG_32 consisting of the
nucleic acid sequence
ggttcccaggtgccagatgt SEQ ID NO: 93 shows the nucleotide sequence of
the VL sense primer LL_AG_33 consisting of the
nucleic acid sequence
ggttgtctggtgttgaagga SEQ ID NO: 94 shows the nucleotide sequence of
the VL sense primer LL_AG_34 consisting of the
nucleic acid sequence
ggtttccaggtatcagatgt SEQ ID NO: 95 shows the nucleotide sequence of
the VL sense primer LL_AG_35 consisting of the
nucleic acid sequence
ggtttccaggtgcaagatgt -continued SEQ ID NO: 96 shows the nucleotide sequence of
the VL sense primer LL_AG_36 consisting of the
nucleic acid sequence
ggtttgcaggtggtaaatgt SEQ ID NO: 97 shows the nucleotide sequence of
the VL sense primer LL_AG_37 consisting of the
nucleic acid sequence
ggtttttaggtgccagatgt SEQ ID NO: 98 shows the nucleotide sequence of
the VL sense primer LL_AG_38 consisting of the
nucleic acid sequence
gtgtcacagtgtcaaaggga SEQ ID NO: 99 shows the nucleotide sequence of
the VL sense primer LL_AG_39 consisting of the
nucleic acid sequence
gtgtctctgattctagggca ( SEQ ID NO: 100 shows the nucleotide sequence of
the VL sense primer LL_AG_40 consisting of the
nucleic acid sequence
gtgtgtctggtgctcatggg SEQ ID NO: 101 shows the nucleotide sequence of
the VL sense primer LL_AG_41 consisting of the
nucleic acid sequence
gttttcaaggtaccagatat SEQ ID NO: 102 shows the nucleotide sequence of
the VL sense primer LL_AG_42 consisting of the
nucleic acid sequence
gttttcaaggtaccagatgt SEQ ID NO: 103 shows the nucleotide sequence of
the Illumina Index Antisense primer consisting
of the nucleic acid sequence
CAAGCAGAAGACGGCATACGAGATINDEXGTGACTGGAGTTCAGACGTGT GCTCTTCCGATCT,
wherein Index stands for standard Illumina
indexes, which are 6 to 7 bases long.

SEQ ID NO: 104 shows the nucleotide sequence of
the VH sense primer VHs1 consisting of the
nucleic acid sequence
AATGATACGGCGACCACCGAGATCTACACTCTTTCCCTACACGACGCTCT

TCCGATCTGATGTGAAGCTTCAGGAGTC

SEQ ID NO: 105 shows the nucleotide sequence of
the VH sense primer VHs2 consisting of the
nucleic acid sequence
AATGATACGGCGACCACCGAGATCTACACTCTTTCCCTACACGACGCTCT

TCCGATCTCAGGTGCAGCTGAAGGAGTC

SEQ ID NO: 106 shows the nucleotide sequence of
the VH sense primer VHs3 consisting of the
nucleic acid sequence
AATGATACGGCGACCACCGAGATCTACACTCTTTCCCTACACGACGCTCT

TCCGATCTCAGGTGCAGCTGAAGCAGTC

SEQ ID NO: 107 shows the nucleotide sequence of
the VH sense primer VHs4 consisting of the
nucleic acid sequence
AATGATACGGCGACCACCGAGATCTACACTCTTTCCCTACACGACGCTCT

TCCGATCTCAGGTTACTCTGAAAGAGTC

SEQ ID NO: 108 shows the nucleotide sequence of
the VH sense primer VHs5 consisting of the
nucleic acid sequence
AATGATACGGCGACCACCGAGATCTACACTCTTTCCCTACACGACGCTCT

TCCGATCTGAGGTCCAGCTGCAACAATCT

SEQ ID NO: 109 shows the nucleotide sequence of
the VH sense primer VHs6 consisting of the -continued nucleic acid sequence
AATGATACGGCGACCACCGAGATCTACACTCTTTCCCTACACGACGCTCT

TCCGATCTGAGGTCCAGCTGCAGCAGTC

SEQ ID NO: 110 shows the nucleotide sequence of
the VH sense primer VHs7 consisting of the
nucleic acid sequence
AATGATACGGCGACCACCGAGATCTACACTCTTTCCCTACACGACGCTCT

TCCGATCTCAGGTCCAACTGCAGCAGCCT

SEQ ID NO: 111 shows the nucleotide sequence of
the VH sense primer VHs8 consisting of the
nucleic acid sequence
AATGATACGGCGACCACCGAGATCTACACTCTTTCCCTACACGACGCTCT

TCCGATCTGAGGTGAAGCTGGTGGAGTC

SEQ ID NO: 112 shows the nucleotide sequence of
the VH sense primer VHs9 consisting of the
nucleic acid sequence
AATGATACGGCGACCACCGAGATCTACACTCTTTCCCTACACGACGCTCT

TCCGATCTGAGGTGAAGCTGGTGGAATC

SEQ ID NO: 113 shows the nucleotide sequence of
the VH sense primer VHs10 consisting of the
nucleic acid sequence
AATGATACGGCGACCACCGAGATCTACACTCTTTCCCTACACGACGCTCT

TCCGATCTGATGTGAACTTGGAAGTGTC

SEQ ID NO: 114 shows the nucleotide sequence of
the VH sense primer VHs11 consisting of the
nucleic acid sequence
AATGATACGGCGACCACCGAGATCTACACTCTTTCCCTACACGACGCTCT

TCCGATCTGAGGTCCAGCTGCAACAGTC

SEQ ID NO: 115 shows the nucleotide sequence of
the VH sense primer VHs12 consisting of the
nucleic acid sequence
AATGATACGGCGACCACCGAGATCTACACTCTTTCCCTACACGACGCTCT

TCCGATCTGAGGTGCAGCTGGAGGAGTC

SEQ ID NO: 116 shows the nucleotide sequence of
the VL sense primer VKs1 consisting of the
nucleic acid sequence
AATGATACGGCGACCACCGAGATCTACACTCTTTCCCTACACGACGCTCT

TCCGATCTGATATTGTGATGACGCAGGCT

SEQ ID NO: 117 shows the nucleotide sequence of
the VL sense primer VKs2 consisting of the
nucleic acid sequence
AATGATACGGCGACCACCGAGATCTACACTCTTTCCCTACACGACGCTCT

TCCGATCTGATATTGTGATAACCCAG

SEQ ID NO: 118 shows the nucleotide sequence of
the VL sense primer VKs3 consisting of the
nucleic acid sequence
AATGATACGGCGACCACCGAGATCTACACTCTTTCCCTACACGACGCTCT

TCCGATCTGACATTGTGCTGACCCAATCT

SEQ ID NO: 119 shows the nucleotide sequence of
the VL sense primer VKs4 consisting of the
nucleic acid sequence
AATGATACGGCGACCACCGAGATCTACACTCTTTCCCTACACGACGCTCT

TCCGATCTGACATTGTGATGACCCAGTCT

SEQ ID NO: 120 shows the nucleotide sequence of
the VL sense primer VKs5 consisting of the
nucleic acid sequence
AATGATACGGCGACCACCGAGATCTACACTCTTTCCCTACACGACGCTCT -continued

TCCGATCTGATATTGTGCTAACTCAGTCT

SEQ ID NO: 121 shows the nucleotide sequence of
the VL sense primer VKs6 consisting of the
nucleic acid sequence
AATGATACGGCGACCACCGAGATCTACACTCTTTCCCTACACGACGCTCT

TCCGATCTGATATCCAGATGACACAG ACT

SEQ ID NO: 122 shows the nucleotide sequence of
the VL sense primer VKs7 consisting of the
nucleic acid sequence
AATGATACGGCGACCACCGAGATCTACACTCTTTCCCTACACGACGCTCT

TCCGATCTGACATCCAGCTGACTCAGTCT

SEQ ID NO: 123 shows the nucleotide sequence of
the VL sense primer VKs8 consisting of the
nucleic acid sequence
AATGATACGGCGACCACCGAGATCTACACTCTTTCCCTACACGACGCTCT

TCCGATCTCAAATTGTTCTCACCCAGTCT

SEQ ID NO: 124 shows the nucleotide sequence of
the VL sense primer VKs9 consisting of the
nucleic acid sequence
AATGATACGGCGACCACCGAGATCTACACTCTTTCCCTACACGACGCTCT

TCCGATCTGATGTTTTGATGACCCAAACT

SEQ ID NO: 125 shows the nucleotide sequence of
the primer RT_VLk consisting of the nucleic
acid sequence
GATGGTGGGAAGATGGATAC SEQ ID NO: 126 shows the nucleotide sequence of
the sense primer used in PCR3 consisting of the
nucleic acid sequence
AATGATACGGCGACCACCGAGATCTACACTCTTTCCCTACACGACGCTCT

TCCGATCT

SEQ ID NO: 127 shows the nucleotide sequence of
the antisense primer used in PCR3 consisting of
the nucleic acid sequence
CAAGCAGAAGACGGCATACGAGAT SEQ ID NO: 128 shows the nucleotide sequence
CARDWSRSWYLAPNGPDLDYW
of CDR3

SEQ ID NO: 129 shows the nucleotide sequence
CCSYAGGSTLVF
of CDR3

SEQ ID NO: 130 shows the nucleotide sequence
CARGGKSDDGNFRYFDHW
of CDR3

SEQ ID NO: 131 shows the nucleotide sequence
CQQRSSWPPGWTF
of CDR3

SEQ ID NO: 132 shows the nucleotide sequence
CAKSFGFGGVIVIGGYFLHW
of CDR3

SEQ ID NO: 133 shows the nucleotide sequence
CQQYDNLPLTF
of CDR3

SEQ ID NO: 134 shows the nucleotide sequence
CARHKTTSGWYSPLDYW
of CDR3

SEQ ID NO: 135 shows the nucleotide sequence
CQQYSGSVWTF
of CDR3

-continued

```
SEQ ID NO: 136 shows the nucleotide sequence
CARGVKAAGRTPNWFGPW
of CDR3

SEQ ID NO: 137 shows the nucleotide sequence
CQSYDSSLSGHVVF
of CDR3

SEQ ID NO: 138 shows the nucleotide sequence
CAREVSADILTGYYDYW
of CDR3

SEQ ID NO: 139 shows the nucleotide sequence
CQHYDNLPPTF
of CDR3
```

EXAMPLES

In order that the disclosure may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

Example 1

Bulk vs. Drop and RT Efficiency Measurement

Optimization of RT reaction starting from cell has been performed in bulk reaction. This experiment mimics a drop condition (especially the volume of reaction buffer per cell, the amount of reagent per cell). To confirm the bulk conditions mimic the drop conditions, a side-by-side RT reaction was performed in bulk and in drop. To assess the efficiency of the RT reaction, the results were compared with purified RNA extracted from the same cell population.

Comparisons are based on qPCR data. The Cp value (crossing point value determined by the $2^{nd}$ derivative max calculation method) of the droplet experiment was compared to the bulk experiment as well as to purified RNA samples cDNA synthesis.

Droplet based experiments were performed by co-flowing the lysis buffer containing mix (50 µL Lysis buffer 4×; 17.6 µL RT buffer 5×; 22.4 µL H2O; 2 µL polydT oligo 100 µM; 4 µL Protease Inhibitor; 4 µL DY-647 100 µM) with the RT mix buffer (22.5 µL First strand Reaction buffer 5×; 10 µL 0.1 M DTT; 10 µL 10 mM each dNTP; 2.5 µL RNAse inhibitor; 2.5 µL Superscript III RT enzyme; 2.5 µL DY-647 100 µM solution) with 200,000 human Ramos cells pre-washed in PBS, pelleted and resuspended in 1 µL of DY-647 100 µM solution+49 µL of cell suspension solution (300 µL Percoll; 33.3 µL NaCl 1.5 M; 10 µL Pluronic 10%; 25 µL Hepes 1 M; 50 µL Serum low IgG 5%; 581.7 µL Media DMEM). Lysis buffer 1× is 50 mM Tris HCl pH7.5, 75 mM NaCl, 3 mM MgCl₂, 0.2% Triton X-100. Using the feedback module with Fluigent pumps, ensure that the following flow rates are obtained (Table 2).

TABLE 2

| Flow rates (µL/hr) | Reagent |
|---|---|
| Variable, depends on drop volume | 5% (w/w) surfactant in HFE-7500 |
| 75 | RT Mix |

TABLE 2-continued

| Flow rates (µL/hr) | Reagent |
|---|---|
| 75 | Cells |
| 150 | Lysis |
| Flow rates (µL/hr) | Reagent |
| Variable, depends on drop volume | 5% (w/w) surfactant in HFE-7500 |

100 pL drops were generated (with a CV in width of <5%) and emulsion collected on ice in tube filled with HFE-7500. Once the production of the emulsion is finished, a syringe with HFE-7500 was used to attach to the longer tubing of the reservoir. The needle connected at the outlet was filled with oil and the syringe was plugged to prevent formation of any air bubbles. Disconnect immediately the tubing from the chip and slowly pull the plunger out to completely aspirate the emulsion still presents in the tubing. Avoid air bubbles inside the collection tube. The emulsion containing tube was placed into the Thermomixer at 55° C. for 60 min. RT was inactivated at 70° C. for 15 min and then 1 min at 4° C. Emulsion was collected and broken using perfluoro-octanol (v/v of emulsion), incubated until the oil and aqueous phases are separated. Centrifuge aqueous phase for 10 min at 10,000 g at 4° C. and recover the supernatant. Digest RNA and Protein by incubating with 2.5 µL of RNase A for 15 min at 37° C. and 4 µL of Proteinase K overnight at 37° C.

Bulk experiments were performed by mixing the 200,000 human Ramos cells (pre-washed in PBS as above) or RNA extracted (Machery Nagel extraction kit) from 200,000 human Ramos cells in reaction volume mimicking 100 pL per cell (20 µL final reaction). The mix is shown in Table 3.

TABLE 3

| | 100 pl per cell |
|---|---|
| H₂O RNase/DNase free | 5.9 µL |
| Cell Suspension Buffer (Containing Cells) | 5 µL |
| 10x Lysis Buffer | 2 µL |
| 5x RT Buffer | 4 µL |
| dNTP 10 mM | 1 µL |
| PolydT primer 100 µM stock | 0.2 µL |
| 0.1M DTT | 1 µL |
| SS III RT enzyme (200 U/µL) | 0.25 µL |
| RNase Inhibitor | 0.25 µL |
| Protease Inhibitor | 0.4 µL |
| Final volume | 20 µL |

The mixed cells and RNA were incubated for 10 min on ice and then RT was performed for 1 h at 55° C. RT was inactivated at 70° C. for 15 min. cDNA were processed as above.

All cDNAs were purified using RNAClean XP Beckman (at 0.8× ratio) and eluted in 20 µL H₂O. cDNAs were diluted 3 times and used as template for qPCR reaction (Roche LightCycler 480 master mix) for 3 sets of housekeeping genes known to be expressed at different level in Ramos cells. Cp values from pure RNA conditions and cells reactions were compared (FIG. 1A) and then used to estimate RT efficiency (RNA samples were considered as 100% efficient; FIG. 1B).

Figure 1A:
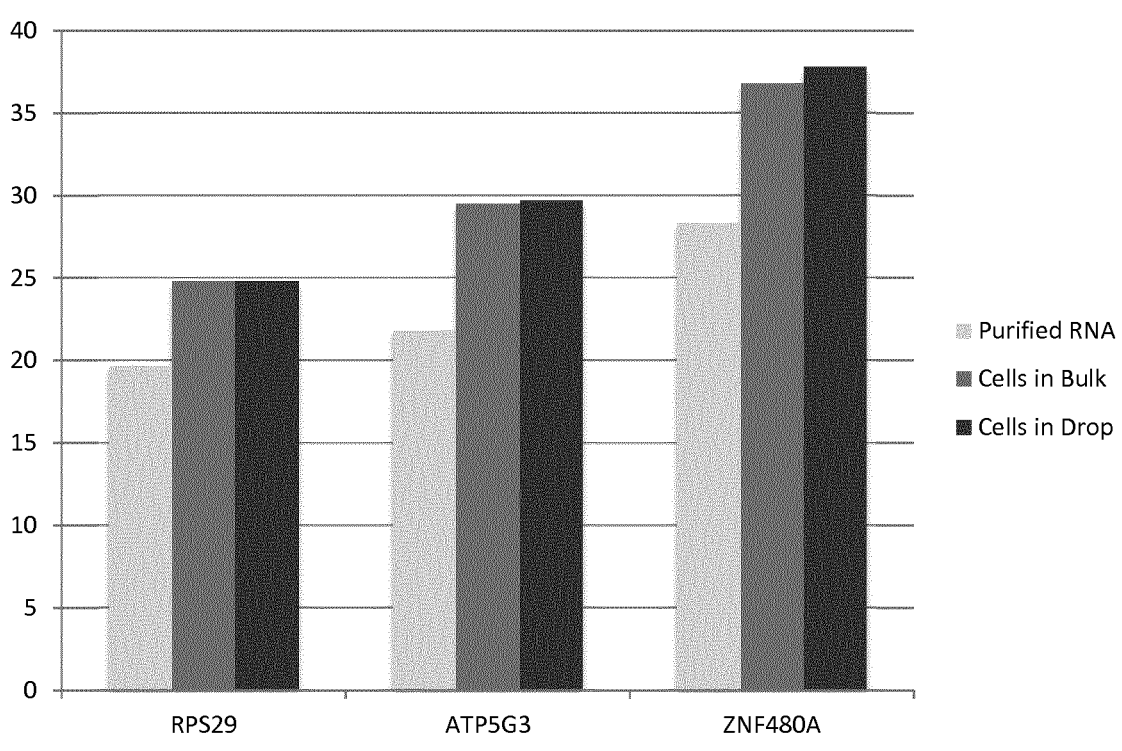
FIG. 1A is a graph demonstrating the Cp value (i.e. the crossing point value determined by the $2^{nd}$ derivative max calculation method) of three human genes (RPS29, ATP5G3 and ZNF480A) across three different conditions (purified RNA, cells lysed in bulk, and cells lysed in a drop) using a non-optimized protocol.
Figure 1B:
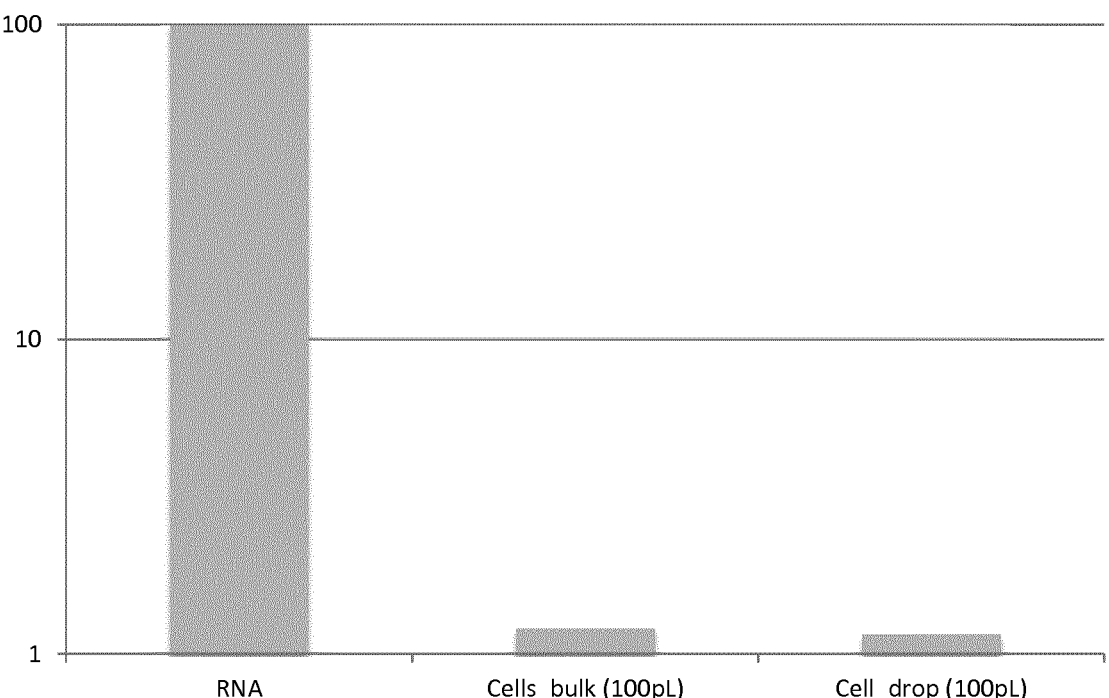
FIG. 1B is a graph depicting the percentage of the mean efficiency (of the genes shown in FIG. 1A) using a non-optimized protocol of reverse transcription across three different conditions (purified RNA, Cells lysed in bulk, and Cells lysed in a drop).

Altogether this experiment shows droplet and bulk based experiment mimicking the same volume/cell give comparable results for the 3 genes tested (FIG. 1A). Second, using standard conditions, mean of RT efficiency is approximately 2% for the 3 genes tested (FIG. 1B). This value is in agreement with previous reports.

Antisense Primer Sequence for Human Genes qPCR

```
Top_SBS12-ATP5G3:
                                       (SEQ ID NO: 1)
/5Phos/CAACGTGACTGGAGTTCAGACGTGTGCTCTTCCGATCTCTG

CTTCAGCGAAGGGTTTC

Top_SBS12-RPS29:
                                       (SEQ ID NO: 2)
/5Phos/CAACGTGACTGGAGTTCAGACGTGTGCTCTTCCGATCTACA

GACACGACAAGAGCGA

Top_SBS12-ZNF780A:
                                       (SEQ ID NO: 3)
/5Phos/CAACGTGACTGGAGTTCAGACGTGTGCTCTTCCGATCTTGA

TCCATGGACCATGTTGCT

Sense primer sequence for human genes qPCR
SBS3-ATP5G3:
                                       (SEQ ID NO: 4)
ACACTCTTTCCCTACACGACGCTCTTCCGATCTCAGGTGCTGCAACAG

TAGGA

SBS3-RPS29:
                                       (SEQ ID NO: 5)
ACACTCTTTCCCTACACGACGCTCTTCCGATCTTTACCTCGTTGCACT

GCTGA

SBS3-ZNF780A:
                                       (SEQ ID NO: 6)
ACACTCTTTCCCTACACGACGCTCTTCCGATCTAGAGCGTTACTGCTG

CACA
```

Example 2

Impact of Drop Size in RT Efficiency

Figure 2:
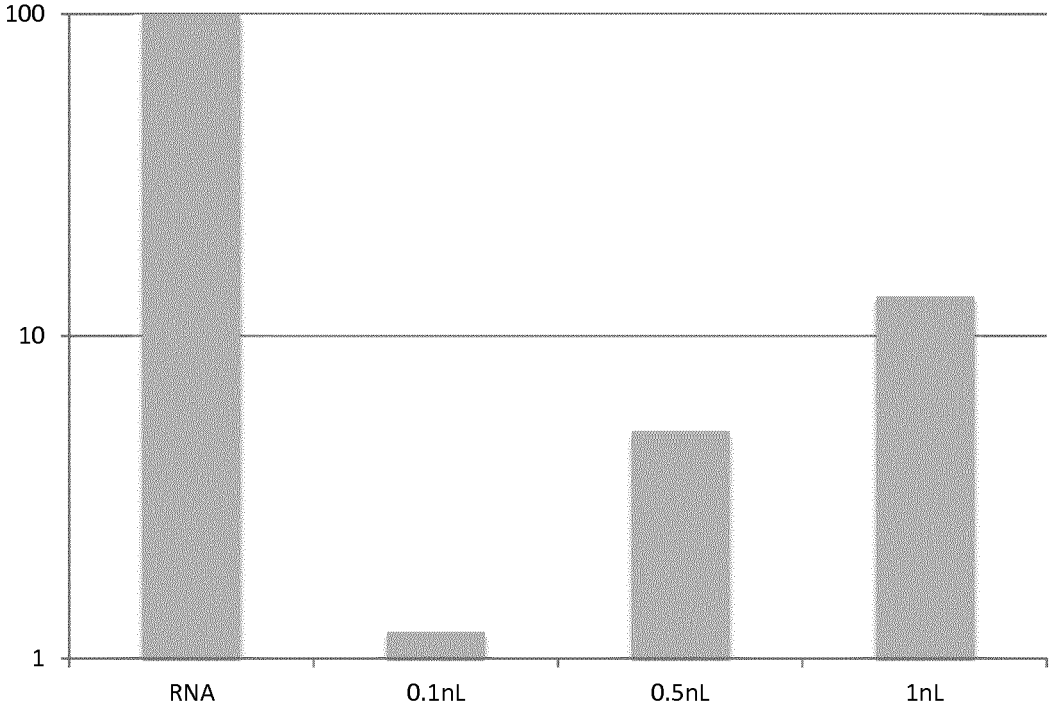
FIG. 2 is a graph depicting the percentage of the mean efficiency (of the genes shown in FIG. 1A) when compared to purified RNA in three conditions varying the total volume of the reaction used per cell using a non optimized protocol.

The impact of buffer volume per cell in RT efficiency was assessed by increasing the reagent/volume accordingly to Example 1. The Cp value was compared to purified RNA conditions (FIG. 2). A 1% RT efficiency in 100 pL volume was achieved, which is higher than reported and increased to >10% efficiency in 1 nL reaction/cell.

Example 3

Impact of Amount of RT Enzyme, Lysis Buffer in RT Efficiency

To further improve the RT efficiency in sub-nanoliter volumes, the impact of increased RT concentration, lysis buffers and reagents of the RT reaction were assessed. We compared the impact of these modifications on the RT efficiency, based on purified RNA conditions in a standard cDNA synthesis (as described by supplier).

FIG. 3A shows the impact of increasing the RT concentration in droplet-based experiments. Increasing the RT enzyme by a factor of 5 increased the cDNA synthesis by a mean of 10 times (based on 3 different genes Cp values). The biggest impact is achieved for low expressed genes, arguing for a genuine effect of RT synthesis efficiency. The micro-fluidic encapsulation of cells together with RT primers and RT mix was performed as described in Example 1. Droplet based experiment were performed by co-flowing the lysis buffer containing mix (50 µL Lysis buffer 4×; 17.6 µL RT buffer 5×; 22.4 µL $H_2O$; 2 µL polydT oligo 100 µM; 4 µL Protease Inhibitor; 4 µL DY-647 100 µM) with the RT mix buffer (22.5 µL First strand Reaction buffer 5×; 10 µL 0.1 M DTT; 10 µL 10 mM each dNTP; 2.5 µL RNAse inhibitor; 2.5 µL Superscript III RT enzyme; 2.5 µL DY-647 100 µM solution) with 200,000 human Ramos cells pre-washed in PBS, pelleted and resuspended in 1 µL of DY-647 100 µM solution+49 µL of cell suspension solution (300 µL Percoll; 33.3 µL NaCl 1.5 M; 10 µL Pluronic 10%; 25 µL Hepes 1 M; 50 µL Serum low IgG 5%; 581.7 µL Media DMEM). Lysis buffer 1× is 50 mM Tris HCl pH7.5, 75 mM NaCl, 3 mM $MgCl_2$, 0.2% Triton X-100.

In the emulsion where the concentration of RT enzyme is 5× higher than in the example above, we co-flowed the lysis buffer containing mix (50 µL Lysis buffer 4×; 27.6 µL RT buffer 5×; 12.4 µL H2O; 2 µL polydT oligo 100 µM; 4 µL Protease Inhibitor; 4 µL DY-647 100 µMM) with the RT mix buffer (12.5 µL First strand Reaction buffer 5×; 10 µL 0.1 M DTT; 10 µL 10 mM each dNTP; 2.5 µL RNAse inhibitor; 12.5 µL Superscript III RT enzyme; 2.5 µL DY-647 100 µM solution) and proceeded to cell encapsulation as above and as Example 1. cDNA purification and qPCR was done as Example 1. FIG. 3B shows the impact of lysis buffer for efficient cDNA synthesis. $MgCl_2$ complemented (which is required for efficient RT enzyme activity) hypotonic lysis buffer was compared with hypotonic water solution. $MgCl_2$ complemented hypotonic lysis buffer is required for efficient cDNA synthesis in sub nanoliter reaction volumes per cell. As described in Example 1, the impact of lysis condition was analyzed starting from cells in a bulk reaction and in a volume mimicking 100 pL per cell. Bulk experiments were performed by mixing the 200,000 human Ramos cells (pre-washed in PBS as Example 1) in a reaction volume mimicking 100 pL per cell (20 µL final reaction). The mix is described below in Table 4.

TABLE 4

| | Reagent final concentration | Lysis in $MgCl_2$ supplemented hypotonic buffer | Lysis in hypotonic $H_2O$ solution |
|---|---|---|---|
| $H_2O$ RNase/DNase free | | 1.7 µL | 3.7 µL |
| Cell Suspension Buffer (Containing 200,000 Cells) | | 5 µL | 5 µL |
| 10x Lysis Buffer (100 mM TrisHCl pH 7.5, 33.3 mM $MgCl_2$, 2% TritonX100) | 1x | 2 µL | — |
| 5x RT Buffer | 1x | 4 µL | 4 µL |
| dNTP 10 mM | 0.5 mM | 1 µL | 1 µL |
| 0.1M DTT | 5 mM | 1 µL | 1 µL |
| SS III RT enzyme (200 U/µL) | 12.5 U/µL | 1.25 µL | 1.25 µL |
| RNase Inhibitor | 1.25 U/µL | 1.25 µL | 1.25 µL |

TABLE 4-continued

| | Reagent final concentration | Lysis in MgCl$_2$ supplemented hypotonic buffer | Lysis in hypotonic H$_2$O solution |
|---|---|---|---|
| Protease Inhibitor | 2x | 0.8 μL | 0.8 μL |
| 10 μM polydT oligo | 1 μM | 2 μL | 2 μL |
| Final volume | | 20 μL | 20 μL |

Cells in the reverse transcriptase (RT) reaction mix were first incubated for 10 min on ice in order to lyse the cells. The RT was then triggered by incubating the reaction for 1 h at 55° C. (shaking at 750 rpm). RT enzyme were inactivated at 70° C. for 15 min. Cell debris was pelleted by centrifuging the RT reaction for 10 min at 10,000 g 4° C. cDNA in suspension were recovered in the supernatant, treated sequentially with 2.5 μL RNase A for 15 min at 37° C. (shaking at 750 rpm) and with 4 μL Proteinase K for ON at 37° C. (shaking at 750 rpm). cDNA was purified using RNA clean beads (Beckman) at 0.8× beads/solution ratio and eluted in 20 μL of DNase and RNase free water. Purified cDNA was used for assessing cDNA synthesis efficiency by qPCR.

FIG. 3C recapitulates the impact of the changes in RT amount/lysis conditions in the efficiency of cDNA synthesis. The overall RT efficiency was improved by approximately 40 times (from 1.2% to above 49%; purified RNA was set at 100%).

FIG. 3D shows the further impact of both increase drop volume and changes in the RT conditions (increase amount of RT enzyme and of RNase inhibitor and changes in the lysis buffer) in the RT efficiency. A side-by-side droplet based single cell RNAseq experiment was performed encapsulating mouse hybridoma cells either in 100 pL or 500 pL drops, as described in Examples 5. RT efficiency analysis of captured ATP5G3 housekeeping gene barcoded cDNA showed a 2-fold increase in the amount of cDNA generated by the 500 pL droplet based RNAseq compared to the 100 pL. This result has been consistently repeated with human cells for other genes and in the mouse hybridoma system.

Antisense primer sequence for mouse ATP5G3 gene qPCR/5Phos/CAAC TGCAACTCTGGATCCAGCTC (SEQ ID NO: 7)

Sense primer sequence for mouse ATP5G3 gene qPCR ACACTCTTTCCCTACACGACGCTCTTCC-GATCTTCGCCTGTCACCTAGATCCA (SEQ ID NO: 8)

To reach 100% RT efficiency compared to purified RNA conditions, the RT reaction conditions were further optimized (Percoll removal during cell encapsulation, selected broad spectrum RNAse inhibitor, optimization of cDNA recovery and purification). Mouse hybridoma cells expressing immunoglobulins were encapsulated in 500 pL drops and performed droplet based single cell VH/VL mRNA capture and cDNA synthesis in the drop. In parallel, RNA were extracted and purified from the same cells population and reverse transcription of VH and VL mRNA was performed in tube based assay, as described by supplier recommendation. The VH/VL cDNA synthesis efficiency was assessed by real time quantitative PCR. FIG. 3E shows the % of RT efficiency of droplet based approaches compared to purified RNA, which is above 100% for the light chain immunoglobulin variable genes and approximately 30% for the heavy chain immunoglobulin variable genes. The lower value for VH may be due to lower PCR efficiency on barcoded sample.

Cells were washed in Cell Wash Buffer (CWB; DMEM F12 media, 0.1% Pluronic, 25 mM Hepes, 5% low IgG serum) and co-flowed in the microfluidic design in 47.4 μL CWB buffer containing 2.6 μL 100 μM DY-647 solution. The hydrogel beads library carrying the single cell barcodes and the primers for VH and VL mRNA capture and cDNA synthesis in the drop where washed 10 times in 1× BW buffer, spin at 2500 g for 2 min at 4° C. The double stranded barcodes were denatured in 1 mL denaturation solution (700 μL H$_2$O+300 μL 1 M NaOH) at 22° C. for 2 min. The beads were washed 3 times in BW buffer, and labeled with 10 μL of FITC biotin 100 μM and incubated at room temperature on a rotating platform for 10 min. Following 3 washes in BW buffer, the beads were heated for 2 min at 70° C. and the supernatant removed. Finally the beads were washed in 200 μL of the lysis/Pi/DTT/Dye containing buffer (80 μL Lysis buffer 10×; 8 μL Protease inhibitor, 8 μL Dye 647 100 μM and 4 μL 1 M DTT). The beads were spun at 2500 g for 2 min at 4° C. and the supernatant was removed leaving 50 μL of buffer/HgB mix.

Droplet based experiments were performed by co-flowing the hydrogel beads carrying single cell barcode and primers in lysis buffer with the RT mix buffer (52 μL First strand Reaction buffer 5×; 10 μL 0.1 M DTT; 13 μL 10 mM each dNTP; 16.25 μL SUPERin RNAse inhibitor; 16.25 μL Superscript III RT enzyme; 2.5 μL DY-647 100 μM solution) with 15,000 mouse hybridoma cells.

The encapsulation of cells together with RT primers and RT mix was performed as shown in Table 5.

TABLE 5

| Flow rates (μL/hr) | Reagent |
|---|---|
| 200-250 | 5% (w/w) surfactant in HFE-7500 |
| 74 (200 for a Syringe pump) | RT Mix |
| 50 (200 for a syringe pump) | Hydrogel beads in lysis buffer |
| 74 (100 for a syringe pump) | Cells |

Example 4

Hybridoma Mixture

To assess VH/VL gene pairing accuracy in sub-nanoliter droplet, mouse hybridoma cell lines expressing known antibody sequences were mixed in equal proportions. The cells were washed in PBS and resuspended in 47.5 μL of Cell Suspension Buffer (300 μL Percoll; 33.3 μL NaCl 1.5 M; 10 μL Pluronic 10%; 25 μL Hepes 1 M; 50 μL Serum low IgG 5%; 581.7 μL Media DMEM) plus 2.5 μL of 100 μM DY-647. Cells were co-encapsulated with hydrogel beads library carrying the single cell barcodes and the primers for VH and VL mRNA capture and cDNA synthesis in the drop.

```
RT primer sequence:
                                   (SEQ ID NO: 9)
VH_1 : GGCCAGTGGATAGACAGATGGGGG (SEQ ID NO: 10)
VH_2: GGCCAGTGGATAGACCGATGGGGC (SEQ ID NO: 11)
VH_3: GGCCAGTGGATAGACTGATGGGGG (SEQ ID NO: 12)
VH_4: GTCACCGCAGCCAGGGACCAAGGG (SEQ ID NO: 13)
VLk_1 : GCGTTTCATTTCCAGCTTGG (SEQ ID NO: 14)
VLk_2: GCGTTTGATTTCCAGCTTGG (SEQ ID NO: 15)
VLk_3: GCGTTTTATTTCCAATTTTG
```

The hydrogel beads where washed 10 times in 1× BW buffer and spun at 2500 g for 2 min at 4° C. The double stranded barcodes were denatured in 1 mL denaturation solution (700 μL $H_2O$+300 μL 1 M NaOH) at 22° C. for 2 min. The beads were washed 3 times in BW buffer, and labeled with 10 μL of FITC biotin 20 μM and incubate at room temperature on a rotating platform for 1 h. Following 3 washes in 4× lysis buffer (0.8% TritonX100, 12 mM $MgCl_2$, 200 mM Tris-HCl pH7.4), the beads were heated for 2 min at 70° C. and the supernatant removed. The beads were solubilized in 50 μL lysis buffer 4×, 27.6 μL of 5× first strand RT buffer, 4 μL Protease Inhibitor, 4 μL DY-647 100 μM, 4.4 μL $H_2O$ and 10 μL 0.1 M DTT.

The beads and the cells were co-flowed with RT mix described in Table 6.

TABLE 6

| Mix | Volume [μL] |
|---|---|
| 5x Superscript III RT buffer | 12.5 |
| dNTP 10 mM | 10 |
| RNase inhibitor (20 U/μL) | 12.5 |
| Superscript III RT (200 U/μL) | 12.5 |
| 100 μM DY-647 solution | 2.5 |

Using the feedback module with Fluigent pumps, ensures that the following flow rates shown in Table 7 were obtained.

TABLE 7

| Flow rates (μl/hr) | Reagent |
|---|---|
| 150 | 5% (w/w) surfactant in HFE-7500 |
| 75 | RT Mix |
| 75 | Cells |
| 150 | Hydrogel beads in lysis buffer |

Ensure producing drops of 100-110 pL. Once the emulsion was produced, oligo photocleavage proceeded for 30 s at 200 mW/cm². The emulsion was incubated at 55° C. for 60 min and the RT was inactivated at 70° C. for 15 min. The tube was allowed to cool down for 1 min at 4° C. The Emulsion was transferred by pushing the syringe plunger in a new 1.5 mL DNA LoBind tube and vortex 30 s the emulsion to allow oligo diffusion from beads. To efficiently break the emulsion and recover the cDNA, as much oil was removed as possible with a syringe without taking any drops. Perfluorooctanol (v/v of emulsion) was added and allowed to mix for 5-10 min at room temp with occasional soft vortex (5 seconds) and soft spin (5 seconds) to separate phases.

A second photocleavage proceeded for 60 s at 200 mW/cm². The emulsion was vortexed for 30 s and incubated for 5 min at room temperature to allow oligo diffusion from beads.

The oil phase was removed with a syringe. The emulsion was vortexed 30 s and incubated for 5 min at room temperature to allow oligo diffusion from beads. cDNA was treated with 2.5 μL of RNase A to the Eppendorf and placed in a DNase/RNase free DNA LoBind tube for 15 min at 37° C. The cDNA solution was treated with 4 μL of Proteinase K and placed in a 1.5 ml DNase/RNase free DNA LoBind tube for 1 h at 50° C. or overnight at 37° C.

The aqueous phase containing cDNA and hydrogel beads was applied to a 30 μM filter (Pierce Spin column) and washed with $H_2O$. 25% of the filtered cDNA was purified using RNA Clean UP beads with a 1× ratio and eluted into 40 μL of DNase and RNase free water. The VH/VL PCR reaction was performed as follows:

Use 4*10 μL of purified cDNA to perform PCR1 as described in Tables 8A and 8B.

TABLE 8A

| Mix | 1 tube | Final conc. | N tubes |
|---|---|---|---|
| $H_2O$ | 14.92 | — | 119.36 |
| 5X Go Taq Buffer | 10 | 1x | 80 |
| MgCl2 | 3 | 1.25 mM | 24 |
| dNTP 10 mM | 1 | 0.2 mM | 8 |
| Primer as - 5 μM | 2.5 | 0.25 μM | |
| Primer s - 1.5 μM | 8.33 | 0.25 μM | 66.64 |
| Go Taq Polymerase | 0.25 | | 2 |
| DNA template | 10 | — | |
| Total | 50 | — | 300 |

TABLE 8B

| VH and VL Thermo-cycling | | |
|---|---|---|
| Activate Taq Polymerase: | Time | Temps (° C.) |
| | 2 min | 95 |
| Denaturation: | 1 min | 95 |
| Annealing: | 1 min | 55 | 25 cycles |
| Extension: | 1 min | 72 |
| Finishing: | 10 min | 72 |
| | Keep | 4° C. |

The PCR was purified using AMPure XP beads at a ratio of 1× and eluted in 20 μL water. 10% of the PCR was run a 2% agarose gel. 50% of the purified PCR1 was run the PCR2 as follow shown in Tables 9A and 9B.

TABLE 9A

| Mix | 1 tube | Final conc. | N tubes |
|---|---|---|---|
| $H_2O$ | 17 | — | 136 |
| 5X Go Taq Buffer | 10 | 1x | 80 |
| MgCl2 | 3 | 1.25 mM | 24 |
| dNTP 10 mM | 1 | 0.2 mM | 8 |
| Primer as - 5 μM | 2.5 | 0.25 μM | |
| Primer s - 1.5 μM | 6.25 | 0.25 μM | 50 |
| Go Taq Polymerase | 0.25 | | 2 |
| DNA template | 10 | — | |
| Total | 50 | — | 300 |

TABLE 9B

| VH and VL Thermo-cycling | | | |
|---|---|---|---|
| Activate Taq Polymerase: | Time | Temps (° C.) | |
| | 2 min | 95 | |
| Denaturation: | 1 min | 95 | |
| Annealing: | 1 min | 55 | 10 cycles |
| Extension: | 1 min | 72 | |
| Finishing: | 10 min | 72 | |
| | Keep | 4° C. | |

The PCR was purified using AMPure XP beads at a ratio of 1× and eluted in 20 μL water. 10% of the PCR was run a 2% agarose gel. The gel was cut and the bands were weighed. Bands were purified using a Gel Extraction kit (QIAGEN™) and eluted in 10 μL water.

PCR Primer Set

First PCR Reaction

T7 antisense PCR1 primer sequence

GAATTTAATACGACTCACTATAGGGAGA (SEQ ID NO: 16)

TABLE 10

| VH sense PCR_1 (v2) primer sequence | |
|---|---|
| MmLH_AG1 | TAACTGCAGGTGTCCACTCC (SEQ ID NO: 17) |
| MmLH_AG2 | CAGCTACAGGTGTCCACTCC (SEQ ID NO: 18) |
| MmLH_AG3 | TTTATCAAGGTGTGCATTGT (SEQ ID NO: 19) |
| MmLH_AG4 | GAACTGCAGGCGTCCACTCT (SEQ ID NO: 20) |
| MmLH_AG5 | TAACTGCAGGTGTTCACTCC (SEQ ID NO: 21) |
| MmLH_AG6 | TCCCAAGCTGTGTCCTATCC (SEQ ID NO: 22) |
| MmLH_AG7 | TTCCAAGCTGTGTCCTGTCC (SEQ ID NO: 23) |
| MmLH_AG8 | CTTTTAAAGGTATTCACTGT (SEQ ID NO: 24) |
| MmLH_AG9 | TTTTAAAAGGGGTCCAGTGT (SEQ ID NO: 25) |
| MmLH_AG10 | TTTTAAAAGGTGTCCAGTGT (SEQ ID NO: 26) |
| MmLH_AG11 | TTTTAAATGGTATCCAGTGT (SEQ ID NO: 27) |
| MmLH_AG12 | CTGCCCAAAGTGCCCAAGCA (SEQ ID NO: 28) |
| MmLH_AG13 | CTGCCCAAAGTATCCAAGCA (SEQ ID NO: 29) |
| MmLHa | ATGRASTTSKGGYTMARCTKGRTTT (SEQ ID NO: 30) |
| MmLHb | ATGRAATGSASCTGGGTYWTYCTCTT (SEQ ID NO: 31) |
| MmLHc1 | ATGGACTCCAGGCTCAATTTAGTTTTCCT (SEQ ID NO: 32) |
| MmLHc2 | ATGGCTGTCYTRGBGCTGYTCYTCTG (SEQ ID NO: 33) |
| MmLHc3 | ATGGVTTGGSTGTGGAMCTTGCYATTCCT (SEQ ID NO: 34) |
| MmLHd1 | ATGAAATGCAGCTGGRTYATSTTCTT (SEQ ID NO: 35) |
| MmLHd2 | ATGGRCAGRCTTACWTYYTCATTCCT (SEQ ID NO: 36) |

TABLE 10-continued

| VH sense PCR_1 (v2) primer sequence | |
|---|---|
| MmLHd3 | ATGATGGTGTTAAGTCTTCTGTACCT (SEQ ID NO: 37) |
| MmLHe1 | ATGGGATGGAGCTRTATCATSYTCTT (SEQ ID NO: 38) |
| MmLHe2 | ATGAAGWTGTGGBTRAACTGGRT (SEQ ID NO: 39) |
| MmLHe3 | ATGGRATGGASCKKIRTCTTTMTCT (SEQ ID NO: 40) |
| MmLHf1 | ATGAACTTYGGGYTSAGMTTGRTTT (SEQ ID NO: 41) |
| MmLHf2 | ATGTACTTGGGACTGAGCTGTGTAT (SEQ ID NO: 42) |
| MmLHf3 | ATGAGAGTGCTGATTCTTTTGTG (SEQ ID NO: 43) |
| MmLHf4 | ATGGATTTTGGGCTGATTTTTTTTATTG (SEQ ID NO: 44) |

TABLE 11

| VL sense PCR_1 (v2) primer sequence | |
|---|---|
| MmLKa | ATGRAGWCACAKWCYCAGGTCTTT (SEQ ID NO: 45) |
| MmLKb | ATGGAGACAGACACACTCCTGCTAT (SEQ ID NO: 46) |
| MmLKc | ATGGAGWCAGACACACTSCTGYTATGGGT (SEQ ID NO: 47) |
| MmLKd1 | ATGAGGRCCCCTGCTCAGWTTYTTGGIWTCTT (SEQ ID NO: 48) |
| MmLKd2 | ATGGGCWTCAAGATGRAGTCACAKWYYCWGG (SEQ ID NO: 49) |
| MmLKe1 | ATGAGTGTGCYCACTCAGGTCCTGGSGTT (SEQ ID NO: 50) |
| MmLKe2 | ATGTTGGGAYCGKTTTYAMMCTTTTCAATTG (SEQ ID NO: 51) |
| MmLKe3 | ATGGAAGCCCCAGCTCAGCTTCTCTTCC (SEQ ID NO: 52) |
| MmLKf1 | ATGAGIMMKTCIMTTCAITTCYTGGG (SEQ ID NO: 53) |
| MmLKf2 | ATGAKGTHCYCIGCTCAGYTYCTIRG (SEQ ID NO: 54) |
| MmLKf3 | ATGGTRTCCWCASCTCAGTTCCTTG (SEQ ID NO: 55) |
| MmLKf4 | ATGTATATATGTTTGTTGTCTATTTCT (SEQ ID NO: 56) |
| MmLKg1 | ATGAAGTTGCCTGTTAGGCTGTTGGTGCT (SEQ ID NO: 57) |
| MmLKg2 | ATGGATTTWCARGTGCAGATTWTCAGCTT (SEQ ID NO: 58) |
| MmLKg3 | ATGGTYCTYATVTCCTTGCTGTTCTGG (SEQ ID NO: 59) |
| MmLKg4 | ATGGTYCTYATVTTRCTGCTGCTATGG (SEQ ID NO: 60) |

TABLE 11-continued

| VL sense PCR_1 (v2) primer sequence | | |
|---|---|---|
| LL_AG_1 | attgctcaggttctttctcc | (SEQ ID NO: 61) |
| LL_AG_2 | cagtcataatgtccagagga | (SEQ ID NO: 62) |
| LL_AG_3 | cagtcataatgtccagggga | (SEQ ID NO: 63) |
| LL_AG_4 | cagtcatactattcagagga | (SEQ ID NO: 64) |
| LL_AG_5 | cagtcatagtgtctaatgga | (SEQ ID NO: 65) |
| LL_AG_6 | cagtcatattgaccaatgga | (SEQ ID NO: 66) |
| LL_AG_7 | cagtcatattgtccagtgga | (SEQ ID NO: 67) |
| LL_AG_8 | cggtatctggtacctgtgga | (SEQ ID NO: 68) |
| LL_AG_9 | cgagtccagcctcaagcagt | (SEQ ID NO: 69) |
| LL_AG_10 | gaatcacaggcataatatgt | (SEQ ID NO: 70) |
| LL_AG_11 | gaatcccaggcatgatatgt | (SEQ ID NO: 71) |
| LL_AG_12 | gcatgtctggtgcctgtgca | (SEQ ID NO: 72) |
| LL_AG_13 | ggaccacggtctcagctgtc | (SEQ ID NO: 73) |
| LL_AG_14 | ggacttcagcctccagatgt | (SEQ ID NO: 74) |
| LL_AG_15 | ggatatcaggtgcccagtgt | (SEQ ID NO: 75) |
| LL_AG_16 | ggatccctggagccactggg | (SEQ ID NO: 76) |
| LL_AG_17 | ggatccctggatccactgca | (SEQ ID NO: 77) |
| LL_AG_18 | ggatctctggagtcagtggg | (SEQ ID NO: 78) |
| LL_AG_19 | ggattcaggaaaccaacggt | (SEQ ID NO: 79) |
| LL_AG_20 | ggattccagcctccagaggt | (SEQ ID NO: 80) |
| LL_AG_21 | ggattcctgcttccagcagt | (SEQ ID NO: 81) |
| LL_AG_22 | ggattcgggaaaccaacggt | (SEQ ID NO: 82) |
| LL_AG_23 | ggatttcagcctccacaggt | (SEQ ID NO: 83) |
| LL_AG_24 | ggctccaaggcatgagctgt | (SEQ ID NO: 84) |
| LL_AG_25 | ggcttcatggtgctcagtgt | (SEQ ID NO: 85) |
| LL_AG_26 | ggcttacagacgcaggatgt | (SEQ ID NO: 86) |
| LL_AG_27 | ggcttacagatgccagatgt | (SEQ ID NO: 87) |
| LL_AG_28 | gggtatctggtacctgtggg | (SEQ ID NO: 88) |
| LL_AG_29 | gggtatctggtgcctgtgca | (SEQ ID NO: 89) |
| LL_AG_30 | gggttccaggttccactggt | (SEQ ID NO: 90) |
| LL_AG_31 | ggttatatggtgctgatggg | (SEQ ID NO: 91) |
| LL_AG_32 | ggttcccaggtgccagatgt | (SEQ ID NO: 92) |
| LL_AG_33 | ggttgtctggtgttgaagga | (SEQ ID NO: 93) |
| LL_AG_34 | ggtttccaggtatcagatgt | (SEQ ID NO: 94) |
| LL_AG_35 | ggtttccaggtgcaagatgt | (SEQ ID NO: 95) |
| LL_AG_36 | ggtttgcaggtggtaaatgt | (SEQ ID NO: 96) |
| LL_AG_37 | ggttttttaggtgccagatgt | (SEQ ID NO: 97) |
| LL_AG_38 | gtgtcacagtgtcaaaggga | (SEQ ID NO: 98) |
| LL_AG_39 | gtgtctctgattctagggca | (SEQ ID NO: 99) |

TABLE 11-continued

| VL sense PCR_1 (v2) primer sequence | | |
|---|---|---|
| LL_AG_40 | gtgtgtctggtgctcatggg | (SEQ ID NO: 100) |
| LL_AG_41 | gttttcaaggtaccagatat | (SEQ ID NO: 101) |
| LL_AG_42 | gttttcaaggtaccagatgt | (SEQ ID NO: 102) |

Second Nested PCR Reaction
  Illumina Index Antisense primer (SEQ ID NO: 103)
CAAGCAGAAGACGGCATACGAGATINDEXGTGACTGGAGTTCAGACGTGT

GCTCTTCCGATCT

TABLE 12

| VH sense PCR_2 (v2) primer sequence | |
|---|---|
| VHs1 | AATGATACGGCGACCACCGAGATCTACACTCTTTCCCTACAC GACGCTCTTCCGATCTGATGTGAAGCTTCAGGAGTC (SEQ ID NO: 104) |
| VHs2 | AATGATACGGCGACCACCGAGATCTACACTCTTTCCCTACAC GACGCTCTTCCGATCTCAGGTGCAGCTGAAGGAGTC (SEQ ID NO: 105) |
| VHs3 | AATGATACGGCGACCACCGAGATCTACACTCTTTCCCTACAC GACGCTCTTCCGATCTCAGGTGCAGCTGAAGCAGTC (SEQ ID NO: 106) |
| VHs4 | AATGATACGGCGACCACCGAGATCTACACTCTTTCCCTACAC GACGCTCTTCCGATCTCAGGTTACTCTGAAAGAGTC (SEQ ID NO: 107) |
| VHs5 | AATGATACGGCGACCACCGAGATCTACACTCTTTCCCTACAC GACGCTCTTCCGATCTGAGGTCCAGCTGCAACAATCT (SEQ ID NO: 108) |
| VHs6 | AATGATACGGCGACCACCGAGATCTACACTCTTTCCCTACAC GACGCTCTTCCGATCTGAGGTCCAGCTGCAGCAGTC (SEQ ID NO: 109) |
| VHs7 | AATGATACGGCGACCACCGAGATCTACACTCTTTCCCTACAC GACGCTCTTCCGATCTCAGGTCCAACTGCAGCAGCCT (SEQ ID NO: 110) |
| VHs8 | AATGATACGGCGACCACCGAGATCTACACTCTTTCCCTACAC GACGCTCTTCCGATCTGAGGTGAAGCTGGTGGAGTC (SEQ ID NO: 111) |
| VHs9 | AATGATACGGCGACCACCGAGATCTACACTCTTTCCCTACAC GACGCTCTTCCGATCTGAGGTGAAGCTGGTGGAATC (SEQ ID NO: 112) |
| VHs10 | AATGATACGGCGACCACCGAGATCTACACTCTTTCCCTACAC GACGCTCTTCCGATCTGATGTGAACTTGGAAGTGTC (SEQ ID NO: 113) |
| VHs11 | AATGATACGGCGACCACCGAGATCTACACTCTTTCCCTACAC GACGCTCTTCCGATCTGAGGTCCAGCTGCAACAGTC (SEQ ID NO: 114) |
| VHs12 | AATGATACGGCGACCACCGAGATCTACACTCTTTCCCTACAC GAGGCTCTTCCGATCTGAGGTGCAGCTGGAGGAGTC (SEQ ID NO: 115) |

TABLE 13

| VL sens PCR_2 (v2) primer sequence |
| --- |
| VKs1 | AATGATACGGCGACCACCGAGATCTACACTCTTTCCCTACACG ACGCTCTTCCGATCTGATATTGTGATGACGCAGGCT (SEQ ID NO: 116) |
| VKs2 | AATGATACGGCGACCACCGAGATCTACACTCTTTCCCTACACG ACGCTCTTCCGATCTGATATTGTGATAACCCAG (SEQ ID NO: 117) |
| VKs3 | AATGATACGGCGACCACCGAGATCTACACTCTTTCCCTACACG ACGCTCTTCCGATCTGACATTGTGCTGACCCAATCT (SEQ ID NO: 118) |
| VKs4 | AATGATACGGCGACCACCGAGATCTACACTCTTTCCCTACACG ACGCTCTTCCGATCTGACATTGTGATGACCCAGTCT (SEQ ID NO: 119) |
| VKs5 | AATGATACGGCGACCACCGAGATCTACACTCTTTCCCTACACG ACGCTCTTCCGATCTGATATTGTGCTAACTCAGTCT (SEQ ID NO: 120) |
| VKs6 | AATGATACGGCGACCACCGAGATCTACACTCTTTCCCTACACG ACGCTCTTCCGATCTGATATCCAGATGACACAG ACT (SEQ ID NO: 121) |
| VKs7 | AATGATACGGCGACCACCGAGATCTACACTCTTTCCCTACACG ACGCTCTTCCGATCTGACATCCAGCTGACTCAGTCT (SEQ ID NO: 122) |
| VKs8 | AATGATACGGCGACCACCGAGATCTACACTCTTTCCCTACACG ACGCTCTTCCGATCTCAAATTGTTCTCACCCAGTCT (SEQ ID NO: 123) |
| VKs9 | AATGATACGGCGACCACCGAGATCTACACTCTTTCCCTACACG ACGCTCTTCCGATCTGATGTTTTGATGACCCAAACT (SEQ ID NO: 124) |

The amplified and quality controlled VH and VL sequencing library was multiplexed (50% each) and sequenced on a MiSeq using 2*300 PE reads.

FIG. 4A depicts a nested PCR amplification of barcoded single cell VHNL

FIG. 4B depicts paired sequence reads sharing the same barcode (coming from the same cells) that were plotted based on the number of VH and VL reads.

FIG. 4C depicts the correct hybridoma VHNL pairing rate as a function of read threshold for each chain.

FIG. 4D depicts the number of hybridoma pairs pairing rate as a function of read threshold (for both chains).

Example 5

Hybridoma Dilution

To assess VHNL gene capture efficiency in a sub-nanoliter droplet, 3 mouse hybridoma cell line expressing known antibody sequences were mixed at a ratio of 60%-30%-10%. A total of 10,000 cells (plus 240,000 human non Ig expressing cells) were washed in PBS and resuspended in 97.4 μL of Cell Suspension Buffer (300 μL Percoll; 33.3 μL NaCl 1.5 M; 10 μL Pluronic 10%; 25 μL Hepes 1 M; 50 μL Serum low IgG 5%; 581.7 μL Media DMEM) plus 2.6 μL of 100 μM DY-647.

Cells were co-encapsulated with hydrogel beads library carrying the single cell barcodes and the primers for VH and VL mRNA capture and cDNA synthesis in the drop.

```
RT primer sequence:
                                    (SEQ ID NO: 9)
VH_1: GGCCAGTGGATAGACAGATGGGGG (SEQ ID NO: 10)
VH_2: GGCCAGTGGATAGACCGATGGGGC (SEQ ID NO: 11)
VH_3: GGCCAGTGGATAGACTGATGGGGG (SEQ ID NO: 12)
VH_4: GTCACCGCAGCCAGGGACCAAGGG (SEQ ID NO: 125)
RT_VLk: GATGGTGGGAAGATGGATAC
```

The hydrogel beads were washed 10 times in 1× BW buffer, spin at 2500 g for 2 min at 4° C. The double stranded barcodes were denatured in 1 mL denaturation solution (700 μL H$_2$O+300 μl 1 M NaOH) at 22° C. for 2 min. The beads were washed 3 times in BW buffer, and labeled with 10 μL of FITC biotin 20 μM and incubate at room temperature on rotating platform for 10 min. Following 3 washes in BW buffer, the beads were heated for 2 min at 70° C. and supernatant were removed. The beads were washed with 200 μL lysis*buffer (80 μL 10× Lysis buffer {2% Triton, 30 mM MgCl$_2$, 500 mM Tris-HCl pH 7.4}, 8 μL Protease inhibitor, 8 μL DY-647, 4 μL DTT 1 M). The beads were maintained in 50 μL lysis*buffer.

The RT mix was prepared as shown in Table 14.

TABLE 14

| Mix | Volume [μL] |
| --- | --- |
| 5× Superscript III RT buffer | 52 |
| dNTP 10 mM | 13 |
| RNase inhibitor (20 U/μL) | 16.25 |
| SuperScript III RT (200 U/μL) | 16.25 |
| 100 μM DY-647 solution | 2.5 |

The Cells, Hydrogel beads and RT mix were co-encapsulated in 500 pL drops using the flow rates shown in Table 14 using the feedback module with Fluigent pumps.

TABLE 15

| Flow rates (μL/hr) | Reagent |
| --- | --- |
| 200-250 | 5% (w/w) surfactant in HFE-7500 |
| 74 (200 for a Syringe pump) | RT Mix |
| 74 (200 for a syringe pump) | Cells |
| 50 (100 for a syringe pump) | Hydrogel beads in lysis buffer |

RT reaction, emulsion breakage, aqueous phase containing hydrogel beads and cDNA were recovered/treated as described in Example 4.

Half of the recovered cDNA was purified two times in a row using RNAClean Beckman beads at 1× beads/aqueous phase volume. Eluted cDNA was used for VH/VL amplification by PCR (PCR primers listed in Example 4), as described in Tables 15A and 16B.

TABLE 16A

| Mix | 1 tube | Final conc. | N tubes |
| --- | --- | --- | --- |
| H$_2$O | 4.92 | — | 4.92 |
| 5X Go Taq Buffer | 10 | 1x | 10 |
| MgCl2 | 3 | 1.25 mM | 3 |
| dNTP 10 mM | 1 | 0.2 mM | 1 |
| Primer as - 5 μM | 2.5 | 0.25 μM | 2.5 |

TABLE 16A-continued

| Mix | 1 tube | Final conc. | N tubes |
|---|---|---|---|
| Primer s - 1.5 µM | 8.33 | 0.25 µM | 8.33 |
| Go Taq Polymerase | 0.25 | | 0.25 |
| DNA template | 20 | — | |
| Total | 50 | — | 30 |

TABLE 16B

| VH and VL Thermo-cycling | | | |
|---|---|---|---|
| Activate Taq Polymerase: | Time | Temp (° C.) | |
| | 2 min | 95 | |
| Denaturation: | 1 min | 95 | |
| Annealing: | 1 min | 55 | 25 cycles |
| Extension: | 1 min | 72 | |
| Finishing: | 10 min | 72 | |
| | Keep | 4° C. | |

The VH and VL PCR1 products were purified two times using AMPure Beckman beads, at a 0.8× and a 1× ratio, respectively. Half of the PCR1 product was used for the PCR2 reaction, as shown in Tables 17A and 17B.

TABLE 17A

| Mix | 1 tube | Final conc. | N tubes |
|---|---|---|---|
| $H_2O$ | 9 | — | 9 |
| 5X Go Taq Buffer | 10 | 1x | 10 |
| MgCl2 | 3 | 1.25 mM | 3 |
| dNTP 10 mM | 1 | 0.2 mM | 1 |
| Primer as - 5 µM | 2.5 | 0.25 µM | 2.5 |
| Primer s - 1.5 µM | 6.25 | 0.25 µM | 6.25 |
| Go Taq Polymerase | 0.25 | | 0.25 |
| DNA template | 18 | — | |
| Total | 50 | — | 32 |

TABLE 17B

| VH and VL Thermo-cycling | | | |
|---|---|---|---|
| Activate Taq Polymerase: | Time | Temp (° C.) | |
| | 2 min | 95 | |
| Denaturation: | 1 min | 95 | |
| Annealing: | 1 min | 55 | 15 cycles |
| Extension: | 1 min | 72 | |
| Finishing: | 10 min | 72 | |
| | Keep | 4° C. | |

Amplified products were size selected on agarose gel, gel purified, quality controlled and sequenced on MiSeq 2*300 PE reads.

FIG. 5A depicts a nested PCR amplification of barcoded single cell VH/VL, depending on droplet volume (100 pL or 500 pL) and cDNA purification method (1 elution versus 2 elutions, named 1.1 or 1.2 and compared to 2 purifications, called 2.1). FIG. 5B depicts paired sequence reads sharing the same barcode (coming from the same cells) that were plotted based on the number of VH and VL reads, in 500 pL drops and with improved cDNA purification (2 purifications).

FIG. 5C depicts the number of hybridoma pairs pairing rate as a function of read threshold (for both chains), in 500 pL drops and with improved cDNA purification (2 purifications).

FIG. 5D depicts the correct pairing rate of hybridoma pairs pairing rate as a function of read threshold (for both chains), droplet volume (100 pL or 500 pL) and cDNA purification method (1 elution versus 2 elutions, named 1.1 or 1.2 and compared to 2 purifications, called 2.1)

FIG. 5F depicts the recovered hybridoma pair distribution at a threshold of 10 reads per chain, depending on droplet volume (100 pL or 500 pL) and cDNA purification method (1 elution versus 2 elutions, named 1.1 or 1.2 and compared to 2 purifications, called 2.1). The 500 pL droplet volume with improved cDNA purification (2 purifications) leads to original 60-30-10% hybridoma ratio.

Example 6

Screening Mouse Primary B Cells

Primary mouse spleen B cells secreting Tetanus Toxoid-specific antibodies were sorted and washed 2 times with 500 µL Cell Wash Buffer (915 µL DMEM/F12 cell culture media; 50 µL Serum Low IgG; 25 µL Hepes 1 M; 10 µL Pluronic F68 10%). Finally, were resuspended in 97.4 µL CWB and 2.6 µL DY-647.

Single cells carrying hydrogel beads were prepared as in Example 5.

Co-encapsulation of cells, hydrogel beads and RT mix in 500 pL drops was performed as described in Example 5. Emulsion was broken as described in Example 5.

Aqueous phase containing hydrogel beads and cDNA were split into 2 equal volumes. Half of the aqueous phase was treated with 1 µL of RNAse A (for 15 min at 37° C.) and 4 µL of Proteinase K (over-night at 37° C.) and then half of the material was purified. Half of the aqueous phase was centrifuged at 10,000 g for 10 min at 4° C. Recovered supernatant was treated as above and then half of the material was purified.

cDNA were purified twice with RNAClean Beads using 1× bead:aqueous phase volume ratio and used for the first VH/VL PCR amplification as shown in Table 18A and B.

TABLE 18A

| Mix | 1 tube | Final conc. | N tubes |
|---|---|---|---|
| $H_2O$ | 9 | — | 9 |
| 5X Go Taq Buffer | 10 | 1x | 10 |
| MgCl2 | 3 | 1.25 mM | 3 |
| dNTP 10 mM | 1 | 0.2 mM | 1 |
| Primer as - 5 µM | 2.5 | 0.25 µM | 2.5 |
| Primer s - 1.5 µM | 6.25 | 0.25 µM | 6.25 |
| Go Taq Polymerase | 0.25 | | 0.25 |
| DNA template | 18 | — | |
| Total | 50 | — | 32 |

TABLE 18B

| Thermo-cycling | | |
|---|---|---|
| | Time | Temp (° C.) |
| Activate Taq Polymerase: | 2 min | 95 |
| Denaturation: | 1 min | 95 |

TABLE 18B-continued

| Thermo-cycling | | | |
| --- | --- | --- | --- |
| | Time | Temp (° C.) | |
| Annealing: | 1 min | 55 | 25 cycles |
| Extension: | 1 min | 72 | |
| Finishing: | 10 min | 72 | |
| | Keep | 4° C. | |

The amplified VH and VL products were purified twice at 0.8× and 1×AMPure beads ratio, respectively. Half of the purified material was used for the second nested PCR reaction, as shown in Table 18A and B.

TABLE 19A

| Mix | 1 tube | Final conc. | N tubes |
| --- | --- | --- | --- |
| H₂O | 7 | — | 49 |
| 5X Go Taq Buffer | 10 | 1x | 70 |
| MgCl2 | 3 | 1.25 mM | 21 |
| dNTP 10 mM | 1 | 0.2 mM | 7 |
| Primer as - 5 µM | 2.5 | 0.25 µM | 17.5 |
| Primer s - 1.5 µM | 6.25 | 0.25 µM | 43.75 |
| Go Taq Polymerase | 0.25 | | 1.75 |
| DNA template | 20 | — | |
| Total | 50 | — | 210 |

TABLE 19B

| VH and VL Thermo-cycling | | | |
| --- | --- | --- | --- |
| | Time | Temp (° C.) | |
| Activate Taq Polymerase: | 2 min | 95 | |
| Denaturation: | 1 min | 95 | |
| Annealing: | 1 min | 55 | 15 cycles |
| Extension: | 1 min | 72 | |
| Finishing: | 10 min | 72 | |
| | Keep | 4° C. | |

The VH/VL amplified products were then purified using PCR purification kit (QIAGEN). A tenth was used for the third PCR reaction, performed as shown in Table 19A and B.

TABLE 20A

| Mix | 1 tube | Final conc. | N tubes |
| --- | --- | --- | --- |
| H₂O | 7 | — | 78.05 |
| 5X Go Taq Buffer | 10 | 1x | 28 |
| MgCl2 | 3 | 1.25 mM | 8.4 |
| dNTP 10 mM | 1 | 0.2 mM | 2.8 |
| Primer as - 51 µM | 2.5 | 0.25 µM | 7 |
| Primer s- 1.5 µM | 6.25 | 0.25 µM | 7 |
| Go Taq Polymerase | 0.25 | | 1.75 |
| DNA template | 20 | — | |
| Total | 50 | — | 133 |

TABLE 20B

| VH and VL Thermo-cycling | | |
| --- | --- | --- |
| | Time | Temp (° C.) |
| Activate Taq Polymerase: | 2 min | 95 |
| Denaturation: | 1 min | 95 |

TABLE 20B-continued

| VH and VL Thermo-cycling | | | |
| --- | --- | --- | --- |
| | Time | Temp (° C.) | |
| Annealing: | 1 min | 62 | 5 cycles |
| Extension: | 1 min | 72 | |
| Finishing: | 10 min | 72 | |
| | Keep | 4° C. | |

Amplified products were size selected on agarose gel, gel purified, quality controlled and sequenced on MiSeq 2*300 PE reads. Analysis was done by combining the information of the centrifuged and non-centrifuged cDNA sequencing library.

Sense VH and VL PCR primers used in the first and second PCR reaction were those described in the literature (Rohatgi, et al., 2008 Dec. 31; 339(2):205-19).

The Antisense primers used for PCR1 and 2 were as described in Example 4.

Sense primers used in PCR3: AATGATACGGCGAC-CACCGAGATCT ACACTCTTTCCCTA-CACGACGCTCTTCCGATCT (SEQ ID NO: 126).

Antisense primer used in PCR3: CAAGCAGAA-GACGGCATACGAGAT (SEQ ID NO: 127).

FIG. 6A depicts the number of primary B cells VH/VL pairings as a function of read threshold (for both VH and VL chains).

FIG. 6B depicts the number of different complementarity determining regions (CDRs) for the heavy and light chains based on read threshold per chain.

FIG. 6C depicts paired sequences reads sharing the same barcode (coming from the same cells) were plotted based on the number of VH and VL reads.

FIG. 6D depicts heavy variable gene usage in the paired sequences (at a threshold of 40 reads per chain)

FIG. 6E depicts kappa variable gene usage in the paired sequences (at a threshold of 40 reads per chain)

FIG. 6F depicts heavy J gene family usage in the paired sequences (at a threshold of 40 reads per chain)

FIG. 6G depicts kappa J gene family usage in the paired sequences (at a threshold of 40 reads per chain)

Example 7

Assessing Impact of Gene Specific Primer Concentration

The impact of gene specific primer concentration in RT reaction has been assessed in bulk reactions for mouse antibody VH and VL starting from cells (see FIG. 7). It was aimed at mimicking the drop conditions (especially the volume of reaction buffer per cell, the amount of reagent per cell).

Therefore, 40 000 mouse 9E10 hybridoma cells were used (pre-washed in Cell wash buffer (DMEM F12 media, 0.1% Pluronic, 25 mM Hepes, 5% low IgG serum)) in reaction volume mimicking 500 pL per cell (20 uL final reaction). The mix was as indicated in table 21 below:

TABLE 21

| | Final concentration | 1 sample |
| --- | --- | --- |
| H₂O RNase/DNase free | | µL |
| Cell Wash Buffer (Containing 40 000 | | 5 µL |

TABLE 21-continued

| | Final concentration | 1 sample |
|---|---|---|
| cells) | | |
| Lysis Buffer 10x (2% Triton, 30 mM MgCl2, 500 mM Tris-HCl pH 7.4) | 1x | 2 µL |
| 5x RT Buffer | 1x | 4 µL |
| dNTP 10 mM | 0.5 mM | 1 µL |
| 0.1M DTT | 5 mM | 1 µL |
| SS III RT enzyme (200 U/µl) | 12.5 U/µl | 1.25 µL |
| RNase Inhibitor | 1.25 U/µL | 1.25 µL |
| Protease Inhibitor (100x) | 1x | 0.2 µl |
| Final volume | | 18 µL |

Then different amount of VH and VL gene specific primer was added in concentrations as indicated in table 22.

TABLE 22

| | 1 uM each | 600 nM each | 300 nM each | 100 nM each | 60 nM each | 30 nM each | 10 nM each | 6 nM each | 3 nM each |
|---|---|---|---|---|---|---|---|---|---|
| Primers | 2 µL of 10 uM each | 1.2 µL of 10 uM each | 0.6 µL of 10 uM each | 2 µL of 1 uM each | 1.2 µL of 1 uM each | 0.6 µL of 1 uM each | 2 µL of 0.1 uM each | 1.2 µL of 0.1 uM each | 0.6 µL of 0.1 uM each |
| H2O | | 0.8 µL | 1.4 µL | | 0.8 µL | 1.4 µL | | 0.8 µL | 1.4 µL |

The pelleted cells were incubated into the mix for 10 min on ice to allow lysis to occur. The mix was incubated for 1 h at 55° C. mixed at 550 rpm. RT was then inactivated at 70° C. for 15 min at 550 rpm. Then cDNA was treated with RNAse A and PK to remove trace of PCR inhibitors. We added H$_2$O qsp 95 µL and added 1 µL of RNase A (10 mg/mL stock concentration, 100 ug/µL final concentration) and placed the DNase/RNase free DNA LoBind tube for 15 min at 37° C. We then added 4 µl of Proteinase K (20 mg/mL stock concentration, 0.8 mg/mL final concentration) and placed the tube for 1 h at 50° C. We inactivated PK for 15 minutes at 70° C. cDNA were then purified using RNA-CLeanup beads at 1x ratio (1 volume of bead solution with 1 volume of cDNA) and followed Beckman RNA Cleanup beads SOP. We eluted cDNA in 40 µL DNase/RNase free H$_2$O for 2 min and recovered eluted cDNA. We eluted for a second time the beads with 40 µL H$_2$O. The two elutions were pooled and we proceed to the second purification step using 1x RNAClean up beads (Beckman) exactly as before except only do a single elution with 40 µL H$_2$O. The amount of cDNA generated per condition was measured using absolute quantification qPCR based on multiplex qPCR reaction.

Impact of gene specific primer concentration was assessed in RT reaction in droplets for human antibody VH and VL starting from cell (see FIGS. 8A and B). 5000 human activated switched memory B cells from human healthy donor purified from PBMC and activated for 5 days were encapsulated in 500 pL drops containing either 100 nM or 10 nM of each gene specific primer for capturing heavy/light_kappa/Light_lambda chains. Each reagent (cells, lysis and RT reagents) was co-flowed in a microfluidic chip for 500 pL droplet production. The lysis/Pi/DTT/Dye containing solution was prepared as indicated below in table 23.

TABLE 23

| Mix | Volume [µl] | Final Concentration in the 200 µL mix | Final concentration in drop |
|---|---|---|---|
| Lysis Buffer 10x (v2) (2% Triton, 30 mM MgCl2, 500 mM Tris-HCl pH 7.4) | 80 µL | 4x | ≈1x |
| 100x Protease Inhibitor | 8 µL | 4x | ≈1x |
| Dye 647 100 uM | 8 µL | 4 µM | ≈1 µM |
| 1M DTT | 4 µL | 20 mM | ≈5 mM |
| H$_2$O | 100 µL | — | — |

50 µL of this mix was used for encapsulation and kept it on ice until aspiration into tip. The 2.6x RT mix preparation was prepared as indicated in table 24.

TABLE 24

| Mix | Volume [µl] | Final Concentration in the mix | Final concentration in drop |
|---|---|---|---|
| 5x SuperScript III RT buffer | 52 | 1.25x | 1x |
| dNTP 10 mM | 13 | 1.3 mM | 0.5 mM |
| RNase inhibitor (20 U/µL) | 16.25 | 3.25 U/µL | 1.25 U/µL |
| SuperScript III RT (200 U/µl) | 16.25 | 32.5 U/µL | 12.5 U/µL |
| Dye 647 100 µM | 2.5 | 2.5 µM | 0.9375 µM |
| Mix RT_primers 10 µM each (or 1 uM each) | 2.5 µL | 250 nM each GSP (or 25 nM each) | 100 nM each GSP (or 10 nM each) |

The cells washed and resuspended in Cell Suspension Buffer (CSB) containing the following reagents:

| | |
|---|---|
| Pluronic F68 10% | 10 µl |
| Hepes 1M | 25 µl |
| Serum low IgG | 50 µl |
| Media DMEM/F12 | 915 µl |

The produced drops were collected on ice to allow lysis to occur. The emulsion was Incubated for 1 h at 55° C. mixed at 550 rpm. RT was then inactivated at 70° C. for 15 min at 550 rpm. Then cDNA was treated with RNAse A and PK to remove trace of PCR inhibitors. We added H$_2$O qsp 95 µL and added 1 µL of RNase A (10 mg/mL stock concentration, 100 µg/µL final concentration) and placed the DNase/RNase free DNA LoBind tube for 15 min at 37° C. We then added 4 µl of Proteinase K (20 mg/mL stock concentration, 0.8 mg/mL final concentration) and placed the tube for 1 h at 50° C. We inactivated PK for 15 minutes at 70° C. cDNA was then purified using RNACLeanup beads at 0.8x ratio (1 volume of bead solution with 1 volume of cDNA) and followed Beckman RNA Cleanup beads SOP. We eluted cDNA in 40 μL DNase/RNase free $H_2O$ for 2 min and recovered eluted cDNA.

The amount of cDNA generated per condition was measured using absolute quantification qPCR based on multiplex qPCR reaction.

Impact of gene specific primer concentration in RT reaction was assessed in bulk reaction for non antibody gene starting from cells (see FIG. 9). We aimed at mimicking the drop conditions (especially the volume of reaction buffer per cell, the amount of reagent per cell).

We used 40 000 human Jurkat cells (pre-washed in Cell wash buffer (DMEM F12 media, 0.1% Pluronic, 25 mM Hepes, 5% low IgG serum)) in reaction volume mimicking 500 pL per cell (20 μL final reaction). The mix was as indicated in table 25:

TABLE 25

|  | Final | 1 μM | 0.1 μM | 0.01 μM | 0.001 μM |
|---|---|---|---|---|---|
| Mix (500 pl) | conc | oligo | oligo | oligo | oligo |
| $H_2O$ RNAse/DNase free |  | 2.3 μL | 4.1 μL | 2.3 μL | 4.1 μL |
| Cell wash buffer (containing 40.000 cells) |  | 5 μL | 5 μL | 5 μL | 5 μL |
| Lysis Buffer 10x (v2) (2% Triton, 30 mM $MgCl_2$, 500 mM Tris-HCl pH 7.4) | 1X | 2 μL | 2 μL | 2 μL | 2 μL |
| 5xRT buffer | 1X | 4 μL | 4 μL | 4 μL | 4 μL |
| dNTP 10 mM | 0.5 mM | 1 μL | 1 μL | 1 μL | 1 μL |
| 0.1M DTT | 5 mM | 1 μL | 1 μL | 1 μL | 1 μL |
| SS III RT enzyme (200 U/μL) | 12.5 U/μL | 1.25 μL | 1.25 μL | 1.25 μL | 1.25 μL |
| RNase inhibitor | 12.5 U/μL | 1.25 μL | 1.25 μL | 1.25 μL | 1.25 μL |
| 100x Protease Inhibitor | 1x | 0.2 μL | 0.2 μL | 0.2 μL | 0.2 μL |
| RT TRAT1/RPS29 primers |  | 2 μL (of 10 μM each) | 2 μL (of 10 μM each) | 2 μL (of 0.1 μM each) | 2 μL (of 0.1 μM each) |
| Final volume |  | 20 μL | — |  |  |

The pelleted cells were incubated into the mix for 10 min on ice to allow lysis to occur. The mix was Incubated for 1 h at 55° C. mixed at 550 rpm. RT was then inactivated at 70° C. for 15 min at 550 rpm. Then cDNA was treated with RNAseq A and PK to remove trace of PCR inhibitors. We added $H_2O$ qsp 95 uLμL and added 1 μl of RNase A (10 mg/mL stock concentration, 100 ug/uLμμ final concentration) and placed the DNase/RNase free DNA LoBind tube for 15 min at 37° C. We then added 4 μl of Proteinase K (20 mg/mL stock concentration, 0.8 mg/mL final concentration) and placed the tube for 1 h at 50° C. We inactivated PK for 15 minutes at 70° C. cDNa were then purified using RNA-CLeanup beads at 1x ratio (1 volume of bead solution with 1 volume of cDNA) and followed Beckman RNA Cleanup beads SOP. We eluted cDNA in 40 μL DNase/RNase free $H_2O$ for 2 min and recovered eluted cDNA. We eluted for a second time the beads with 40 μL $H_2O$. The two elutions were pooled together. The amount of cDNA generated per condition was measured using relative quantification qPCR based on simplex qPCR reaction.

Example 8

Assessing Impact of polydT Primer Concentration in RT Reaction

Assessing impact of polydT primer concentration in RT reaction for human whole transcriptome capture starting from cells has been performed in droplet reaction. A mixture of 20,000 cells composed of 95% human B cell Ramos cells and 5% human T cell Leukemia Jurkat cells was encapsulated in 500 pl droplets with Lysis buffer, RT reagents and either 3.3 uM or 100 nM or 33 nM of polydT primer. All reagents were co-flowed in a microfluidic chip for 500 pl droplets production.

The mix containing RT reagents was prepared as indicated in table 26 below.

TABLE 26

|  | Concentration | Volume (μL) | Final concentration | Units |
|---|---|---|---|---|
| First Strand buffer | 5X | 23.96 | 0.46 | X |
| IGEPAL CA-630 | 10% (V/V) | 9.16 | 0.35 | % |
| dNTPs | 10 mM | 12.21 | 0.47 | mM |

TABLE 26-continued

|  | Concentration | Volume (μL) | Final concentration | Units |
|---|---|---|---|---|
| DTT | 0.1M | 8.14 | 0 | M |
| Tris-Hcl | 1M | 12.21 | 0.05 | M |
| Murine Rnase inhibitor | 40 U/μL | 8.14 | 1.24 | U/μL |
| Superscript III RT enzyme | 200 U/μL | 12.21 | 9.3 | U/μL |
| Optiprep | 100x | 3.53 |  |  |
| Nuclease Free water |  | 6.19 |  |  |
| Dye 647 | 100 μM | 2 | 2 | uM |
| Total |  | 97.75 |  |  |

Then polydT RT primer were added at different concentration as indicated in table 27.

TABLE 27

|  | Concentration | Volume (μL) | Volume water | Final Concentration | Number of primer/droplet |
|---|---|---|---|---|---|
| polydT primer | 100 μM | 0.748 | 1.5 | 3.3 μM | 10^9 |
| polydT primer | 10 μM | 2.25 | — | 0.10 μM | 3.10^7 |
| polydT primer | 10 μM | 0.748 | 1.5 | 0.033 μM | 10^7 |

Cells were resuspended in a mix containing the concentrations indicated in table 28.

TABLE 28

| | Concentration | Volume (μL) | Final Concentration | Units |
|---|---|---|---|---|
| Cellules en PBS 1X | 1X | 50 | 0.23255814 | X |
| Optiprep | 100x | 16 | 7.441860465 | X |
| BSA | 0.2 mg/mL | 4 | 0.0037 | mg/ml |
| Dye 647 | 100 μM | 2 | 2 | uM |
| Nuclease free water | | 28 | | |
| Volume total | | 100 | | |

The last mix is composed of the ingredients and concentrations as indicated in table 29.

TABLE 29

| | Concentration | Volume (μL) | Final concentration | Units |
|---|---|---|---|---|
| 10 mM Tris HCl (pH 8), 0.1 mM EDTA and 0.1% (v/v) Tween 20 | 2x | 7.33 | | |
| BSA | 0.2 mg/mL | 0.345 | 0.0037 | mg/ml |
| Nuclease free water | — | 40.325 | | |
| Dye 647 | 100 μM | 2 | 2 | uM |
| Volume total | | 50 | | |

The droplets produced were collected on ice to allow Lysis to occur. The emulsion was incubated 2 h at 50° C. and RT was then inactivated at 70° C. for 15 min. The emulsion was then cooled down on ice and droplets were broken by adding 1 volume of a solution composed of 80% (v/v) HFE-7500 and 20% (v/v) perfluorooctanol. Then cDNA was centrifuged 15 min at 14,000 g at 4° C. and the supernatant recovered. To digest excess of primers and primer-dimers, cDNA were incubated with 1 μL of Exonuclease I (NEB, reference #M0293; 20,000 units/ml), 1 μL of Hinfl (NEB, #R0155; 10,000 units/ml) for 30 min at 37° C. We inactivated Exonuclease I and Hinfl enzymes for 10 min at 80° C. cDNA were then purified using Agencourt AMPure beads at 1.2× ratio (1.2 volume of bead with 1 volume cDNA) following Beckman Agencourt AMPure SOP. cDNA were eluted in 17 μL DNAse/RNAse free water for 2 min and we recovered eluted cDNA. The amount of cDNA generated per condition was measured using relative quantification qPCR based on simplex qPCR reaction.

Example 9

Impact of Gene Specific Primer Concentration on Gene Specific Reverse Transcription Capture efficiency (normalized to the 1 uM each gene specific primer) of mouse immonuglobulin variable heavy (VH) and variable light (VL) chains reverse transcription. 9E10 hybridoma cells were processed in bulk in RT reaction mimicking droplet conditions. This experiment mimics a drop condition (especially the volume of reaction buffer per cell, the amount of reagent per cell). For each condition, we used from 1 uM to 10 nM of each VH and VL gene specific primer. Comparisons are based on qPCR data. The Cp value (crossing point value determined by the $2^{nd}$ derivative max calculation method) was compared to each primer conditions. (n=2). Error bar=standard deviation (FIG. 7).

Capture efficiency (normalized to the 100 nM each gene specific primer) of human immonuglobulin variable heavy (VH) and variable light kappa (VLk) and lambda (VLl) chains reverse transcription. Human switched activated memory B cells (day 5 post activation) were encapsulated in 500 pL drops with lysis and RT reagents and either 100 nM or 10 nM of each gene specific primer was added in the mix. (Left) Comparisons are based on qPCR data for each immunoglobulin variable chain. The Cp value (crossing point value determined by the $2^{nd}$ derivative max calculation method) was compared to each primer conditions. (Right) Two steps nested PCR reaction amplified each VH and VL amplicon which were loaded on a 2% agarose gel stained with Sybr Gold. (n=2). Error bar=standard deviation (FIGS. 8A and B).

Capture efficiency (normalized to the 1 uM each gene specific primer) of human house keeping gene RPS29 and TRAT1 (from high to low expressed gene). Human T cell Leukemia (Jurkat cells) were processed in bulk in RT reaction mimicking droplet conditions and with either 1 uM, 100 nM, 10 nM, 1 nM of each gene specific primer. Comparisons are based on qPCR data for each specific gene. (n=2, 3 cDNA dilutions for each qPCR). Error bar=standard deviation. The highest expressed gene is less affected by primer concentration whereas the capture efficiency and RT of the lowest expressed gene is affected at 10 nM concentration of its RT primer concentration (FIG. 9).

Example 10

Impact of polydT Primer Concentration on Whole Transcriptome Capture and Reverse Transcription Capture efficiency of human housekeeping genes RPS29 and TRAT1 (from high to low expressed gene). Human T cell Leukemia (Jurkat) cells were encapsulated in 500 pL drops with lysis and RT reagents and either 3.3 μM or 100 or 33 nM of polydT primer was added in the mix. Comparisons are based on qPCR data for each specific gene. (n=1). n.d.=not detected. Both the highest and the lowest expressed gene are affected by primer concentration especially in low polydT primer concentration (FIG. 10).

---

The invention claimed is:

1. A method for capturing and barcoding single cell nucleic acids comprising:
   a) providing a plurality of cells contained within a plurality of droplets, at least some of the droplets each comprising a single cell, a reverse transcriptase and at least one type of an oligonucleotide, wherein the at least one type of oligonucleotide comprises a barcode sequence and a primer sequence, wherein each different primer sequence defines a different oligonucleotide type, and wherein a droplet containing one or more barcode sequences is distinguishable from the other droplets in said at least some of the droplets;
   b) lysing, within said at least some of the droplets, at least some of the cells to release nucleic acids from the cells;
   c) hybridizing, in said at least some of the droplets, at least some of the released nucleic acids to said oligonucleotide; and
   d) reverse transcribing, within said at least some of the droplets, the released nucleic acids hybridized to said oligonucleotide using the primer sequence;
   wherein each said at least some of the droplets has a volume of less than 3 nL, wherein each said at least some of the droplets has about 5 to 25 U/µL of reverse transcriptase, and,
   wherein each of said at least some of the droplets having a volume of approximately 0.1 nL, if present, is able to have an efficiency of reverse transcription of 10% when compared to that of purified RNA extracted from the plurality of cells.

2. The method according to claim 1, wherein the concentration of each type of oligonucleotide in the droplets is at least 100 nM.

3. The method of claim 2, wherein the concentration of each type of oligonucleotide in the droplets is about 100 nM to about 5 µM.

4. The method of claim 3, wherein the concentration of each type of oligonucleotide in the droplets is about 100 nM to about 1 µM.

5. The method of claim 4, wherein the concentration of each type of oligonucleotide in the droplets is about 100 nM to about 500 nM.

6. The method of claim 2, wherein the concentration of each type of oligonucleotide in the droplets is at least 200 nM.

7. The method according to claim 1, wherein step a) further comprises providing a plurality of particles contained within said plurality of droplets, and wherein at least some of the droplets further comprise a particle.

8. The method according to claim 7, wherein the at least one type of an oligonucleotide is bonded to said particle.

9. The method according to claim 7, wherein the plurality of particles are contained within the droplets at an average of no more than about 1 particle per droplet.

10. The method according to claim 9, wherein different types of oligonucleotides bound to the particle contained in one droplet comprise the same barcode sequence.

11. The method according to claim 10, comprising releasing at least some of the oligonucleotides from the particles prior to or after lysing the cells.

12. The method according to claim 1, wherein each droplet has a volume equal to or less than 1 nL.

13. The method according to claim 1, which further comprises recovering single cell cDNAs produced by reverse transcription in at least some of the droplets.

14. The method according to claim 1, wherein the one or more barcode sequences uniquely identify the nucleic acids released by a single cell from nucleic acids released from other cells.

15. The method according to claim 1, wherein the at least one type of oligonucleotide comprises a primer sequence selected from the group consisting of a poly-T sequence, a random DNA sequence, and a gene-specific sequence.

16. The method according to claim 15, wherein the primer sequence is a gene-specific sequence and the gene is selected from the group consisting of antibody heavy variable gene, antibody heavy constant gene, antibody light variable gene, antibody light constant gene, alpha T-cell receptor gene, beta T-cell receptor gene, delta T-cell receptor gene and gamma T-cell receptor gene.

17. The method of claim 1, wherein each said at least some of the droplets has about 12.5 U/μL or about 25 U/μL of reverse transcriptase.

18. The method of claim 1, wherein each said at least some of the droplets has about 3.3 mM of MgCl$_2$.

* * * * *